United States Patent
Wagner et al.

(10) Patent No.: US 8,232,312 B2
(45) Date of Patent: Jul. 31, 2012

(54) SUBSTITUTED ARYLSULPHONYLGLYCINES, THE PREPARATION THEREOF AND THE USE THEREOF AS PHARMACEUTICAL COMPOSITIONS

(75) Inventors: Holger Wagner, Mettenberg (DE); Elke Langkopf, Warthausen (DE); Matthias Eckhardt, Biberach (DE); Ruediger Streicher, Biberach (DE); Corinna Schoelch, Mittelbiberach (DE); Annette Schuler-Metz, Ulm (DE); Alexander Pautsch, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 177 days.

(21) Appl. No.: 12/530,507

(22) PCT Filed: Mar. 14, 2008

(86) PCT No.: PCT/EP2008/053087
§ 371 (c)(1),
(2), (4) Date: Dec. 4, 2009

(87) PCT Pub. No.: WO2008/113760
PCT Pub. Date: Sep. 25, 2008

(65) Prior Publication Data
US 2010/0130557 A1 May 27, 2010

(30) Foreign Application Priority Data

Mar. 16, 2007 (DE) .......... 10 2007 012 284

(51) Int. Cl.
A61K 31/5377 (2006.01)
A61K 31/497 (2006.01)
A61K 31/496 (2006.01)
A61K 31/454 (2006.01)
A61K 31/4439 (2006.01)
A61K 31/428 (2006.01)
A61K 31/4184 (2006.01)
A61K 31/416 (2006.01)
A61K 31/404 (2006.01)
C07D 413/06 (2006.01)
C07D 401/06 (2006.01)
C07D 401/12 (2006.01)
C07D 403/06 (2006.01)
C07D 403/12 (2006.01)
C07D 277/64 (2006.01)
C07D 333/60 (2006.01)
C07D 235/26 (2006.01)
C07D 235/08 (2006.01)
C07D 231/56 (2006.01)
C07D 209/42 (2006.01)
C07D 209/08 (2006.01)
C07D 209/88 (2006.01)

(52) U.S. Cl. ........ 514/415; 514/411; 514/443; 514/339; 514/406; 514/387; 514/323; 514/235.2; 514/254.09; 514/367; 514/255.05; 514/397; 548/490; 548/491; 548/509; 548/510; 548/504; 548/444; 548/362.5; 548/361.1; 548/306.4; 548/304.4; 548/178; 548/312.1; 546/278.1; 546/277.4; 546/201; 544/143; 544/373; 544/405; 549/57

(58) Field of Classification Search ........... 514/415, 514/411, 443, 339, 406, 387, 323, 235.2, 514/254.09, 367, 255.05, 394; 544/143, 544/373, 405; 546/278.1, 277.4, 201; 548/490, 548/491, 509, 510, 504, 444, 362.5, 361.1, 548/306.4, 304.4, 178, 312.1; 549/57
See application file for complete search history.

(56) References Cited

U.S. PATENT DOCUMENTS

| 6,114,532 | A * | 9/2000 | Ries et al. ............ 546/162 |
| 6,812,250 | B2 | 11/2004 | Defossa et al. |
| 7,138,414 | B2 | 11/2006 | Schoenafinger et al. |
| 7,223,796 | B2 | 5/2007 | Defossa et al. |
| 7,262,220 | B2 | 8/2007 | Defossa et al. |
| 7,989,622 | B2 | 8/2011 | Bajjalieh et al. |
| 2006/0142250 | A1 | 6/2006 | Blaskovich et al. |
| 2010/0093703 | A1 | 4/2010 | Wagner et al. |
| 2010/0130557 | A1 | 5/2010 | Wagner et al. |
| 2010/0210594 | A1 | 8/2010 | Wagner et al. |

(Continued)

FOREIGN PATENT DOCUMENTS

EP 0604657 A1 7/1994

(Continued)

OTHER PUBLICATIONS

Jordan, V. C. Nature Reviews: Drug Discovery, 2, 2003, pp. 205-213.*

(Continued)

*Primary Examiner* — Joseph Kosack
*Assistant Examiner* — Matthew Coughlin
(74) *Attorney, Agent, or Firm* — Michael P. Morris; David L. Kershner; Usha R. Patel

(57) ABSTRACT

The present invention relates to substituted arylsulphonylglycines of general formula (I) wherein R, X, Y and Z are defined as in claim 1, the tautomers, enantiomers, diastereomers, mixtures thereof and salts thereof, which have valuable pharmacological properties, particularly the suppression of the interaction of glycogen phosphorylase a with the GL subunit of glycogen-associated protein phosphatase 1 (PP1), and their use as pharmaceutical compositions.

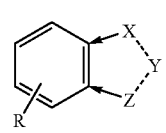

11 Claims, No Drawings

U.S. PATENT DOCUMENTS

2010/0210595 A1      8/2010    Wagner et al.

FOREIGN PATENT DOCUMENTS

| | | | |
|---|---|---|---|
| EP | 0638581 | A1 | 2/1995 |
| EP | 0 174 542 | A1 | 2/2001 |
| JP | 2005206492 | A | 8/2005 |
| WO | 9928297 | A1 | 6/1999 |
| WO | 0170754 | A1 | 9/2001 |
| WO | 02096864 | A1 | 12/2002 |
| WO | 03084922 | A1 | 10/2003 |
| WO | 2004007437 | A1 | 1/2004 |
| WO | 2004007455 | A1 | 1/2004 |
| WO | 2004104001 | A2 | 12/2004 |
| WO | 2005/013976 | A1 | 2/2005 |
| WO | 2005/013977 | A1 | 2/2005 |
| WO | 2005/013978 | A1 | 2/2005 |
| WO | 2005024535 | A2 | 3/2005 |
| WO | 2006034418 | A2 | 3/2006 |
| WO | 2006052722 | A1 | 5/2006 |
| WO | 2007044729 | A2 | 4/2007 |
| WO | 2008/099000 | A2 | 8/2008 |
| WO | 2008103354 | A2 | 8/2008 |
| WO | 2008113760 | A2 | 9/2008 |
| WO | 2009016118 | A1 | 2/2009 |
| WO | 2009016119 | A1 | 2/2009 |
| WO | 2009030715 | A1 | 3/2009 |

OTHER PUBLICATIONS

Cohen, P. Nature Reviews Molecular Cell Biology 2006, 7, 867-874.*

Zibrova et al. Biochem J. 2008, 412, 359-365.*

International Search Report for PCT/EP2008/053087 mailed Sep. 5, 2008.

U.S Appl. No. 12/527,249, filed Aug. 14, 2009.

Abstract in English for JP200506492 cited herein.

Chen, et al. "Discovering Benzamide Derivatives as Glycogen Phosphorylase Inhibitors and Their Binding Site at the Enzyme" 15 Bioorg. & Med. Chem. pp. 6763-6774 (2007).

International Search Report for PCT/EP2008/059805 mailed Nov. 6, 2008.

International Search Report for PCT/EP2008/059807 mailed Nov. 12, 2008.

International Search Report for PCT/EP2008/061651 mailed Dec. 1, 2008.

Martin, Yvonne C. et al. "Do Structurally Similar Molecules Have Similar Biological Activity?" 45 J. Med. Chem. pp. 4350-4358 (2002).

WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pages 681. This PCT publication is too large for EFS submission via the foreign patent section, therefore submitting in two parts in the NPL section. pp. 1-340.

WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pages 681. This PCT publication is too large for EFS submission via the foreign patent section, therefore submitting in two parts in the NPL section. pp. 341-681.

* cited by examiner

SUBSTITUTED ARYLSULPHONYLGLYCINES, THE PREPARATION THEREOF AND THE USE THEREOF AS PHARMACEUTICAL COMPOSITIONS

This application is the national phase entry under 35 U.S.C. §371 of International Application No. PCT/EP2008/053087, filed Mar. 14, 2008, which claims priority to German Application No. DE 102007012284.7, filed Mar. 16, 2007, each of which is hereby incorporated by reference in its entirety.

The present invention relates to substituted arylsulphonylglycines of general formula I

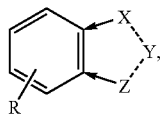

wherein the groups R, X, Y and Z are defined as hereinafter, including the tautomers, stereoisomers, mixtures thereof and salts thereof. This invention further relates to pharmaceutical compositions containing a compound of formula I according to the invention as well as the use of a compound according to the invention for preparing a pharmaceutical composition for the treatment of metabolic disorders, particularly type 1 or type 2 diabetes mellitus. The invention also relates to processes for preparing a pharmaceutical composition as well as a compound according to the invention.

Compounds of formula I are suitable for preventing the inhibiting effect of glycogen phosphorylase on the activity of glycogen synthase by stopping the interaction of glycogen phosphorylase a with the $G_L$ subunit of glycogen-associated protein phosphatase 1 (PP1). Compounds with these properties stimulate glycogen synthesis and are proposed for the treatment of metabolic disorders, particularly diabetes (P. Cohen, *Nature Reviews Molecular Cell Biology* 2006, 7, 867-874).

AIM OF THE INVENTION

The aim of the present invention is to provide new arylsulphonylglycines that suppress the interaction of glycogen phosphorylase a with the $G_L$ subunit of glycogen-associated protein phosphatase 1 (PP1).

A further aim of the present invention is to provide new pharmaceutical compositions that are suitable for the prevention and/or treatment of metabolic disorders, particularly diabetes.

Another aim of this invention is to provide a process for preparing the compounds according to the invention.

Other aims of the present invention will become directly apparent to the skilled man from the foregoing remarks and those that follow.

OBJECT OF THE INVENTION

In a first aspect the present invention relates to new substituted arylsulphonylglycines of general formula

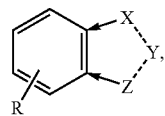

wherein
R denotes a group of formula

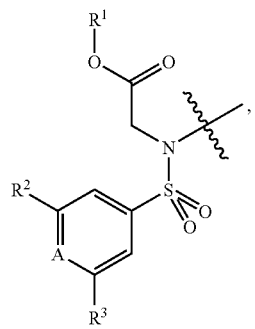

wherein
$R^1$ denotes H, $C_{1-6}$-alkyl or a group of formula

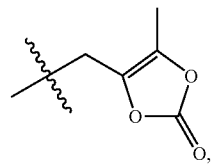

wherein the $C_{1-6}$-alkyl group mentioned for $R^1$ hereinbefore may be substituted by $C_{1-6}$-alkyl-carbonyloxy, $C_{1-6}$-alkoxy-carbonyloxy, $C_{1-6}$-alkoxy, hydroxy, amino, $C_{1-3}$-alkyl-amino, di-($C_{1-3}$-alkyl)-amino, pyrrolidin-1-yl, piperidin-1-yl, morpholin-4-yl, piperazin-1-yl, 4-($C_{1-3}$-alkyl)piperazin-1-yl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, tetrahydrofuran-3-yloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy or 4-($C_{1-3}$-alkyl)piperazin-1-yl-$C_{1-3}$-alkyloxy, $R^2$ and $R^3$ independently of one another denote halogen, $C_{1-3}$-alkyl, $C_{2-4}$-alkynyl, $C_{1-3}$-perfluoroalkyl, $C_{1-3}$-perfluoroalkoxy, $C_{1-3}$-alkoxy, cyano, nitro or hydroxy, and A denotes CH or N,
and the heterocyclic group

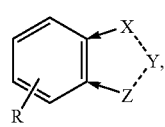

denotes a group of formula

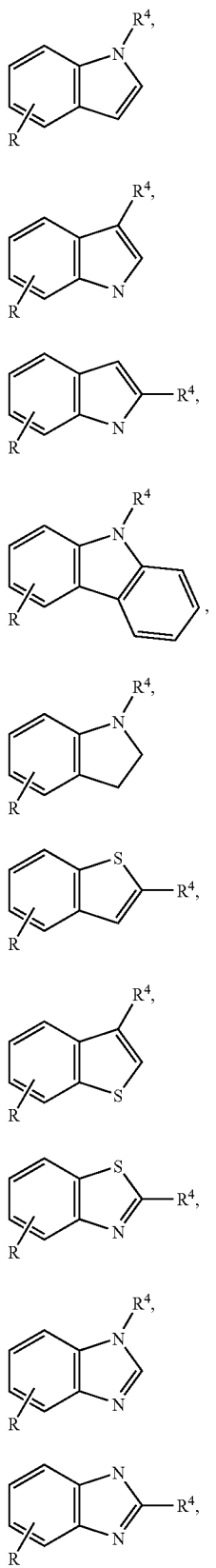

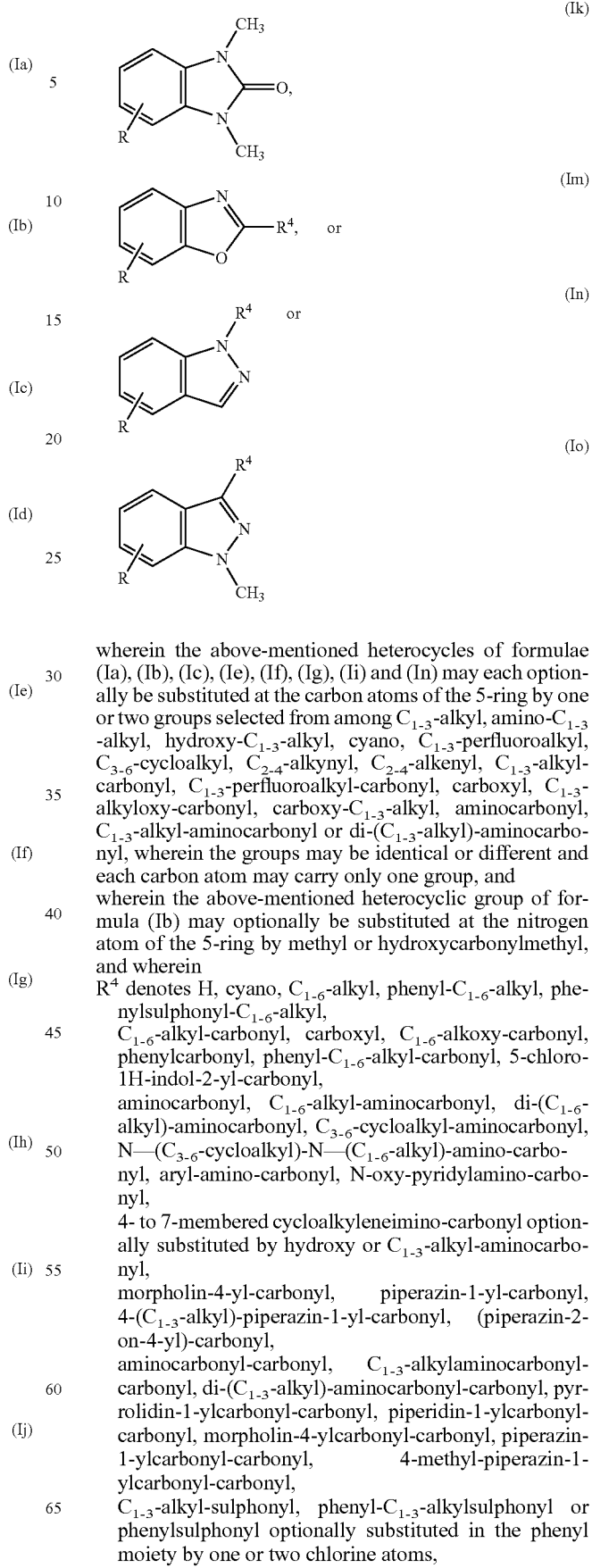

wherein the above-mentioned heterocycles of formulae (Ia), (Ib), (Ic), (Ie), (If), (Ig), (Ii) and (In) may each optionally be substituted at the carbon atoms of the 5-ring by one or two groups selected from among $C_{1-3}$-alkyl, amino-$C_{1-3}$-alkyl, hydroxy-$C_{1-3}$-alkyl, cyano, $C_{1-3}$-perfluoroalkyl, $C_{3-6}$-cycloalkyl, $C_{2-4}$-alkynyl, $C_{2-4}$-alkenyl, $C_{1-3}$-alkyl-carbonyl, $C_{1-3}$-perfluoroalkyl-carbonyl, carboxyl, $C_{1-3}$-alkyloxy-carbonyl, carboxy-$C_{1-3}$-alkyl, aminocarbonyl, $C_{1-3}$-alkyl-aminocarbonyl or di-($C_{1-3}$-alkyl)-aminocarbonyl, wherein the groups may be identical or different and each carbon atom may carry only one group, and wherein the above-mentioned heterocyclic group of formula (Ib) may optionally be substituted at the nitrogen atom of the 5-ring by methyl or hydroxycarbonylmethyl, and wherein $R^4$ denotes H, cyano, $C_{1-6}$-alkyl, phenyl-$C_{1-6}$-alkyl, phenylsulphonyl-$C_{1-6}$-alkyl, $C_{1-6}$-alkyl-carbonyl, carboxyl, $C_{1-6}$-alkoxy-carbonyl, phenylcarbonyl, phenyl-$C_{1-6}$-alkyl-carbonyl, 5-chloro-1H-indol-2-yl-carbonyl, aminocarbonyl, $C_{1-6}$-alkyl-aminocarbonyl, di-($C_{1-6}$-alkyl)-aminocarbonyl, $C_{3-6}$-cycloalkyl-aminocarbonyl, N—($C_{3-6}$-cycloalkyl)-N—($C_{1-6}$-alkyl)-amino-carbonyl, aryl-amino-carbonyl, N-oxy-pyridylamino-carbonyl, 4- to 7-membered cycloalkyleneimino-carbonyl optionally substituted by hydroxy or $C_{1-3}$-alkyl-aminocarbonyl, morpholin-4-yl-carbonyl, piperazin-1-yl-carbonyl, 4-($C_{1-3}$-alkyl)-piperazin-1-yl-carbonyl, (piperazin-2-on-4-yl)-carbonyl, aminocarbonyl-carbonyl, $C_{1-3}$-alkylaminocarbonyl-carbonyl, di-($C_{1-3}$-alkyl)-aminocarbonyl-carbonyl, pyrrolidin-1-ylcarbonyl-carbonyl, piperidin-1-ylcarbonyl-carbonyl, morpholin-4-ylcarbonyl-carbonyl, piperazin-1-ylcarbonyl-carbonyl, 4-methyl-piperazin-1-ylcarbonyl-carbonyl, $C_{1-3}$-alkyl-sulphonyl, phenyl-$C_{1-3}$-alkylsulphonyl or phenylsulphonyl optionally substituted in the phenyl moiety by one or two chlorine atoms, wherein the $C_{1-6}$-alkyl-aminocarbonyl, di-($C_{1-6}$-alkyl)-aminocarbonyl and N—($C_{3-6}$-cycloalkyl)-N—($C_{1-6}$-alkyl)-amino-carbonyl group mentioned above in the definition of $R^4$ may each be substituted in the alkyl moiety by aryl, $C_{1-3}$-alkyl-amino, di-($C_{1-3}$-alkyl)-amino, $C_{3-6}$-cycloalkyl-amino, N—($C_{3-6}$-cycloalkyl)-N—($C_{1-6}$-alkyl)-amino, pyrrolidin-1-yl, piperidin-1-yl, morpholin-4-yl, piperazin-1-yl, 4-methyl-piperazin-1-yl or $C_{1-3}$-alkylaminocarbonyl, and wherein the aryl group mentioned above in the definition of $R^4$ is a 6-membered aromatic system that may contain 0 to 3 nitrogen atoms and may be substituted by nitro.

The invention also relates to the tautomers, stereoisomers, mixtures and salts, particularly the physiologically acceptable salts, of the compounds according to the invention.

The compounds of general formula I according to the invention and the physiologically acceptable salts thereof have valuable pharmacological properties, in particular they suppress the interaction of glycogen phosphorylase a with the $G_L$-subunit of glycogen-associated protein phosphatase 1 (PP1).

Therefore this invention also relates to the use of the compounds according to the invention, including the physiologically acceptable salts, as pharmaceutical compositions.

The compounds of the above general formula I, wherein $R^1$ does not represent hydrogen, but denotes one of the other groups specified, are so-called prodrugs. By prodrugs are meant compounds that are not active per se but are converted into the corresponding active compound in vivo, cleaving the prodrug group.

This invention further relates to pharmaceutical compositions containing at least one compound according to the invention or a physiologically acceptable salt according to the invention, optionally together with one or more inert carriers and/or diluents.

A further object of this invention is the use of at least one compound according to the invention or a physiologically acceptable salt of such a compound for preparing a pharmaceutical composition that is suitable for the treatment or prevention of diseases or conditions that can be influenced by suppressing the interaction of glycogen phosphorylase a with the $G_L$-subunit of glycogen-associated protein phosphatase 1 (PP1).

The invention also relates to the use of at least one compound according to the invention for preparing a pharmaceutical composition which is suitable for the treatment of metabolic disorders, for example type I or II diabetes mellitus.

The invention also relates to the use of at least one compound according to the invention for preparing a pharmaceutical composition for suppressing the interaction of glycogen phosphorylase a with the $G_L$-subunit of glycogen-associated protein phosphatase 1 (PP1).

A further object of this invention is a process for preparing a pharmaceutical composition according to the invention, characterised in that a compound according to the invention is incorporated in one or more inert carriers and/or diluents by a non-chemical method.

The present invention also relates to a process for preparing the compounds of general formula I according to the invention.

DETAILED DESCRIPTION OF THE INVENTION

Unless stated otherwise, the groups, radicals and substituents, particularly R, $R^1$ to $R^4$, X, Y, Z and A have the meanings given hereinbefore and hereinafter.

If groups, substituents or radicals occur more than once in a compound, they may have the same or different meanings.

Preferred compounds of the above general formula I are those wherein

R denotes a group of the above-mentioned formula wherein
$R^1$ denotes H, $C_{1-6}$-alkyl or a group of formula

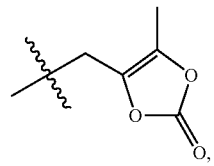

wherein the $C_{1-6}$-alkyl group mentioned for $R^1$ hereinbefore may be substituted by $C_{1-6}$-alkyl-carbonyloxy, $C_{1-6}$-alkoxy-carbonyloxy, $C_{1-6}$-alkoxy, hydroxy, amino, $C_{1-3}$-alkyl-amino, di-($C_{1-3}$-alkyl)-amino, pyrrolidin-1-yl, piperidin-1-yl, morpholin-4-yl, piperazin-1-yl, 4-($C_{1-3}$-alkyl)piperazin-1-yl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl, $R^2$ and $R^3$ independently of one another denote halogen, $C_{1-3}$-alkyl, $C_{2-4}$-alkynyl, $C_{1-3}$-perfluoroalkyl, $C_{1-2}$-alkoxy or cyano and A denotes CH or N, and the heterocyclic group

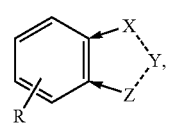

denotes a group of formula

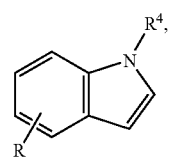

(Ia)

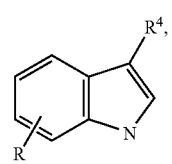

(Ib)

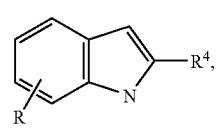

(Ic)

-continued (Id)

(Ie)

(If)

(Ig)

(Ii)

(Ij)

(Ik)

(In)

(Io)

wherein the above-mentioned heterocycles of formulae (Ia), (Ib), (Ic), (Ie), (If), (Ig), (Ii) and (In) may each optionally be substituted at the carbon atoms of the 5-ring by one or two groups selected from among $C_{1-3}$-alkyl, amino-$C_{1-3}$-alkyl, hydroxy-$C_{1-3}$-alkyl, cyano, $C_{3-6}$-cycloalkyl, $C_{1-3}$-alkyl-carbonyl, $C_{1-3}$-perfluoroalkyl-carbonyl, carboxyl, $C_{1-2}$-alkyloxy-carbonyl, carboxy-$C_{1-2}$-alkyl, aminocarbonyl, $C_{1-3}$-alkyl-aminocarbonyl or di-($C_{1-3}$-alkyl)-aminocarbonyl, wherein the groups may be identical or different and each carbon atom may carry only one group, and wherein the above-mentioned heterocyclic group of formula (Ib) may optionally be substituted at the nitrogen atom of the 5-ring by methyl or hydroxycarbonylmethyl, and wherein $R^4$ denotes H, cyano, $C_{1-4}$-alkyl, phenyl-$C_{1-4}$-alkyl, phenylsulphonyl-$C_{1-4}$-alkyl, $C_{1-4}$-alkyl-carbonyl, carboxyl, $C_{1-4}$-alkoxy-carbonyl, phenylcarbonyl, phenyl-$C_{1-4}$-alkyl-carbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-amino-carbonyl, [N,N-di-($C_{1-4}$-alkyl)amino]-$C_{1-3}$-alkyl-amino-carbonyl, 1-(methylaminocarbonyl)-ethyl-amino-carbonyl, aryl-amino-carbonyl, aryl-$C_{1-3}$-alkyl-amino-carbonyl, N-oxy-pyridylamino-carbonyl, 4- to 7-membered cycloalkyleneimino-carbonyl optionally substituted by hydroxy or methylaminocarbonyl, morpholin-4-yl-carbonyl, piperazin-1-yl-carbonyl, 4-(methyl)-piperazin-1-yl-carbonyl, (piperazin-2-on-4-yl)-carbonyl, aminocarbonyl-carbonyl, $C_{1-2}$-alkylaminocarbonyl-carbonyl, di-($C_{1-2}$-alkyl)-aminocarbonyl-carbonyl, pyrrolidin-1-ylcarbonyl-carbonyl, piperidin-1-ylcarbonyl-carbonyl, morpholin-4-ylcarbonyl-carbonyl, $C_{1-2}$-alkyl-sulphonyl, phenyl-$C_{1-2}$-alkyl-sulphonyl or phenylsulphonyl optionally substituted in the phenyl moiety by one or two chlorine atoms, while the aryl group mentioned above in the definition of $R^4$ is a 6-membered aromatic system that may contain 0 to 2 nitrogen atoms and may be substituted by nitro.

Particularly preferred are those compounds of the above general formula I, wherein R denotes a group of the above-mentioned formula wherein $R^1$ denotes H, $C_{1-4}$-alkyl or a group of formula wherein the $C_{1-4}$-alkyl group mentioned for $R^1$ hereinbefore may be substituted by $C_{1-4}$-alkoxy, hydroxy, di-($C_{1-3}$-alkyl)-amino, pyrrolidin-1-yl, piperidin-1-yl, morpholin-4-yl, piperazin-1-yl or 4-(methyl)-piperazin-1-yl, $R^2$ and $R^3$ independently of one another denote chlorine, bromine, $C_{1-2}$-alkoxy, $C_{2-3}$-alkynyl or $C_{1-2}$-alkyl and A denotes CH or N, and the heterocyclic group denotes a group of formula

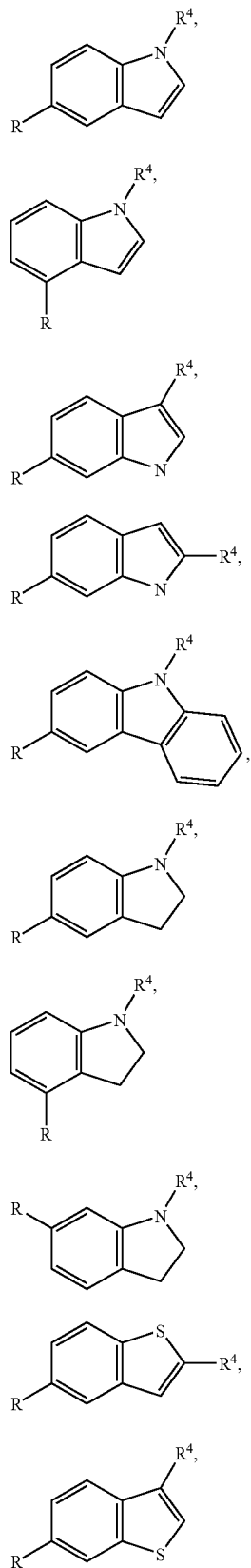

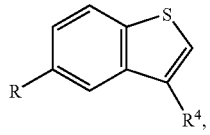

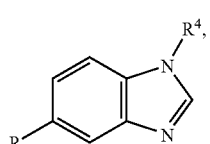

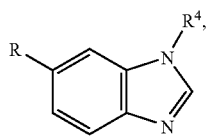

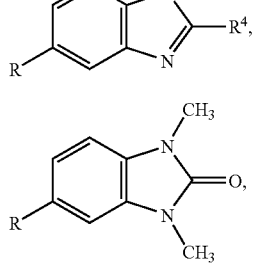

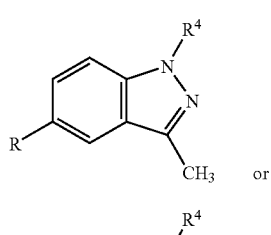

wherein the above-mentioned heterocycles of formulae (Ia1), (Ia2) and (Ie1) may each optionally be substituted at the carbon atoms of the 5 ring by a group selected from among $C_{1-2}$-alkyl, methylcarbonyl, trifluoromethylcarbonyl, carboxyl, methoxy-carbonyl, aminocarbonyl, methyl-aminocarbonyl, dimethyl-aminocarbonyl, aminomethyl or hydroxymethyl, and wherein the above-mentioned heterocyclic group of formula (Ib1) may optionally be substituted at the nitrogen atom of the 5 ring by methyl or hydroxycarbonylmethyl, and wherein $R^4$ denotes H, cyano, $C_{1-4}$-alkyl, phenyl-$C_{1-4}$-alkyl, phenylsulphonyl-$C_{1-4}$-alkyl, $C_{1-4}$-alkyl-carbonyl, carboxyl, $C_{1-4}$-alkoxy-carbonyl, phenylcarbonyl, phenyl-$C_{1-4}$-alkyl-carbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N—($C_{3-6}$-cycloalkyl)-N—($C_{1-4}$-alkyl)-amino-carbonyl, N,N-di-($C_{1-3}$-alkyl)amino-$C_{1-3}$-alkyl-amino-carbonyl, 1-(methylaminocarbonyl)-ethyl-amino-carbonyl, phenylamino-carbonyl, (nitrophenyl)-amino-carbonyl, phenyl-$C_{1-2}$-alkyl-amino-carbonyl, pyridinylamino-carbonyl, pyrazinylamino-carbonyl, N-oxy-pyridylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, $C_{1-2}$-alkylaminocarbonyl-carbonyl, di-($C_{1-2}$-alkyl)-aminocarbonyl-carbonyl, pyrrolidin-1-ylcarbonyl-carbonyl, piperidin-1-ylcarbonyl-carbonyl, morpholin-4-ylcarbonyl-carbonyl, benzyl-sulphonyl, phenylsulphonyl or 3.5-dichloro-phenyl-sulphonyl, but particularly those compounds of the above general formula I, wherein
R denotes a group of the above-mentioned formula wherein
$R^1$ denotes H or a $C_{1-3}$-alkyl group optionally substituted by a di-($C_{1-3}$-alkyl)-amino group,
$R^2$ and $R^3$ independently of one another represent chlorine, ethynyl, methoxy, methyl or ethyl and
A denotes CH or N,
and the heterocyclic group

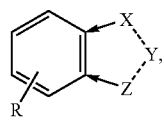

denotes a group of formula

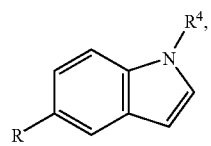
(Ia1)

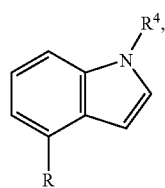
(Ia2)

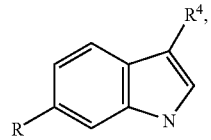
(Ib1)

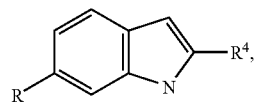
(Ic1)

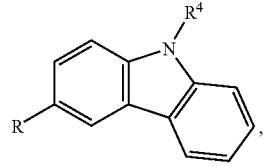
(Id1)

-continued

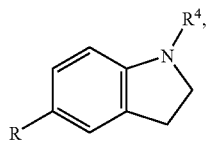
(Ie1)

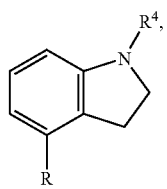
(Ie2)

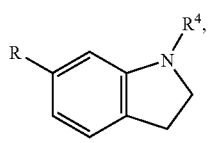
(Ie3)

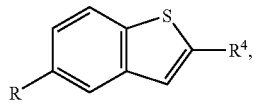
(If1)

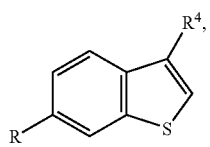
(Ig1)

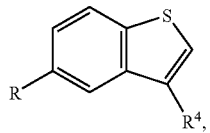
(Ig2)

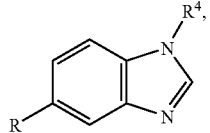
(Ii1)

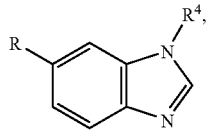
(Ii2)

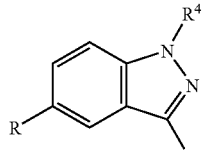
(In1)

or

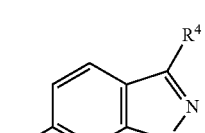
(Io1)

wherein the above-mentioned heterocycles of formulae (Ia1) and (Ie1) may each optionally be substituted at the carbon atoms of the 5-ring by a group selected from among $C_{1-2}$alkyl, trifluoromethylcarbonyl, carboxyl, aminocarbonyl or hydroxymethyl, and wherein the above-mentioned heterocyclic group of formula (Ib1) may optionally be substituted at the nitrogen atom of the 5-ring by methyl or hydroxycarbonylmethyl, and wherein $R^4$ denotes H, cyano, $C_{1-3}$-alkyl, phenyl-$C_{1-2}$-alkyl, phenylsulphonyl-$C_{1-2}$-alkyl, $C_{1-3}$-alkyl-carbonyl, $C_{1-2}$-alkoxy-carbonyl, phenylcarbonyl, phenyl-$C_{1-2}$-alkyl-carbonyl, 5-chloro-1H-indol-2-yl-carbonyl, aminocarbonyl, $C_{1-3}$-alkyl-aminocarbonyl, di-($C_{1-3}$-alkyl)-aminocarbonyl, cyclopropyl-aminocarbonyl, N-(cyclopropyl)-N—($C_{1-2}$-alkyl)-amino-carbonyl, (N,N-dimethyl-amino)-ethyl-amino-carbonyl, 1-(methylaminocarbonyl)-ethyl-amino-carbonyl, phenylamino-carbonyl, (nitrophenyl)-amino-carbonyl, phenyl-$C_{1-3}$-alkyl-carbonyl, phenyl-$C_{1-2}$-alkyl-amino-carbonyl, pyridinylamino-carbonyl, pyrazinylamino-carbonyl, N-oxy-pyridin-3-ylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, $C_{1-2}$-alkylaminocarbonyl-carbonyl, di-($C_{1-2}$-alkyl)-aminocarbonyl-carbonyl, pyrrolidin-1-ylcarbonyl-carbonyl, benzyl-sulphonyl or phenyl-sulphonyl.

Most particularly preferred are those compounds of the above general formula I, wherein R denotes a group of the above-mentioned formula wherein $R^1$ denotes H, methyl, ethyl or 2-dimethylamino-ethyl, $R^2$ and $R^3$ independently of one another denote chlorine, ethynyl, methoxy, methyl or ethyl and A denotes CH or N, and the heterocyclic group

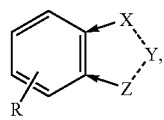

which may be substituted by $R^4$ as hereinbefore described, denotes a group of formula

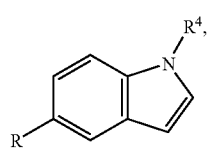
(Ia1)

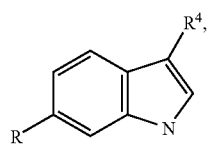
(Ib1)

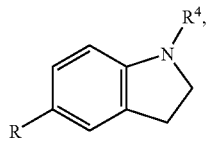
(Ie1)

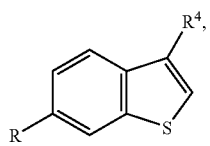
(Ig1)

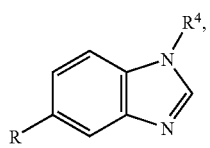
(Ii1)

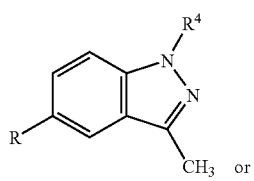
(In1)

or

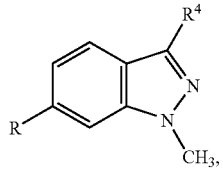
(Io1)

wherein the above-mentioned heterocyclic group of formula (Ia1) may optionally be substituted by trifluoromethylcarbonyl at the carbon atom of the 5-ring adjacent to the phenyl ring, and wherein the above-mentioned heterocyclic group of formula (Ie1) may optionally be substituted by carboxyl, amino-carbonyl or hydroxymethyl at the carbon atom of the 5-ring adjacent to the phenyl ring, and wherein the above-mentioned heterocyclic group of formula (Ib1) may optionally be substituted by methyl or hydroxycarbonylmethyl at the nitrogen atom of the 5 ring, and wherein $R^4$ denotes H, cyano, ethyl, phenyl-ethyl, phenylsulphonyl-ethyl, methyl-carbonyl, methoxy-carbonyl, phenylcarbonyl, benzylcarbonyl, 5-chloro-1H-indol-2-yl-carbonyl, aminocarbonyl, methyl-aminocarbonyl, dimethyl-aminocarbonyl, cyclopropyl-aminocarbonyl, N-(cyclopropyl)-N-(methyl)-aminocarbonyl, (N,N-dimethyl-amino)-ethyl-amino-carbonyl, 1-(methylaminocarbonyl)-ethyl-amino-carbonyl, phenylamino-carbonyl, benzylamino-carbonyl, 3-nitrophenylamino-carbonyl, 2-nitro-phenylamino-carbonyl, pyridin-3-ylamino-carbonyl, pyridin-4-ylamino-carbonyl, pyrazinylamino-carbonyl, N-oxy-pyridin-3-ylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, methylaminocarbonyl-carbonyl, dimethyl-aminocarbonyl-carbonyl, pyrrolidin-1-ylcarbonyl-carbonyl, benzyl-sulphonyl or phenyl-sulphonyl.

The following preferred compounds may be mentioned by way of example:
(1) [(3,5-dichloro-phenylsulphonyl)-(1-phenylcarbamoyl-1H-indol-5-yl)-amino]-acetic acid,
(2) [(3,5-dichloro-phenylsulphonyl)-(1-phenylcarbamoyl-2,3-dihydro-1H-indol-5-yl)-amino]-acetic acid,
(3) {(3,5-dichloro-phenylsulphonyl)-[1-(3-nitro-phenylcarbamoyl)-2,3-dihydro-1H-indol-5-yl]-amino}-acetic acid,
(4) {(3,5-dichloro-phenylsulphonyl)-[1-(pyridin-3-ylcarbamoyl)-2,3-dihydro-1H-indol-5-yl]-amino}-acetic acid,
(5) {(3,5-dichloro-phenylsulphonyl)-[1-(2-nitro-phenylcarbamoyl)-2,3-dihydro-1H-indol-5-yl]-amino}-acetic acid,
(6) [(1-acetyl-2,3-dihydro-1H-indol-5-yl)-(3,5-dichloro-phenylsulphonyl)-amino]-acetic acid,
(7) [(3,5-dichloro-phenylsulphonyl)-(1-methylcarbamoyl-2,3-dihydro-1H-indol-5-yl)-amino]-acetic acid,
(8) {(3,5-dichloro-phenylsulphonyl)-[1-(pyridin-4-ylcarbamoyl)-2,3-dihydro-1H-indol-5-yl]-amino}-acetic acid,
(9) [(2,6-dichloro-pyridine-4-sulphonyl)-(9-ethyl-9H-carbazol-3-yl)-amino]-acetic acid,
(10) {(3,5-dichloro-phenylsulphonyl)-[3-(morpholine-4-carbonyl)-1H-indol-6-yl]-amino}-acetic acid,
(11) [(3,5-dichloro-phenylsulphonyl)-(3-dimethylcarbamoyl-1-methyl-1H-indol-6-yl)-amino]-acetic acid,
(12) [(3,5-dichloro-phenylsulphonyl)-(3-methylcarbamoyl-benzo[b]thiophen-6-yl)-amino]-acetic acid,
(13) {(3,5-dichloro-phenylsulphonyl)-[1-methyl-3-(pyrrolidine-1-carbonyl)-1H-indol-6-yl]-amino}-acetic acid,
(14) [(3,5-dimethyl-phenylsulphonyl)-(1-methylcarbamoyl-2,3-dihydro-1H-indol-5-yl)-amino]-acetic acid,
(15) [[3-(azetidine-1-carbonyl)-1-methyl-1H-indol-6-yl]-(3,5-dichloro-phenylsulphonyl)-amino]-acetic acid,
(16) {(3,5-dichloro-phenylsulphonyl)-[3-(3-hydroxy-pyrrolidine-1-carbonyl)-1-methyl-1H-indol-6-yl]-amino}-acetic acid,
(17) [[3-(cyclopropyl-methyl-carbamoyl)-1-methyl-1H-indol-6-yl]-(3,5-dichloro-phenylsulphonyl)-amino]-acetic acid,
(18) {(3-chloro-5-methyl-phenylsulphonyl)-[1-methyl-3-(pyrrolidine-1-carbonyl)-1H-indol-6-yl]-amino}-acetic acid,
(19) {(3,5-dimethyl-phenylsulphonyl)-[1-methyl-3-(pyrrolidine-1-carbonyl)-1H-indol-6-yl]-amino}-acetic acid and
(20) [(3,5-dichloro-phenylsulphonyl)-(3-hydroxymethyl-1-methylcarbamoyl-2,3-dihydro-1H-indol-5-yl)-amino]-acetic acid, the enantiomers, the mixtures and the salts thereof.

Some terms used hereinbefore and hereinafter to describe the compounds according to the invention are defined more specifically below.

The term halogen denotes an atom selected from among F, Cl, Br and I, particularly F, Cl and Br.

The term $C_{1-n}$-alkyl, wherein n may have a value as defined hereinbefore or hereinafter, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkynyl, wherein n has a value as defined hereinbefore, denotes a branched or unbranched hydrocarbon group with 2 to n C atoms and a C≡C triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{2-n}$-alkenyl, wherein n has a value as defined hereinbefore, denotes a branched or unbranched hydrocarbon group with 2 to n C atoms and a C═C double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkyl-carbonyl denotes a $C_{1-n}$-alkyl-C(═O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbornyl, norcaryl, adamantyl, etc. Preferably the term $C_{3-7}$-cycloalkyl includes saturated monocyclic groups.

The term $C_{3-n}$-cycloalkyloxy or $C_{3-n}$-cycloalkoxy d a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{1-n}$-alkoxy-carbonyl denotes a $C_{1-n}$-alkyl-O—C(═O) group, wherein $C_{1-n}$-alkyl is as hereinbefore defined.

The term $C_{3-n}$-cycloalkyl-carbonyl denotes a $C_{3-n}$-cycloalkyl-C(═O) group, wherein $C_{3-n}$-cycloalkyl is as hereinbefore defined.

The terms $C_{1-n}$-alkyl-amino and di-($C_{1-n}$-alkyl)amino denote a $C_{1-n}$-alkyl-NH— or a di-($C_{1-n}$-alkyl)-N group, respectively, wherein $C_{1-n}$-alkyl is as hereinbefore defined.

The term $C_{3-n}$-cycloalkyl-amino denotes a $C_{3-n}$-cycloalkyl-NH group, wherein $C_{3-n}$-cycloalkyl is as hereinbefore defined.

The term N—($C_{3-n}$-cycloalkyl)-N—($C_{1-n}$-alkyl)amino denotes an N—($C_{3-n}$-cycloalkyl)-N—($C_{1-n}$-alkyl)-N group, wherein $C_{3-n}$-cycloalkyl and $C_{1-n}$-alkyl are as hereinbefore defined.

The terms $C_{1-n}$-alkyl-aminocarbonyl and di-($C_{1-n}$-alkyl) aminocarbonyl denote a $C_{1-n}$-alkyl-NH—C(═O)— or a di-($C_{1-n}$-alkyl)-N—C(═O) group, respectively, wherein $C_{1-n}$-alkyl is as hereinbefore defined.

The term $C_{3-n}$-cycloalkyl-aminocarbonyl denotes a $C_{3-n}$-cycloalkyl-NH—C(═O) group, wherein $C_{3-n}$-cycloalkyl is as hereinbefore defined.

The term N—($C_{3-n}$-cycloalkyl)-N—($C_{1-n}$-alkyl)amino denotes an N—($C_{3-n}$-cycloalkyl)-N—($C_{1-n}$-alkyl)-N—C(═O) group, wherein $C_{3-n}$-cycloalkyl and $C_{1-n}$-alkyl are as hereinbefore defined.

The terms di-($C_{1-n}$-alkyl)amino and di-($C_{1-n}$-alkyl)aminocarbonyl, wherein n has a value as defined hereinbefore, encompass amino groups which have the same or two different alkyl groups.

The term $C_{1-n}$-perfluoroalkyl denotes a F—$(CF2)_n$ group. Examples of such groups include trifluoromethyl, pentafluoroethyl, heptafluoro-n-propyl, heptafluoro-iso-propyl etc., but preferably trifluoromethyl, pentafluoroethyl.

The term $C_{1-n}$-perfluoroalkoxy denotes a F—$(CF2)_n$—O group. Examples of such groups include trifluoromethoxy, pentafluoroethoxy, heptafluoro-n-propoxy, heptafluoro-iso-propoxy etc., but preferably trifluoromethoxy, pentafluoroethoxy.

The term $C_{1-n}$-alkylsulphonyl denotes a $C_{1-n}$-alkyl-S$(=O)_2$ group, wherein $C_{1-n}$-alkyl is as hereinbefore defined.

The compounds according to the invention may be obtained using methods of synthesis that are known in principle. Preferably the compounds are obtained by methods of preparation according to the invention that are described more fully hereinafter.

The preparation of compounds of general formula I may be carried out according to Process a) according to the invention shown in Scheme 1, wherein X, Y, Z, $R^1$, $R^2$, $R^3$ and A are as hereinbefore defined, starting from a compound of general formula II.

Diagram 1: Process a

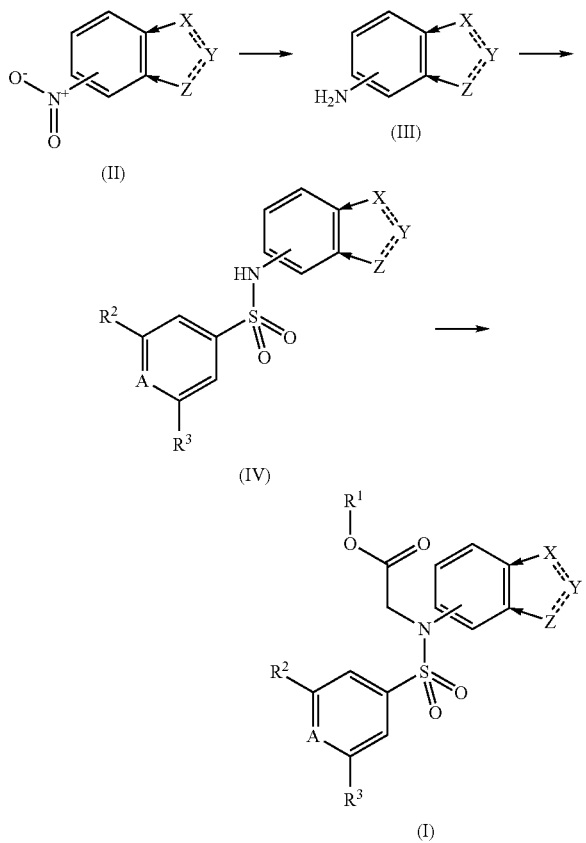

Here, compounds of general formula III are obtained by reacting a compound of general formula II with a reducing agent. The starting compounds of general formula II or III are either commercially obtainable or may be prepared by synthesising the heterocyclic group and/or nitrogenation (Houben-Weyl, *Methoden der organischen Chemie*, Volume X/1, 463-890) using methods known per se starting from commercially obtainable compounds.

A suitable reducing agent is for example hydrogen in the presence of a catalyst, such as palladium on charcoal, palladium hydroxide on charcoal or Raney nickel, while palladium on charcoal is particularly suitable. The hydrogenation is carried out in a suitable solvent such as methanol, ethanol, isopropanol, tetrahydrofuran, dichloromethane or ethyl acetate, but preferably methanol, ethanol or tetrahydrofuran, at a pressure between 0.5 and 7 bar, but preferably at a pressure between 0.5 and 3 bar, and at a temperature between 0° C. and 60° C., but preferably at a temperature between 15° C. and 40° C.

Also suitable for the reduction is tin dichloride hydrate in lower alcoholic solvents such as methanol or ethanol at a temperature between ambient temperature and 80° C.

Alternatively titanium trichloride may be used as reducing agent. Suitable solvents are mixtures of acetone and water. The reaction is carried out between 0° C. and 60° C., but preferably between 15° C. and 40° C. and in the presence of ammonium acetate.

Compounds of general formula IV are obtained by sulphonylation of compounds of general formula III.

The sulphonylation is carried out with aromatic sulphonyl chlorides in the presence of a base, such as triethylamine, N,N-diisopropyl-N-ethyl-amine, pyridine, or 4-dimethylamino-pyridine, but preferably pyridine. The reaction may be carried out in suitable solvents, such as diethyl ether, tetrahydrofuran, toluene, pyridine, dichloromethane, or chloroform, but preferably dichloromethane. The temperature may be between 0° C. and 60° C., but preferably between 15° C. and 40° C.

Compounds of general formula I are obtained from compounds of general formula IV by alkylation.

Suitable alkylating agents are acetic acid derivatives that contain a leaving group such as chlorine, bromine, iodine, p-tolylsulphonate, methylsulphonate, or trifluoromethylsulphonate in the 2-position. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, and at a temperature between 0° C. and 100° C., but preferably between 15° C. and 50° C.

If acetic acid derivatives with a tert.-butyl ester unit are used as alkylating agents, compounds of general formula I are obtained wherein $R^1$=tert.-butyl. The cleaving of the tert.-butyl group is preferably carried out by treatment with an acid such as trifluoroacetic acid or hydrochloric acid or by treatment with iodotrimethylsilane optionally using a solvent such as methylene chloride, dioxane, methanol or diethyl ether.

b) Compounds of general formula VI, wherein $R^4$ is bound to X and X denotes nitrogen, may be obtained by Process b) according to the invention shown in Scheme 2 from compounds of general formula V, wherein —Y . . . Z→has the meaning —CH=CH→, —$CH_2$—$CH_2$—→ or N=CH→, but preferably has the meaning —CH=CH→ or —$CH_2$—$CH_2$—→, while the carbon atoms therein may be substituted as hereinbefore defined and $R^4$ denotes an acyl, sulphonyl, alkoxy-carbonyl, substituted amino-carbonyl or optionally substituted alkyl group denotes and $R^5$ denotes the group R defined as hereinbefore, a nitro group or a group of formula

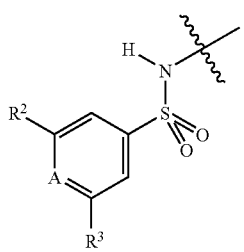

wherein R, $R^2$, $R^3$ and A are as hereinbefore defined.

Diagram 2: Process b

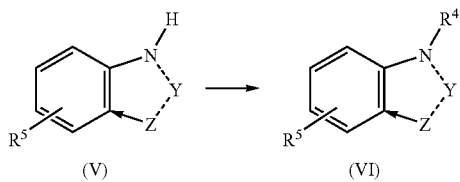

Acyl groups may be introduced by reacting a compound of general formula V with an acylating reagent such as for example an acid chloride or acid anhydride. The reaction may be carried out in the presence of a base such as sodium hydroxide, sodium hydride, sodium carbonate, potassium carbonate, caesium carbonate, triethylamine or N,N-diisopropyl-N-ethyl-amine as well as in a solvent such as dichloromethane, tetrahydrofuran, dioxane or dimethylformamide at temperatures between −30° C. and 200° C., but preferably between 0° C. and 160° C. Alternatively the reaction may be carried out by acylation with an acid. For this, the acid is activated in situ by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example N,N-dimethylformamide, dimethylacetamide, tetrahydrofuran, acetonitrile, N-methylpyrrolidone or dimethylsulphoxide, but preferably in N,N-dimethylformamide or N-methylpyrrolidone with a compound of general formula V in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Sulphonyl groups may be introduced by reacting with a sulphonyl chloride in the presence of a base such as for example sodium carbonate, potassium carbonate, caesium carbonate, triethylamine or N,N-diisopropyl-N-ethyl-amine, but preferably potassium carbonate, in a solvent such as dichloromethane, tetrahydrofuran, dioxane or N,N-dimethylformamide at temperatures between −30° C. and 100° C., but preferably between 0° C. and 60° C.

Alkoxycarbonyl groups may be introduced by reacting with an alkyl chloroformate in the presence of a base such as for example sodium carbonate, potassium carbonate, caesium carbonate, triethylamine or N,N-diisopropyl-N-ethyl-amine, but preferably potassium carbonate, in a solvent such as dichloromethane, tetrahydrofuran, dioxane or N,N-dimethylformamide at temperatures between −30° C. and 100° C., but preferably between 0° C. and 60° C. Alternatively, alkoxycarbonyl groups are obtained by reacting a compound of general formula V with phosgene in a solvent such as dichloromethane, tetrahydrofuran or dioxane in the presence of a base such as for example sodium carbonate, potassium carbonate, caesium carbonate, triethylamine or N,N-diisopropyl-N-ethyl-amine, but preferably triethylamine or N,N-diisopropyl-N-ethyl-amine, and subsequently treating with an alcohol at temperatures between −20° C. and 100° C., but preferably between 0° C. and 50° C.

Aminocarbonyl groups may be introduced by reacting with an isocyanate, optionally in the presence of a base such as for example sodium carbonate, potassium carbonate, caesium carbonate, triethylamine or N,N-diisopropyl-N-ethyl-amine in a solvent such as dichloromethane, tetrahydrofuran, dioxane or dimethylformamide at temperatures between −30° C. and 150° C., but preferably between 0° C. and 100° C. Alternatively aminocarbonyl groups are obtained by reacting a compound of general formula V with phosgene in a solvent such as dichloromethane, tetrahydrofuran or dioxane in the presence of a base such as for example sodium hydride, sodium carbonate, potassium carbonate, caesium carbonate, triethylamine or N,N-diisopropyl-N-ethyl-amine, but preferably sodium hydride, triethylamine or N,N-diisopropyl-N-ethyl-amine and subsequently treating with an amine at temperatures between −20° C. and 100° C., but preferably between 0° C. and 50° C.

In order to introduce alkyl groups the compounds of general formula V are reacted with a base such as for example sodium hydride, potassium hydride, sodium amide, lithium diisopropylamide, lithium hexamethyldisilazide, potassium hexamethyldisilazide or sodium hexamethyldisilazide and an alkylating agent. The reaction is carried out in a solvent such as for example tetrahydrofuran, 1,4-dioxane, dimethylformamide, dimethylacetamide, N-methylpyrrolidone or acetonitrile at temperatures between −40° C. and 120° C., but preferably between −10° C. and 100° C.

The compounds of general formula VI thus obtained correspond to intermediates from Scheme 1 and may be converted into the end compounds of general formula I according to Process a).

c) Compounds of general formula VIII, wherein $R^4$ is bound to X and X denotes a carbon atom or CH, may be obtained according to Process c) according to the invention shown in Scheme 3 from compounds of general formula VII wherein . . . Y . . . Z→denotes =CH—N(H)→, =CH—N(Me)→, =N—N(Me)→ or =CH—S→, while the carbon atoms therein may be substituted as hereinbefore defined and $R^4$ denotes an optionally substituted amino-carbonyl or an alkoxy-carbonyl group and $R^6$ denotes nitro or

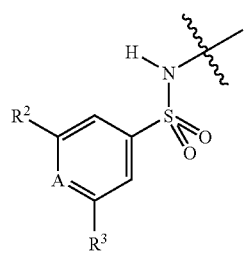

wherein $R^2$, $R^3$ and A are as hereinbefore defined.

Scheme 3: Process c

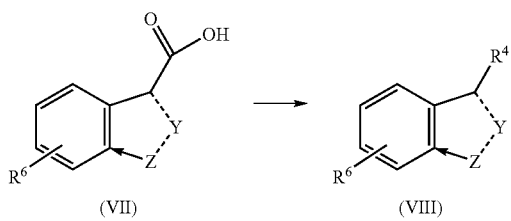

The transformation may be carried out by first converting the acid into an acid chloride. For this, a compound of general formula VII is combined with thionyl chloride, optionally in the presence of a solvent such as toluene or benzene heating it to temperatures between 50° C. and 150° C., but preferably between 80° C. and 120° C. After the elimination of the volatile constituents the acid chloride thus obtained is reacted with the alcohol or amine in a solvent such as dichloromethane, tetrahydrofuran, dioxane or dimethylformamide, but preferably tetrahydrofuran at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine. Alternatively the acid may be converted into an acid imidazolide. For this a compound of general formula VII is reacted with carbonyldiimidazole in a solvent such as dichloromethane, tetrahydrofuran or dioxane at temperatures between 20° C. and 100° C. The acid imidazolide thus obtained is reacted with the alcohol or amine in a solvent such as dichloromethane, tetrahydrofuran, dioxane or dimethylformamide, but preferably tetrahydrofuran, at temperatures between −30° C. and 150° C., but preferably between 0° C. and 80° C., and optionally in the presence of a base such as triethylamine, N,N-diisopropyl-N-ethyl-amine and optionally in the presence of a catalyst such as 4-N,N-dimethylaminopyridine.

Moreover, compounds of general formula VIII may be prepared by in situ activation of the carboxylic acid. For this, the acid is activated by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example dimethylformamide, dimethylacetamide, tetrahydrofuran, acetonitrile, N-methylpyrrolidone or dimethylsulphoxide, but preferably in dimethylformamide or N-methylpyrrolidone, with an alcohol or an amine in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Compounds of general formula VIII wherein $R^4$ denotes alkoxy-carbonyl may also be prepared by alkylating carboxylic acids of general formula VII. For this, the carboxylic acid is reacted with an alkylating agent. Suitable alkylating agents are alkyl derivatives that contain a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, at a temperature between 0° C. and 100° C., but preferably between 15° C. and 50° C.

The compounds of general formula VIII thus obtained correspond to inter-mediates from Scheme 1 and may be converted into the end compounds of general formula I according to Process a).

d) Compounds of general formula III, wherein Y and Z are as hereinbefore defined and X denotes a group of formula —C($R^4$)=, wherein $R^4$ is an alkylcarbonyl or arylcarbonyl group optionally substituted as mentioned hereinbefore, may be obtained by Process d) from compounds of general formula III, wherein Y and Z are as hereinbefore defined and X denotes a group of formula —CH=.

For this a compound of general formula III, wherein Y and Z are as hereinbefore defined and X denotes a group of formula —CH=, is reacted with an acid chloride or an acid anhydride, but preferably an acid anhydride. The reaction may be carried out without a solvent or with a solvent such as for example dichloromethane, 1,2-dichloroethane, toluene, tetrahydrofuran, 1,4-dioxane, dimethylformamide, dimethylacetamide or N-methyl-pyrrolidone and optionally in the presence of a catalyst such as for example aluminum trichloride or boron trifluoride etherate and at temperatures between −10° C. and 180° C., but preferably between 0° C. and 120° C.

The compounds thus obtained correspond to intermediates from Scheme 1 and may be converted into the end compounds of general formula I according to Process a).

e) Compounds of general formula III, wherein Y and Z are as hereinbefore defined and X denotes a group of formula —C($R^4$)=, wherein $R^4$ denotes an aminocarbonyl or alkoxycarbonyl group optionally substituted as mentioned hereinbefore, may be obtained by Process e) from compounds of general formula III, wherein Y and Z are as hereinbefore defined and X denotes a group of formula —C(CF$_3$)=.

The compounds of general formula III, wherein Y and Z are as hereinbefore defined and X denotes a group of formula —C(CF$_3$)=, are reacted with 5 to 50%, but preferably 40% sodium hydroxide solution or potassium hydroxide solution at temperatures between 0° C. and 200° C., but preferably between ambient temperature and 150° C. The carboxylic acids of general formula III thus obtained, wherein Y and Z are as hereinbefore defined and X denotes a group of formula —C(COOH)=, may for example be converted into an acid chloride.

For this the carboxylic acid obtained as described hereinbefore may be combined with thionyl chloride, optionally in the presence of a solvent such as toluene or benzene, and heated to temperatures between 50° C. and 150° C., but preferably between 80° C. and 120° C. After elimination of the volatile constituents the acid chloride thus obtained is reacted with the alcohol or amine in a solvent such as dichloromethane, tetrahydrofuran, dioxane or dimethylformamide, but preferably tetrahydrofuran at temperatures between −30° C. and 150° C., but preferably between 0° C. and 80° C. and optionally in the presence of a base such as triethylamine, N,N-diisopropyl-N-ethyl-amine and optionally in the presence of a catalyst such as 4-N,N-dimethylaminopyridine. Alternatively the acid may be converted into an acid imidazolide. For this a compound of general formula III, wherein Y and Z are as hereinbefore defined and X denotes a group of formula —C(COOH)= is reacted with carbonyldiimidazole in a solvent such as dichloromethane, tetrahydrofuran or dioxane at temperatures between 20° C. and 100° C. The acid imidazolide thus obtained is reacted with the alcohol or amine in a solvent such as dichloromethane, tetrahydrofuran, dioxane or dimethylformamide, but preferably tetrahydrofuran, at temperatures between −30° C. and 150° C., but preferably between 0° C. and 80° C., and optionally in the presence of a base such as triethylamine, N,N-diisopropyl-N-ethylamine and optionally in the presence of a catalyst such as 4-N,N-dimethylaminopyridine.

Moreover, compounds of general formula III, wherein Y and Z are as hereinbefore defined and X denotes a group of formula —C($R^4$)=, where $R^4$ denotes an aminocarbonyl or alkoxycarbonyl group optionally substituted as mentioned hereinbefore, are prepared by in situ activation of the carboxylic acid. For this the acid is activated by the addition of diisopropylcarbodiimide, dicyclohexylcarbodiimide, N-(3-dimethylaminopropyl)-N'-ethyl-carbodiimide, O-(benzotriazol-1-yl)-N,N,N',N'-tetramethyluronium-tetrafluoroborate (TBTU), O-(benzotriazol-1-yl)-N,N,N',N'-tetramethyluronium-hexafluorophosphate (HBTU), O-(7-azabenzotriazol-1-yl)-N,N,N',N'-tetramethyluronium-hexafluorophosphate (HATU), (benzotriazol-1-yloxy)-tris-(dimethylamino)-phosphonium-hexafluorophosphate (BOP), (benzotriazol-1-yloxy)-tripyrrolidinophosphonium-hexafluorophosphate (PyBOP) and reacted in a dipolar aprotic solvent such as for example dimethylformamide, dimethylacetamide, tetrahydrofuran, acetonitrile, N-methylpyrrolidone or dimethylsulphoxide, but preferably in dimethylformamide or N-methylpyrrolidone, with an alcohol or amine in the presence of a base such as triethylamine, N,N-diisopropyl-N-ethyl-amine and optionally a catalyst such as 4-N,N-dimethylaminopyridine at temperatures between −20° C. and 80° C., but preferably between 0° C. and 50° C.

Compounds of general formula III, wherein Y and Z are as hereinbefore defined and X denotes a group of formula —C($R^4$)=, where $R^4$ denotes an alkoxycarbonyl group optionally substituted as mentioned hereinbefore, may also be prepared by alkylation of carboxylic acids of general formula VII. For this the carboxylic acid is reacted with an alkylating agent. Suitable alkylating agents are alkyl derivatives that contain a leaving group such as chlorine, bromine, iodine, p-tolylsulphonate, methylsulphonate or trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, at a temperature between 0° C. and 100° C., but preferably between 15° C. and 50° C.

The compounds thus obtained correspond to intermediates from Scheme 1 and may be converted into the end compounds of general formula I according to Process a).

Compounds of general formula X wherein X and Y are defined as stated hereinafter and $R^4$ denotes an aminocarbonyl-carbonyl group, may be obtained by Process f) shown in Scheme 4 from compounds of general formula IX wherein . . . Y . . . Z→ has the meaning =CH—N(H)→, =CH—N(Me)→, =N—N(Me)→ or =CH—S→ where the carbon atoms therein may be substituted as hereinbefore defined, and R denotes nitro or

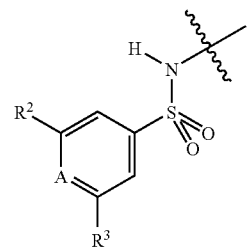

wherein $R^2$, $R^3$ and A are as hereinbefore defined.

Diagram 4: Process f

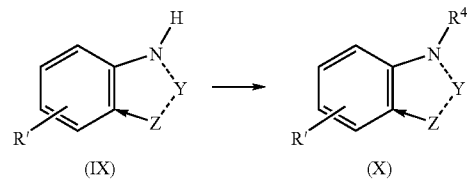

In this, compounds of general formula IX are converted into the chloro-carbonyl-carbonyl derivatives by reaction with oxalyl chloride in a solvent such as dichloromethane, diethyl ether, tetrahydrofuran, dioxane or toluene, but preferably diethyl ether, at temperatures between −20° C. and 80° C., but preferably between 0° C. and 50° C. After elimination of the volatile constituents they are reacted with an amine in a solvent such as dichloromethane, tetrahydrofuran, dioxane or dimethylformamide, but preferably tetrahydrofuran, at temperatures between −30° C. and 70° C., but preferably between 0° C. and 50° C. and optionally in the presence of a base such as triethylamine, N,N-diisopropyl-N-ethyl-amine and optionally in the presence of a catalyst such as 4-N,N-dimethylaminopyridine to form the compounds of general formula X.

The compounds of general formula X thus obtained correspond to intermediates from Scheme 1 and may be converted according to Process a) into the end compounds of general formula I.

Cyano functionalities may in each case be prepared from primary amides obtained in the syntheses. Suitable methods for this transformation are, for example, reaction with thionyl chloride and optionally catalytic amounts of dimethylformamide in a solvent such as dichloromethane, 1,2-dichloroethane, toluene or acetone at temperatures between 0° C. and 100° C., reaction with trifluoroacetic anhydride or trichloroacetic anhydride, a base such as for example pyridine, triethylamine or N,N-diisopropyl-N-ethyl-amine in a solvent such as for example dichloromethane, 1,2-dichloroethane, tetrahydrofuran, 1,4-dioxane or toluene at temperatures between −10° C. and 100° C., as well as reaction with phosphorus oxychloride and optionally a base such as pyridine or N,N-dimethylaniline in the presence or absence of a solvent such as for example dichloromethane, 1,2-dichloroethane, tetrahydrofuran, 1,4-dioxane or toluene, at temperatures between −10° C. and 120° C.

Sulphonyl chlorides may be prepared from anilines. For this, the aniline is first diazotized by reacting with sodium nitrite in hydrochloric acid at temperatures between −30° C. and 10° C. The diazonium salt solution thus prepared is then added dropwise to copper-II-chloride and water in a 30% sulphur dioxide solution in glacial acetic acid at temperatures between −30° C. and 10° C. Then it is left to warm up to temperatures between 5° C. and 50° C. Alternatively the sulphonyl chlorides may be prepared from aryl metal compounds such as aryl lithium or aryl magnesium chloride compounds. Aryl lithium compounds are obtained from the aryl bromides or aryl iodides by reacting with n-butyllithium, sec-butyllithium or tert.-butyllithium in a solvent such as diethyl ether or tetrahydrofuran at temperatures between −60° C. and −85° C. Arylmagnesium chloride compounds are obtained by a process as described in *Angew. Chem.* 2006, 118, 3024-3027. The aryl metal compounds thus obtained are further reacted at temperatures between −78° C. and −20° C. by piping sulphur dioxide through. This produces metal sulphinates, which can optionally be precipitated by the addition of hexane. The metal sulphinates are dissolved in dichloromethane and combined with N-chlorosuccinimide at temperatures between −20° C. and 30° C. After the reaction the solid is filtered off, to obtain a dichloromethane solution of the sulphonyl chloride.

In the reactions described hereinbefore, any reactive groups present such as carboxy, hydroxy, amino or alkylamino groups may be protected during the reaction by conventional protecting groups which are cleaved again after the reaction.

For example, a protecting group for a carboxy group may be a methyl, ethyl, tert.butyl or benzyl group.

For example, a protecting group for a hydroxy group may be an acetyl, benzyl or tetrahydropyranyl group.

Protecting groups for an amino or alkylamino may be a formyl, acetyl, trifluoroacetyl, ethoxycarbonyl, tert.butoxycarbonyl, benzyloxycarbonyl, benzyl, methoxybenzyl or 2,4-dimethoxybenzyl group.

A carboxymethyl or carboxyethyl unit is cleaved for example by hydrolysis in an aqueous solvent, e.g. In water, methanol/water, isopropanol/water, acetic acid/water, tetrahydrofuran/water or dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. In the presence of iodotrimethylsilane, at temperatures between 0 and 120° C., preferably at temperatures between 10 and 100° C.

A benzyl, methoxybenzyl or benzyloxycarbonyl group is advantageously cleaved by hydrogenolysis, e.g. with hydrogen in the presence of a catalyst such as palladium on charcoal in a suitable solvent such as methanol, ethanol, ethyl acetate or glacial acetic acid, optionally with the addition of an acid such as hydrochloric acid, at temperatures between 0 and 100° C., but preferably at temperatures between 20 and 60° C., and under a hydrogen pressure of 1 to 7 bar, but preferably 1 to 3 bar. However, a 2,4-dimethoxy-benzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

Moreover, the compounds of general formula I obtained, or intermediate products from the synthesis of compounds of general formula I, as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, the cis/trans mixtures may be resolved by chromatography into the cis and trans isomers thereof, the compounds of general formula I obtained, or intermediate products from the synthesis of compounds of general formula I, which occur as racemates may be separated by methods known per se (cf. Allinger N. L. And Eliel E. L. In "Topics in Stereochemistry", Vol. 6, Wiley Interscience, 1971) into their optical antipodes and compounds of general formula I, or intermediate products from the synthesis of compounds of general formula I, with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. Esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. The D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-methyloxycarbonyl.

Furthermore, the compounds of formula I obtained, or intermediate products from the synthesis of compounds of general formula I, may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of general formula I obtained, or intermediate products from the synthesis of compounds of general formula I, if they contain a carboxy group, may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formula I are inhibitors of the interaction between human liver glycogen phosphorylase (HLGP) and protein PPP1R3 ($G_L$-subunit of glycogen-associated protein phosphatase 1 (PP1)). The effect of the compounds on the binding of the protein PPP1R3 and the glycogen phosphorylase activated by phosphorylation is determined in a binding test based on SPA technology (Amersham Pharmacia). The binding of the substances inhibits the interaction of the glycogen phosphorylase with the protein PPP1R3B. All measurements were made in triplicate in the 384-well format (Optiplate, Perkin Elmer).

Human glycogen phosphorylase is recombinantly expressed in *E. Coli* and purified. The isolated non-phosphorylated HLGP is radioactively labelled in a marking reaction with phosphorylase kinase (200-500 U/mg, P2014, Sigma) and $^{33}$P-gamma ATP (110 TBq/mmol, Hartmann Analytic) (Ref.: Cohen et al., Methods Enzymol. 1988, Vol 159 pp 390).

In a binding test, in a volume of 100 μl (test buffer: 50 mM Tris/HCl pH 7.0, 0.1 mM EGTA, 0.1% mercapto-ethanol), different amounts of a test substance (final concentration: 1 nM to 30 μM) are incubated at ambient temperature for 16 hours with 100000 cpm of labelled HLGP, 375 μg streptavidin-SPA Beads (RPNQ 0007, Amersham Pharmacia), 0.1 μg GL-peptide (Biotin-FPEWPSYLGYEKLGPYY). After centrifuging for 5 minutes at 500 g the plate is measured (Topcount, Packard). The cpm values measured are used to calculate the $IC_{50}$ values specified. The basal value is determined in the absence of the peptide and the maximum value is determined in the absence of the test substance.

The compounds of general formula I have $IC_{50}$ values in the range from 100 nM to 15 μM.

In view of their ability to suppress the interaction of glycogen phosphorylase a with the GL-subunit of glycogen-associated protein phosphatase 1 (PP1), the compounds of general formula I according to the invention and the corresponding pharmaceutically acceptable salts thereof are theoretically suitable for treating and/or preventatively treating all those conditions or diseases that can be influenced by inhibiting the interaction of glycogen phosphorylase a with the GL-subunit of glycogen-associated protein phosphatase 1 (PP1). Therefore the compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. Apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 0.1 to 1000 mg, preferably 0.5 to 500 mg, by intravenous route, and 1 to 1000 mg, preferably 10 to 500 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include in particular those which potentiate the therapeutic effect of an inhibitor of the interaction of glycogen phosphorylase a with the $G_L$ subunit of glycogen-associated protein phosphatase 1 (PP1) according to the invention with respect to one of the indications mentioned and/or which allow the dosage of an an inhibitor of the interaction of glycogen phosphorylase a with the GL subunit of glycogen-associated protein phosphatase 1 (PP1) according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. miglitol, acarbose, voglibose), DPPIV inhibitors (e.g. sitagliptine, vildagliptine), SGLT2-inhibitors, alpha2-antagonists, insulin and insulin analogues, GLP-1 and GLP-1 analogues (e.g. Exendin-4) or amylin. Other active substances suitable as combination partners are inhibitors of protein tyrosinephosphatase 1, substances that affect deregulated glucose production in the liver, such as e.g. Inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. Avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the interaction of glycogen phosphorylase a with the $G_L$ subunit of glycogen-associated protein phosphatase 1 (PP1).

These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of oxygen and nitrogen atoms are not explicitly shown in every case in structural formulae. The Examples that follow are intended to illustrate the present invention without restricting it:

Preparation of the Starting Compounds

EXAMPLE I

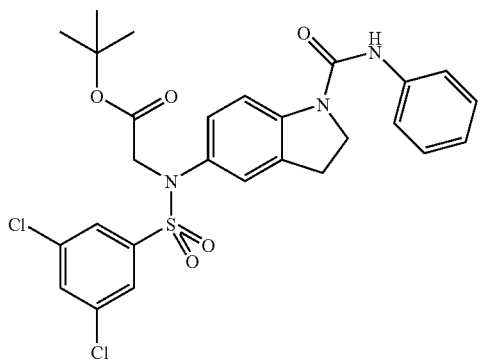

tert.butyl [(3,5-dichloro-phenylsulphonyl)-(1-phenyl-carbamoyl-2,3-dihydro-1H-indol-5-yl)-amino]-acetate 990 mg tert.butyl [(3,5-dichloro-phenylsulphonyl)-(2,3-dihydro-1H-indol-5-yl)-amino]-acetate are dissolved in 10 ml dichloromethane. 598 mg potassium carbonate and 247 μl phenylisocyanate are added. After stirring overnight the solid is filtered off and washed twice with dichloromethane. The combined organic phases are evaporated down in vacuo and the residue is purified by chromatography on silica gel (cyclohexane/ethyl acetate 10:1 to 1:2).

Yield: 1.24 g (99% of theory)

Mass spectrum (ESI+): m/z=576 [M+H]+

The following compounds are obtained analogously to Example I:

(1) tert.butyl [(1-benzylcarbamoyl-2,3-dihydro-1H-indol-5-yl)-(3,5-dichloro-phenylsulphonyl)-amino]-acetate

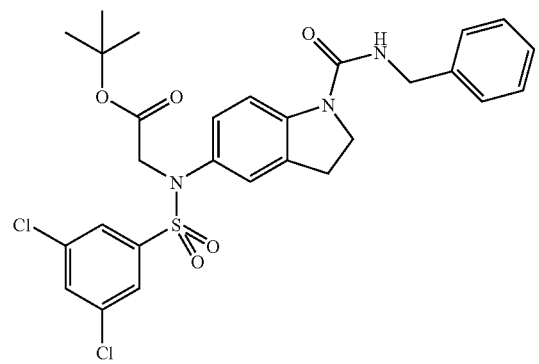

Carried out without potassium carbonate for 3 hours.

Mass spectrum (ESI+): m/z=589 [M+H]+

(2) tert.butyl {(3,5-dichloro-phenylsulphonyl)-[1-(3-nitro-phenylcarbamoyl)-2,3-dihydro-1H-indol-5-yl]-amino}-acetate

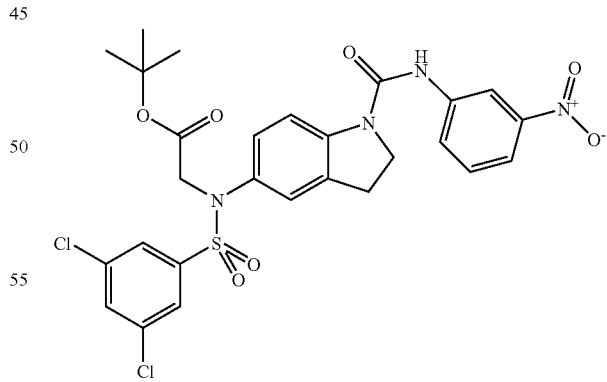

Carried out for 3 hours. Then the mixture is divided between water and ethyl acetate. The aqueous phase is extracted with ethyl acetate. The combined organic phases are dried on sodium sulphate, the solvents are eliminated in vacuo, and the residue is extracted from diisopropylether.

Mass spectrum (ESI+): m/z=621 [M+H]+

(3) tert.butyl {(3,5-dichloro-phenylsulphonyl)-[1-(2-nitro-phenylcarbamoyl)-2,3-dihydro-1H-indol-5-yl]-amino}-acetate

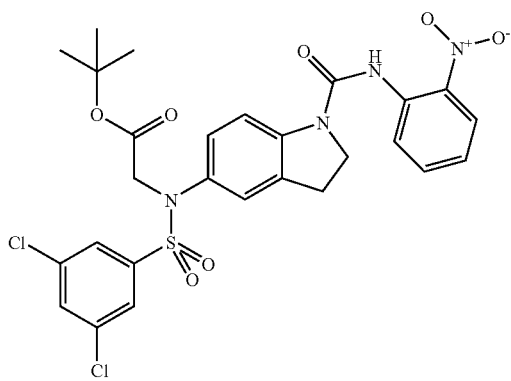

Carried out for 3 hours. The mixture is diluted with ethyl acetate and washed successively with dilute citric acid solution and saturated sodium chloride solution. After drying with magnesium sulphate the solvents are eliminated in vacuo and the residue is extracted from diethyl ether. The solid is filtered off. The mother liquor is evaporated down in vacuo, and the residue is purified by chromatography on silica gel.

Mass spectrum (ESI$^+$): m/z=621 [M+H]$^+$ (4) tert.butyl {(3,5-dichloro-phenylsulphonyl)-[1-(pyridin-3-ylcarbamoyl)-2,3-dihydro-1H-indol-5-yl]-amino}-acetate

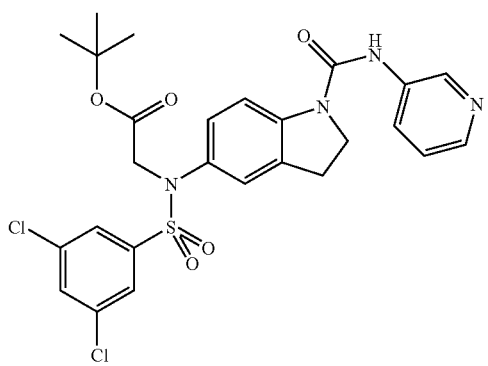

Carried out for 3 hours. The mixture is diluted with ethyl acetate and washed successively with dilute citric acid solution and saturated sodium chloride solution. After drying with magnesium sulphate the solvents are eliminated in vacuo.

Mass spectrum (ESI$^+$): m/z=577 [M+H]$^+$ (5) 4-nitro-2,3-dihydro-indole-1-carboxylic acid-phenylamide

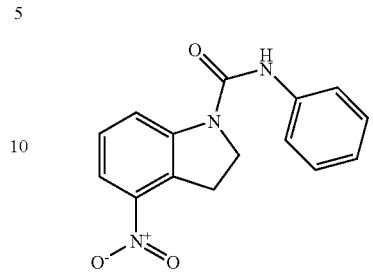

After the reaction the mixture is diluted with dichloromethane and washed twice with saturated sodium chloride solution. Then it is dried on magnesium sulphate, the solvents are eliminated in vacuo and the residue is extracted from diisopropylether.

Mass spectrum (ESI$^+$): m/z=284 [M+H]$^+$ (6) 4-nitro-2,3-dihydro-indole-1-carboxylic acid-pyridin-3-ylamide

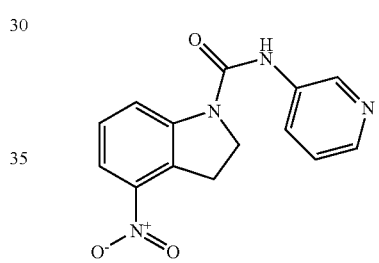

After the reaction the mixture is diluted with dichloromethane and washed twice with saturated sodium chloride solution. Then it is dried on magnesium sulphate and the solvent is eliminated in vacuo.

Mass spectrum (ESI$^+$): m/z=285 [M+H]$^+$ (7) 6-nitro-2,3-dihydro-indole-1-carboxylic acid-phenylamide

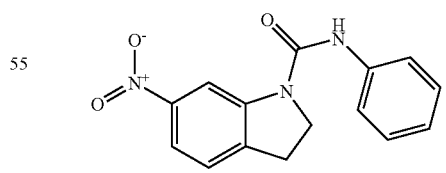

After the reaction the mixture is diluted with dichloromethane and washed with semi-saturated sodium chloride solution. Then it is dried on magnesium sulphate and the solvent is eliminated in vacuo. The residue is chromatographed on silica gel.

Mass spectrum (ESI$^+$): m/z=284 [M+H]$^+$

EXAMPLE II

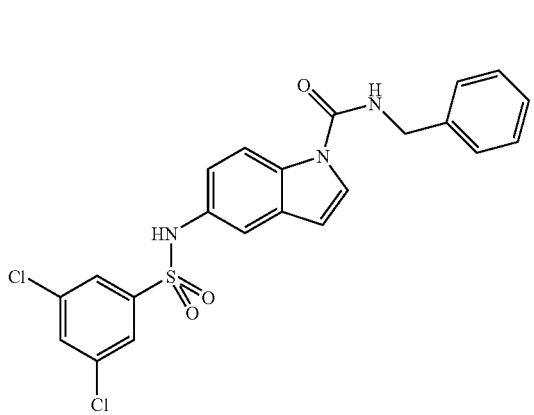

5-(3,5-dichloro-phenylsulphonylamino)-indole-1-carboxylic acid-benzylamide 130 mg 3,5-dichloro-N-(1H-indol-5-yl)-phenylsulphonamide are dissolved in 5 ml dichloromethane and 14 mg dimethylaminopyridine and 56 μl benzylisocyanate are added. The mixture is stirred overnight at ambient temperature, divided between 1 N HCl and ethyl acetate, the aqueous phase is extracted with ethyl acetate and the combined organic phases are dried with magnesium sulphate. The solvents are eliminated in vacuo and the residue is chromatographed on silica gel (cyclohexane/ethyl acetate 10:1 to 1:3).

Yield: 152 mg (84% of theory)

Mass spectrum (ESI$^+$): m/z=474 [M+H]$^+$

The following compounds are obtained analogously to Example II:

(1) 4-(3,5-dichloro-phenylsulphonylamino)-indole-1-carboxylic acid-benzylamide

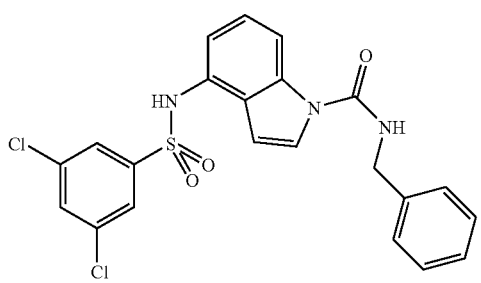

Mass spectrum (ESI$^+$): m/z=474 [M+H]$^+$

EXAMPLE III

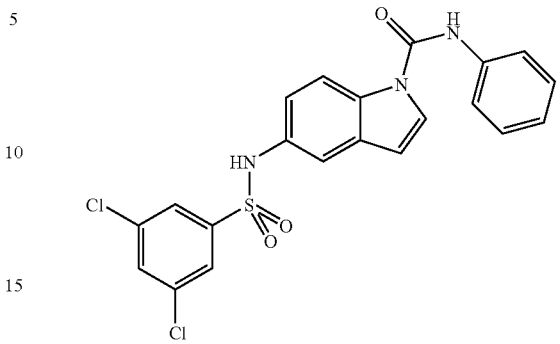

5-(3,5-dichloro-phenylsulphonylamino)-indole-1-carboxylic acid-phenylamide 100 mg 3,5-dichloro-N-(1H-indol-5-yl)-phenylsulphonamide are dissolved in 3 ml dimethylformamide. 38 μl phenylisocyanate and 10 dimethylaminopyridine are added and the mixture is heated to 80° C. for 5 minutes in the microwave. Then another 30 μl phenylisocyanate are added and the mixture is heated to 100° C. for 15 minutes in the microwave. The solvent is then eliminated in vacuo and the residue is chromatographed on silica gel (cyclohexane/ethyl acetate 10:1 to 1:3).

Yield: 124 mg (the product also contains 3,5-dichloro-N-(1H-indol-5-yl)-phenylsulphonamide and diphenylurea)

Mass spectrum (ESI$^-$): m/z=458 [M−H]$^-$

EXAMPLE IV

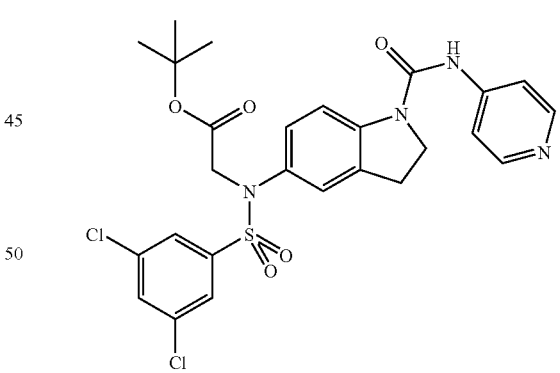

tert.butyl {(3,5-dichloro-phenylsulphonyl)-[1-(pyridin-4-ylcarbamoyl)-2,3-dihydro-1H-indol-5-yl]-amino}-acetate 215 mg tert.butyl [(3,5-dichloro-phenylsulphonyl)-(2,3-dihydro-1H-indol-5-yl)-amino]-acetate are dissolved in 10 ml dichloromethane. For this 75 μl diisopropylethylamine and 1 ml of a 20% solution of phosgene in toluene are added. The mixture is stirred for another 2 hours and then the solvents are eliminated in a nitrogen current. The residue is taken up in 10 ml of tetrahydrofuran. To this is added a solution prepared by the addition of 75 mg 4-aminopyridine to a solution of 30 mg sodium hydride (60% suspension in mineral oil) in 10 ml of tetrahydrofuran and 30 minutes' stirring. The mixture is stirred overnight at ambient temperature and then refluxed for 24 hours. The solvents are eliminated in vacuo and the residue is purified by chromatography on silica gel (cyclohexane/ethyl acetate 10:1 to 1:3).

Yield: 190 mg (70% of theory)

Mass spectrum (ESI$^+$): m/z=577 [M+H]$^+$

The following compounds are obtained analogously to Example IV:

(1) tert.butyl {(3,5-dichloro-phenylsulphonyl)-[1-(pyrazin-2-ylcarbamoyl)-2,3-dihydro-1H-indol-5-yl]-amino}-acetate

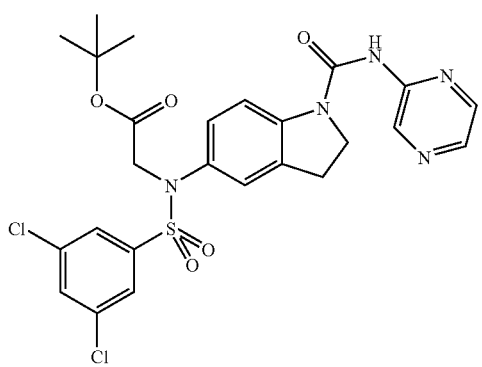

Carried out for 2 hours at ambient temperature.
Mass spectrum (ESI$^+$): m/z=578 [M+H]$^+$

EXAMPLE V

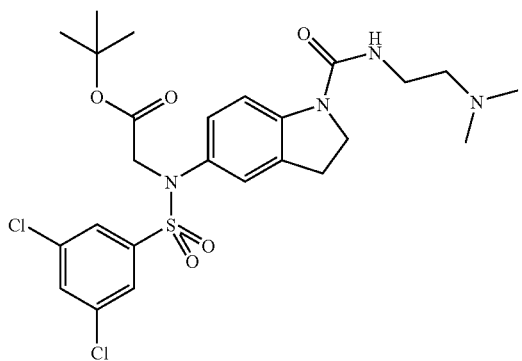

tert.butyl {(3,5-dichloro-phenylsulphonyl)-[1-(2-dimethylamino-ethylcarbamoyl)-2,3-dihydro-1H-indol-5-yl]-amino}-acetate 800 μl of a 20% solution of phosgene in toluene are dissolved in 10 ml dichloromethane and cooled to 0° C. To this are added 35 μl diisopropylethylamine and 100 mg tert.butyl [(3,5-dichloro-phenylsulphonyl)-(2,3-dihydro-1H-indol-5-yl)-amino]-acetate. The mixture is stirred for a further 1 hour and then the solvents are eliminated in a nitrogen current. The residue is taken up in 10 ml of tetrahydrofuran, 200 μl N,N-dimethylethylenediamine are added and the mixture is stirred for 3 hours at ambient temperature. Then it is diluted with ethyl acetate and washed with semi-saturated sodium chloride solution. The organic phase is dried on magnesium sulphate, the solvents are eliminated in vacuo and the residue is purified by chromatography on aluminum oxide (cyclohexane/ethyl acetate 3:7 to ethyl acetate).

Yield: 75 mg (60% of theory)

Mass spectrum (ESI$^+$): m/z=571 [M+H]$^+$

The following compounds are obtained analogously to Example V:

(1) tert.butyl [(3,5-dichloro-phenylsulphonyl)-(1-dimethylcarbamoyl-2,3-dihydro-1H-indol-5-yl)-amino]-acetate

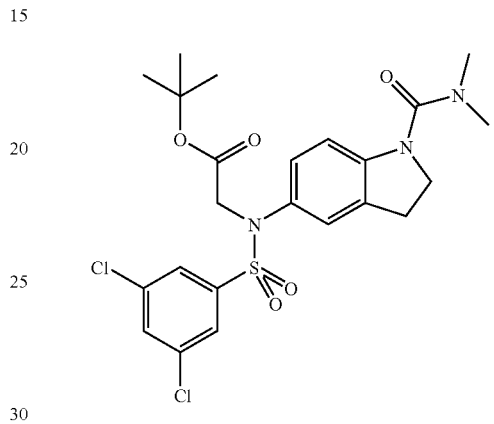

Carried out for 3 hours at 60° C.
Mass spectrum (ESI$^+$): m/z=528 [M+H]$^+$ (2) methyl 5-[tert-butoxycarbonylmethyl-(3,5-dichloro-phenylsulphonyl)-amino]-2,3-dihydro-indole-1-carboxylate

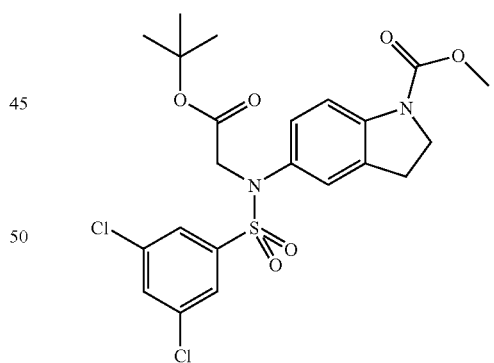

4-Pyridylamine is used instead of N,N-dimethylethylenediamine. Carried out overnight at ambient temperature. Then the solvents are eliminated in vacuo, the residue is taken up in methanol and purified by chromatography on silica gel. It is not the desired product 5-[tert-butoxycarbonylmethyl-(3,5-dichloro-phenylsulphonyl)-amino]-2,3-dihydro-indole-1-carboxylic acid-pyridin-3-ylamide, but methyl 5-[tert-butoxycarbonylmethyl-(3,5-dichloro-phenylsulphonyl)-amino]-2,3-dihydro-indole-1-carboxylate that is isolated.

Mass spectrum (ESI$^+$): m/z=532 [M+NH$_4$]$^+$ (3) 5-nitro-2,3-dihydro-indole-1-carboxylic acid-methylamide

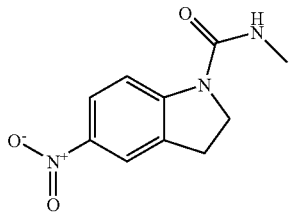

The crude product is extracted from 1 N HCl.
Mass spectrum (ESI⁺): m/z=222 [M+H]⁺

(4) 4-nitro-2,3-dihydro-indole-1-carboxylic acid-methylamide

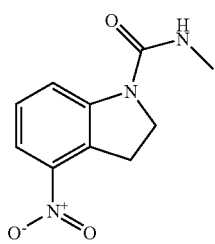

Mass spectrum (ESI⁺): m/z=222 [M+H]⁺

(5) tert.butyl {(3,5-dichloro-phenylsulphonyl)-[1-(3-oxo-piperazin-1-carbonyl)-2,3-dihydro-1H-indol-5-yl]-amino}-acetate

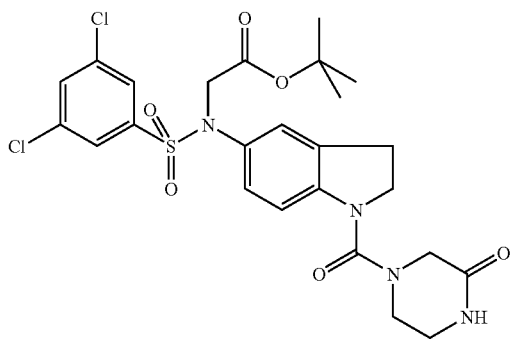

Mass spectrum (ESI⁺): m/z=600 [M+NH₄]⁺

(6) tert.butyl {(3,5-dichloro-phenylsulphonyl)-[1-(1-methylcarbamoyl-ethylcarbamoyl)-2,3-dihydro-1H-indol-5-yl]-amino}-acetate

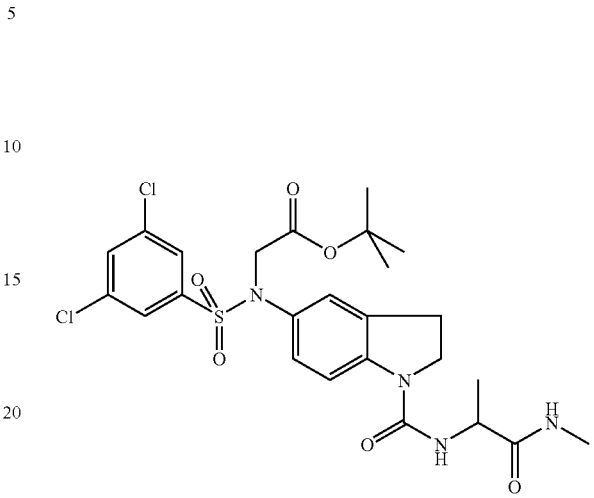

Mass spectrum (ESI⁺): m/z=585 [M+H]⁺

(7) methyl 5-(3,5-dichloro-phenylsulphonylamino)-1-methylcarbamoyl-2,3-dihydro-1H-indole-3-carboxylate

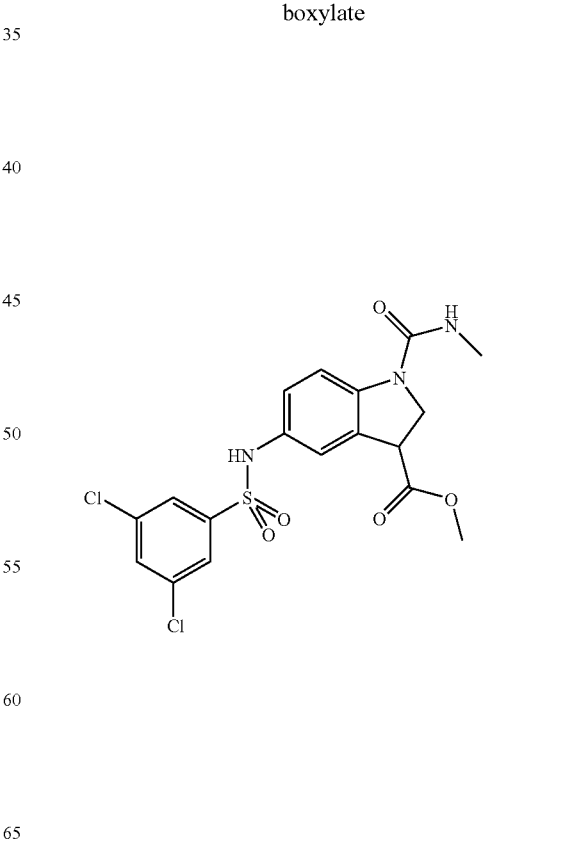

Mass spectrum (ESI⁺): m/z=458 [M+H]⁺

(8) tert.butyl {(3,5-dichloro-phenylsulphonyl)-[1-(2-methylcarbamoyl-pyrrolidine-1-carbonyl)-2,3-dihydro-1H-indol-5-yl]-amino}-acetate

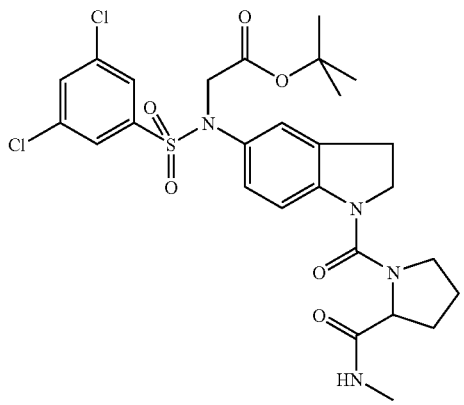

Mass spectrum (ESI+): m/z=611 [M+H]+

EXAMPLE VI

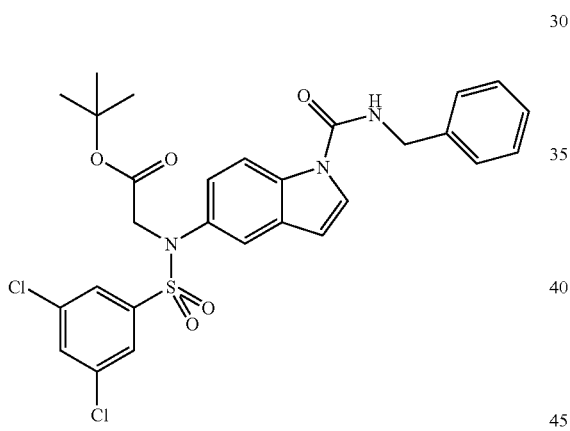

tert.butyl [(1-benzylcarbamoyl-1H-indol-5-yl)-(3,5-dichloro-phenylsulphonyl)-amino]-acetate 150 mg 5-(3,5-dichloro-phenylsulphonylamino)-indole-1-carboxylic acid-benzylamide are dissolved in 5 ml dimethyl-formamide. 109 mg potassium carbonate and 51 μl tert.butyl bromoacetate are added thereto. The mixture is stirred for 4 hours at ambient temperature, the solvent is eliminated in vacuo and the residue is divided between water and ethyl acetate. The aqueous phase is extracted with ethyl acetate and the combined organic phases are dried on magnesium sulphate. The solvents are eliminated in vacuo and the residue is purified by chromatography on silica gel (cyclohexane/ethyl acetate 10:1 to 1:3).

Yield: 127 mg (68% of theory)

Mass spectrum (ESI−): m/z=586 [M−H]−

The following compounds are obtained analogously to Example VI:

(1) tert.butyl [(1-benzylcarbamoyl-1H-indol-4-yl)-(3,5-dichloro-phenylsulphonyl)-amino]-acetate

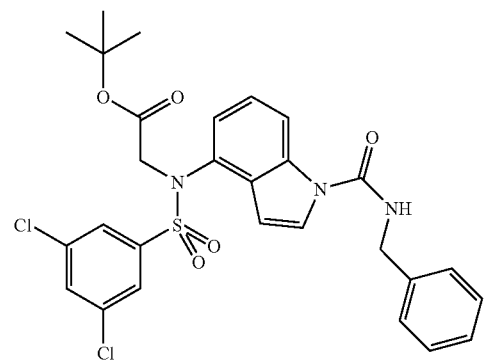

Mass spectrum (ESI−): m/z=586 [M−H]−

(2) tert.butyl [(3,5-dichloro-phenylsulphonyl)-(1-phenylcarbamoyl-1H-indol-5-yl)-amino]-acetate

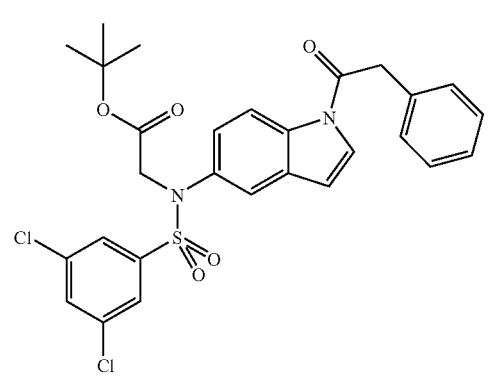

The product is further reacted directly in Example 1 (3).

(3) tert.butyl [(3,5-dichloro-phenylsulphonyl)-(1-phenylacetyl-1H-indol-5-yl)-amino]-acetate Mass spectrum (ESI+): m/z=590 [M+NH4]+

(4) tert.butyl [(3,5-dichloro-phenylsulphonyl)-(1-phenylacetyl-2,3-dihydro-1H-indol-5-yl)-amino]-acetate

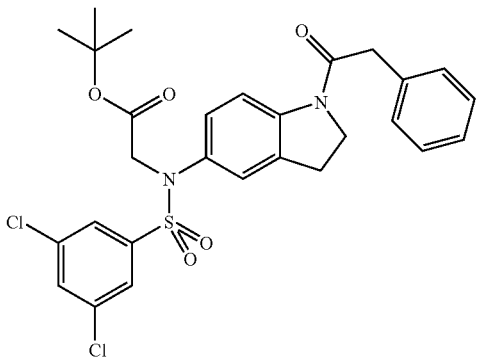

Mass spectrum (ESI⁺): m/z=575 [M+H]⁺

(5) tert.butyl {(3,5-dichloro-phenylsulphonyl)-[1-(phenylethyl)-1H-indol-5-yl]-amino}-acetate

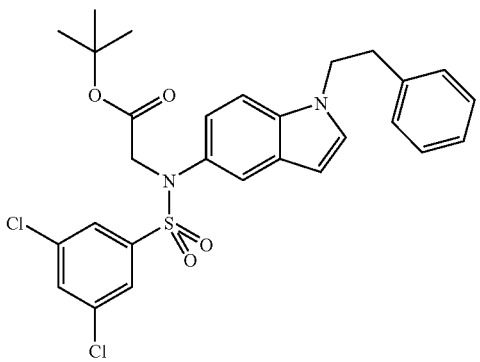

Mass spectrum (ESI⁺): m/z=576 [M+NH₄]⁺

(6) tert.butyl [(3,5-dichloro-phenylsulphonyl)-(1H-indol-5-yl)-amino]-acetate

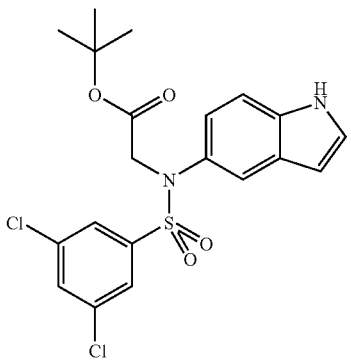

Mass spectrum (ESI⁺): m/z=472 [M+NH₄]⁺

(7) tert.butyl [(3,5-dichloro-phenylsulphonyl)-(2,3-dihydro-1H-indol-5-yl)-amino]-acetate

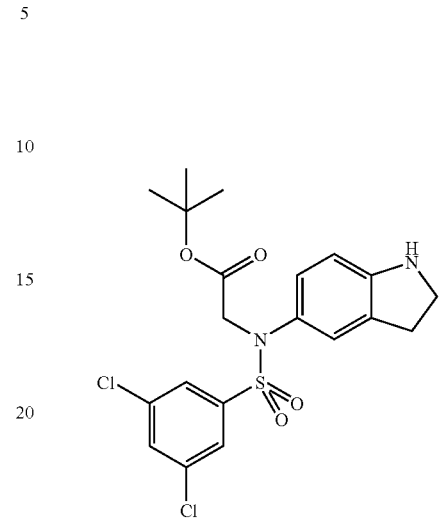

Mass spectrum (ESI⁺): m/z=455 [M−H]⁺

(8) tert.butyl [(3,5-dichloro-phenylsulphonyl)-(1-methylcarbamoyl-2,3-dihydro-1H-indol-5-yl)-amino]-acetate

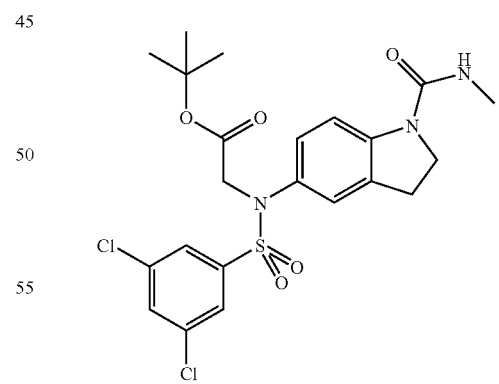

Mass spectrum (ESI⁺): m/z=514 [M+H]⁺

(9) tert.butyl [(3,5-dichloro-phenylsulphonyl)-(1-methylcarbamoyl-2,3-dihydro-1H-indol-4-yl)-amino]-acetate

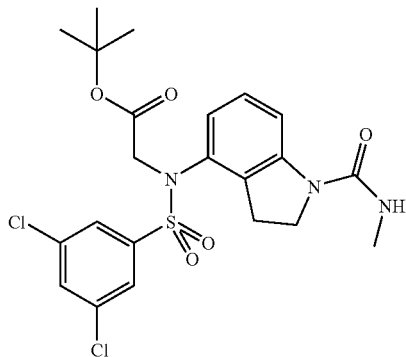

Mass spectrum (ESI⁺): m/z=514 [M+H]⁺

(10) ethyl [(3,5-dichloro-phenylsulphonyl)-(1H-indol-5-yl)-amino]-acetate

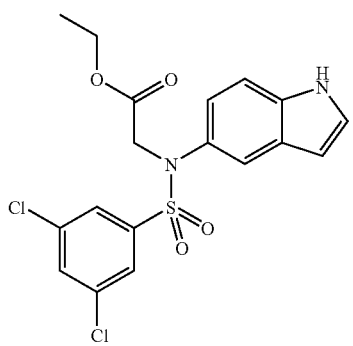

Mass spectrum (ESI⁺): m/z=427 [M+H]⁺

(11) tert.butyl [(3,5-dichloro-phenylsulphonyl)-(1-phenylcarbamoyl-2,3-dihydro-1H-indol-4-yl)-amino]-acetate

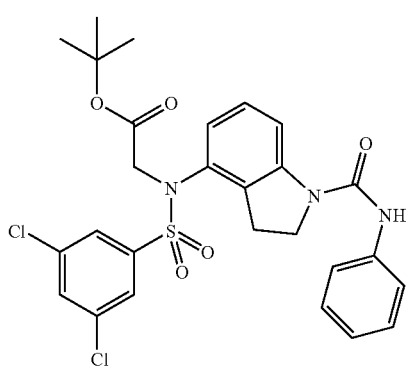

Mass spectrum (ESI⁺): m/z=576 [M+H]⁺

(12) tert.butyl {(3,5-dichloro-phenylsulphonyl)-[1-(pyridin-3-ylcarbamoyl)-2,3-dihydro-1H-indol-4-yl]-amino}-acetate

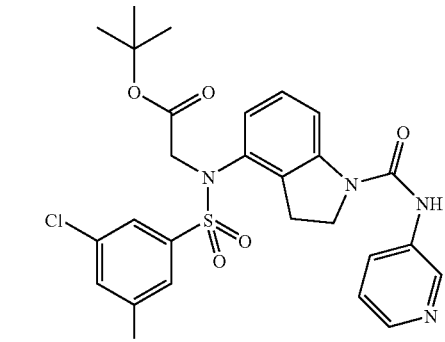

Mass spectrum (ESI⁺): m/z=577 [M+H]⁺

(13) tert.butyl [(3,5-dichloro-phenylsulphonyl)-(1-phenylcarbamoyl-2,3-dihydro-1H-indol-6-yl)-amino]-acetate

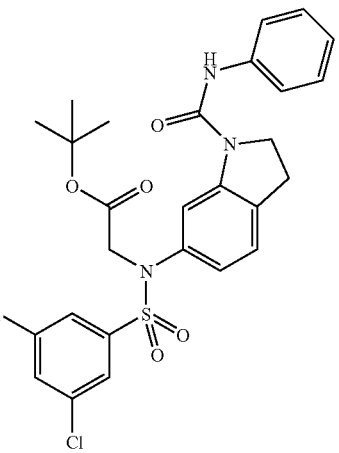

Mass spectrum (ESI⁺): m/z=576 [M+H]⁺

(14) tert-butyl 5-[(3,5-dichloro-phenylsulphonyl)-methoxycarbonylmethyl-amino]-2,3-dihydro-indole-1-carboxylate

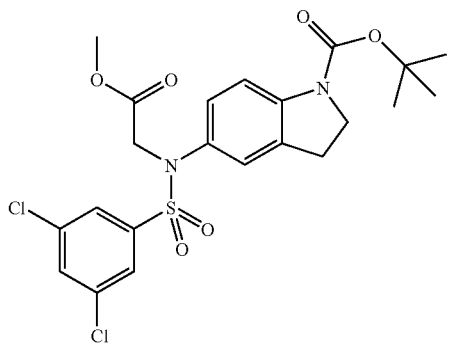

Mass spectrum (ESI⁺): m/z=532 [M+NH$_4$]$^+$

(15) tert.butyl [(3,5-dichloro-phenylsulphonyl)-(2-methyl-benzothiazole-5-yl)-amino]-acetate

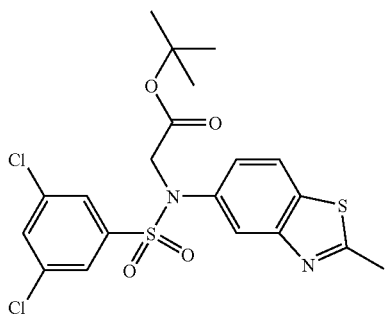

Mass spectrum (ESI⁺): m/z=487 [M+H]$^+$

(16) methyl 5-[tert-butoxycarbonylmethyl-(3,5-dichloro-phenylsulphonyl)-amino]-benzo[b]thiophen-2-carboxylate

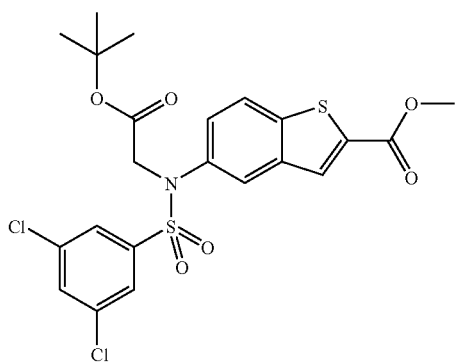

Mass spectrum (ESI⁺): m/z=547 [M+NH$_4$]$^+$

(17) tert.butyl [(3-chloro-5-methoxy-phenylsulphonyl)-(9-ethyl-9H-carbazol-3-yl)-amino]-acetate

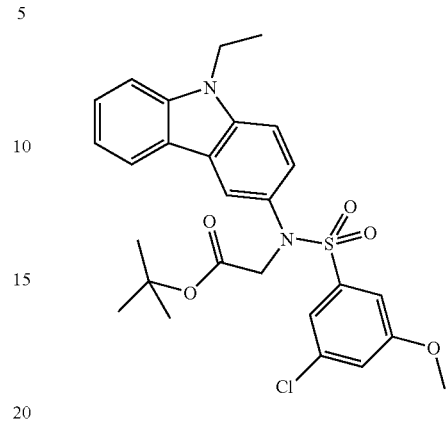

Mass spectrum (ESI⁺): m/z=529 [M+H]$^+$

(18) tert.butyl [(2,6-dichloro-pyridine-4-sulphonyl)-(9-ethyl-9H-carbazol-3-yl)-amino]-acetate

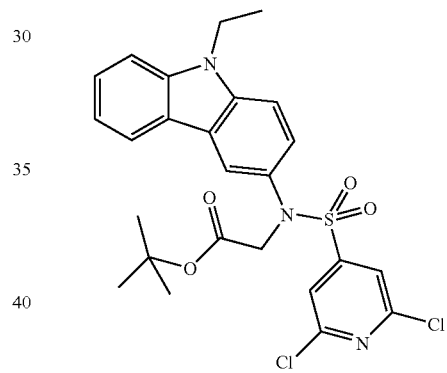

Mass spectrum (ESI⁺): m/z=534 [M+H]$^+$

(19) tert.butyl [(3,5-dichloro-phenylsulphonyl)-(1H-indazol-5-yl)-amino]-acetate

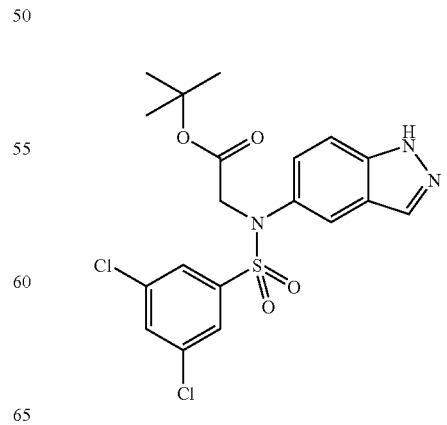

Mass spectrum (ESI⁺): m/z=294 [M+H]$^{30}$

47

R_f value: 0.53 (silica gel: ethyl acetate/petroleum ether 1:1)

(20) tert.butyl {(3,5-dichloro-phenylsulphonyl)-[1-(3,5-dichloro-phenylsulphonyl)-3-methyl-1H-indazol-5-yl]-amino}-acetate

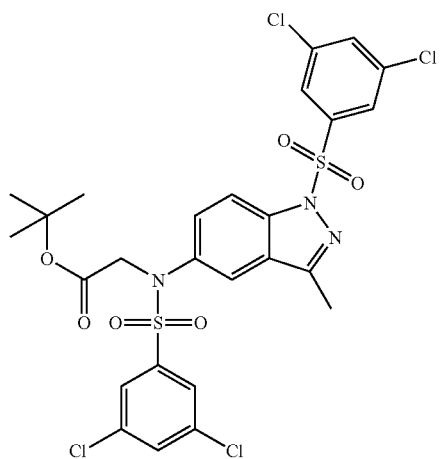

This is isolated as a by-product of the formation of VI (21) from XI (13).
Mass spectrum (ESI+): m/z=678 [M+H]+
R_f value: 0.80 (silica gel: petroleum ether/ethyl acetate 2:1)

(21) tert.butyl [(3,5-dichloro-phenylsulphonyl)-(3-methyl-1H-indazol-5-yl)-amino]-acetate

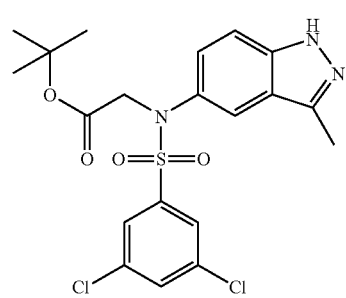

Mass spectrum (ESI+): m/z=470 [M+H]+

48

R_f value: 0.32 (silica gel: petroleum ether/ethyl acetate 2:1)

(22) tert-butyl [(3-chloro-5-trifluoromethylsulphonyloxy-phenylsulphonyl)-(9-ethyl-9H-carbazol-3-yl)-amino]-acetate

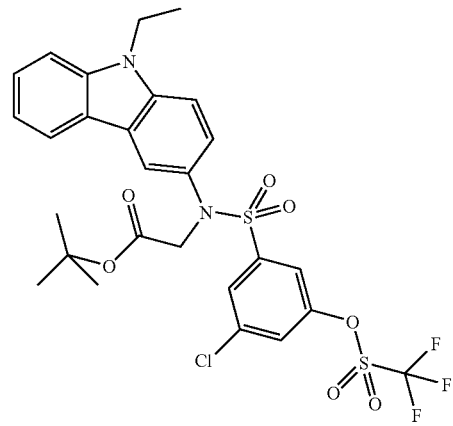

Mass spectrum (ESI+): m/z=664 [M+NH_4]+

(23) tert-butyl 3-(tert-butoxycarbonyl-methyl-aminocarbonyl)-6-[tert-butoxycarbonylmethyl-(3,5-dichloro-phenylsulphonyl)-amino]-indole-1-carboxylate

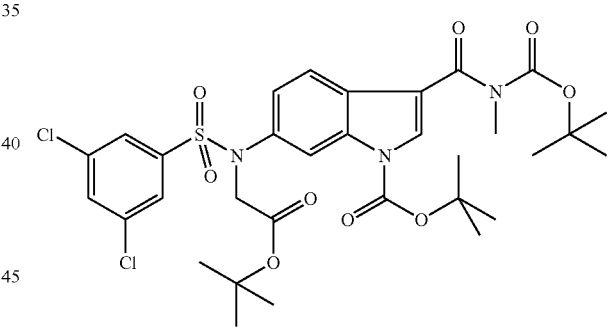

Mass spectrum (ESI+): m/z=712 [M+H]+

(24) methyl [(3,5-dichloro-phenylsulphonyl)-(9-ethyl-9H-carbazol-3-yl)-amino]-acetate

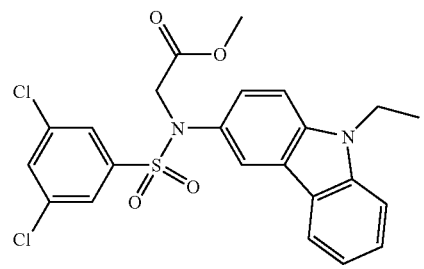

The product is further reacted directly in Example 6.

(25) tert.butyl [[9-(2-phenylsulphonyl-ethyl)-9H-carbazol-3-yl]-(3,5-dichloro-phenylsulphonyl)-amino]-acetate

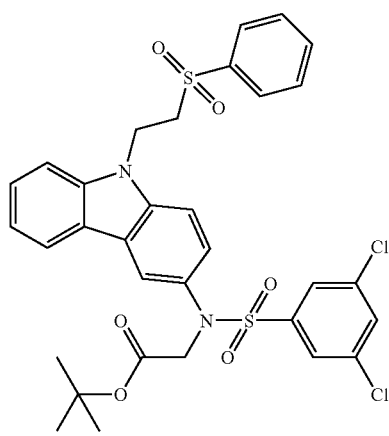

Mass spectrum (ESI⁺): m/z=690 [M+NH₄]⁺

(26) methyl 5-[tert-butoxycarbonylmethyl-(3,5-dichloro-phenylsulphonyl)-amino]-benzo[b]thiophen-2-carboxylate

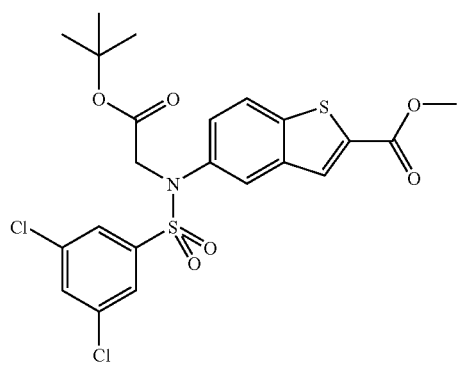

Mass spectrum (ESI⁺): m/z=547 [M+NH₄]⁺

(27) tert.butyl [(9H-carbazol-3-yl)-(3,5-dichloro-phenylsulphonyl)-amino]-acetate

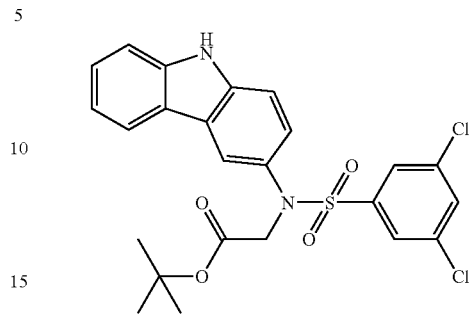

Mass spectrum (ESI⁻): m/z=503 [M−H]⁻

(28) tert.butyl {6-[tert-butoxycarbonylmethyl-(3,5-dichloro-phenylsulphonyl)-amino]-3-phenylcarbamoyl-indol-1-yl}-acetate

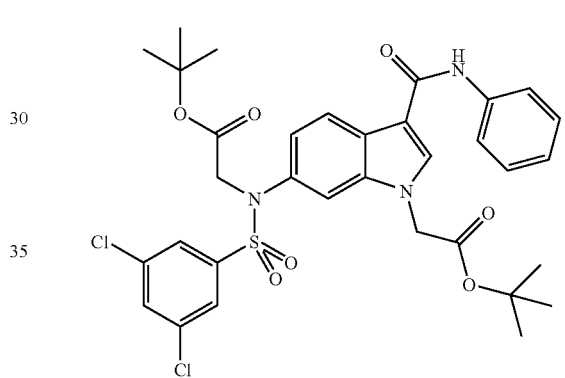

Obtained from the reaction of 6-(3,5-dichloro-phenylsulphonylamino)-1H-indole-3-carboxylic acid-phenylamide.

The product is further reacted directly in 1 (38).

(29) tert.butyl {(3,5-dichloro-phenylsulphonyl)-[1-(phenylethyl)-1H-benzoimidazol-5-yl]-amino}-acetate

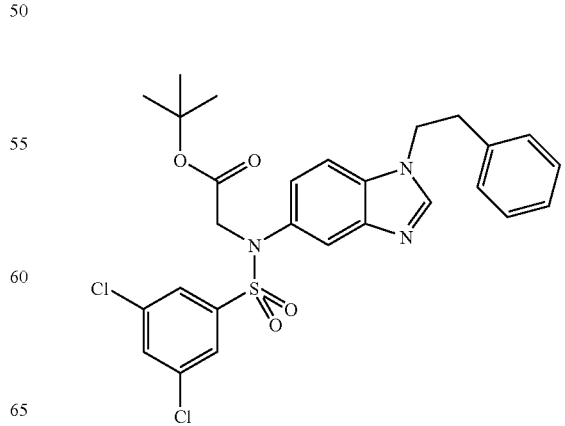

and tert.butyl {(3,5-dichloro-phenylsulphonyl)-[3-(phenylethyl)-3H-benzoimidazol-5-yl]-amino}-acetate

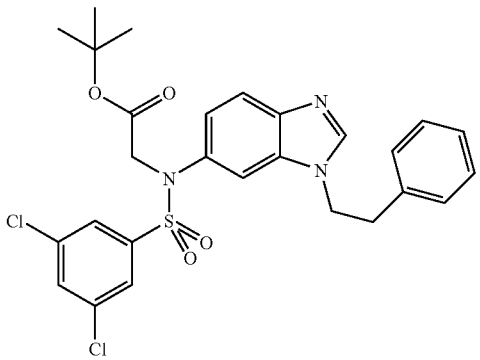

Obtained from the reaction of a mixture of 3,5-dichloro-N-(1-phenylethyl-1H-benzoimidazol-5-yl)-phenylsulphonamide and 3,5-dichloro-N-[3-(phenylethyl)-3H-benzoimidazol-5-yl]-phenylsulphonamide. The products may be separated by chromatography on silica gel.

Mass spectrum (ESI$^+$): m/z=560 [M+H]$^+$ tert.butyl {(3,5-dichloro-phenylsulphonyl)-[1-(phenylethyl)-1H-benzoimidazol-5-yl]-amino}-acetate and Mass spectrum (ESI$^+$): m/z=560 [M+H]$^+$ tert.butyl {(3,5-dichloro-phenylsulphonyl)-[3-(phenylethyl)-3H-benzoimidazol-5-yl]-amino}-acetate

(30) tert.butyl [(3,5-dichloro-phenylsulphonyl)-(2-dimethylcarbamoyl-1H-indol-5-yl)-amino]-acetate

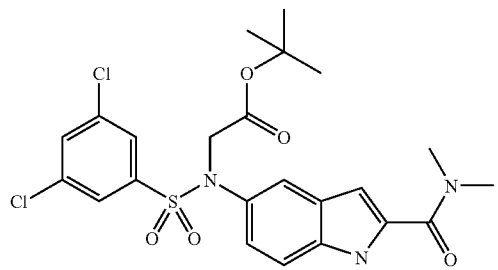

Mass spectrum (ESI$^+$): m/z=526 [M+H]$^+$

(31) tert-butyl 6-[tert-butoxycarbonylmethyl-(3,5-dichloro-phenylsulphonyl)-amino]-3-(morpholine-4-carbonyl)-indole-1-carboxylate

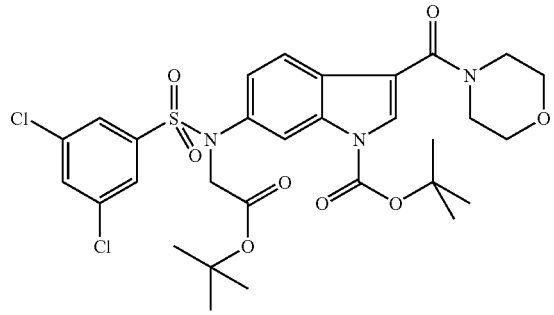

Mass spectrum (ESI$^+$): m/z=668 [M+H]$^+$

(32) tert-butyl 6-[tert-butoxycarbonylmethyl-(3,5-dichloro-phenylsulphonyl)-amino]-3-(4-tert-butoxycarbonyl-piperazin-1-carbonyl)-indole-1-carboxylate

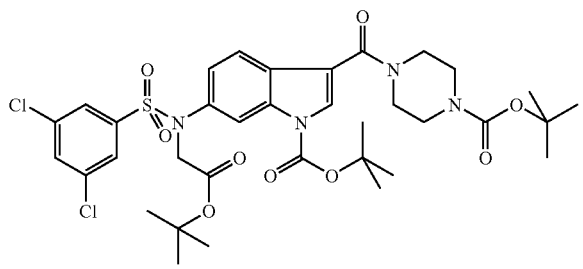

Mass spectrum (ESI$^+$): m/z=767 [M+H]$^+$

(33) tert-butyl 3-(benzyl-tert-butoxycarbonyl-aminocarbonyl)-6-[tert-butoxycarbonylmethyl-(3,5-dichloro-phenylsulphonyl)-amino]-indole-1-carboxylate

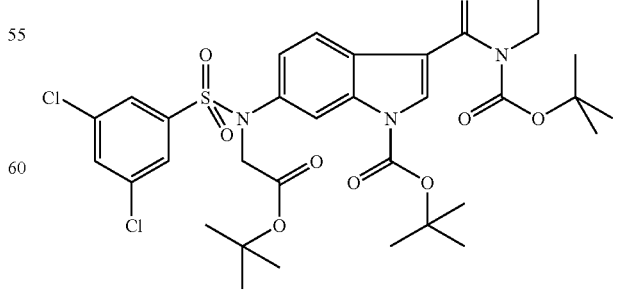

Mass spectrum (ESI$^+$): m/z=788 [M+H]$^+$

53

(34) tert-butyl 3-(bis-tert-butoxycarbonyl)-aminocarbonyl-6-[tert-butoxycarbonylmethyl-(3,5-dichloro-phenylsulphonyl)-amino]-indole-1-carboxylate

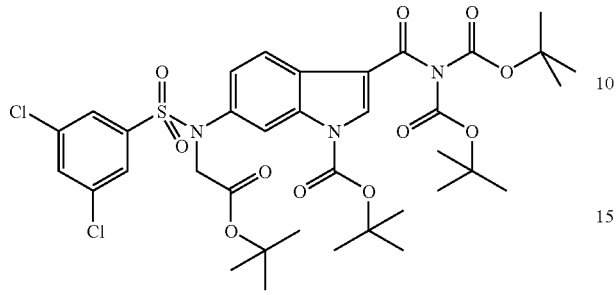

Mass spectrum (ESI⁺): m/z=798 [M+H]⁺

(35) tert-butyl 6-[tert-butoxycarbonylmethyl-(3,5-dichloro-phenylsulphonyl)-amino]-3-(tert-butoxycarbonyl-phenyl-aminocarbonyl)-indole-1-carboxylate

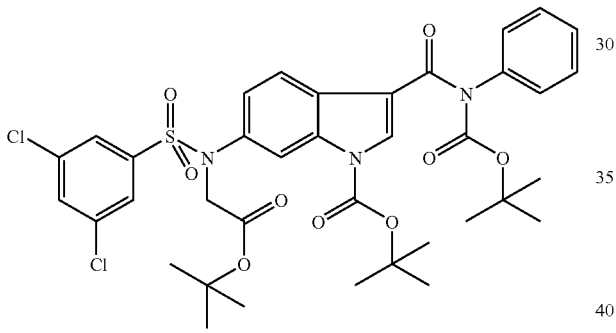

Mass spectrum (ESI⁺): m/z=774 [M+H]⁺

(36) tert.butyl [(3-cyano-1-methyl-1H-indol-6-yl)-(3,5-dichloro-phenylsulphonyl)-amino]-acetate

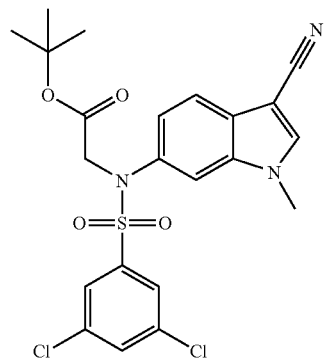

Mass spectrum (ESI⁺): m/z=511 [M+NH₄]⁺

54

(37) tert.butyl [(3,5-dichloro-phenylsulphonyl)-(3-dimethylcarbamoyl-1-methyl-1H-indol-6-yl)-amino]-acetate

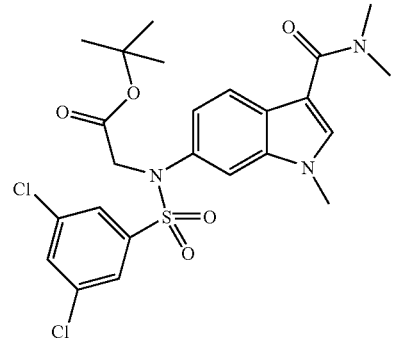

Mass spectrum (ESI⁺): m/z=540 [M+H]⁺

(38) tert.butyl [(3-carbamoyl-1-methyl-1H-indol-6-yl)-(3,5-dichloro-phenylsulphonyl)-amino]-acetate

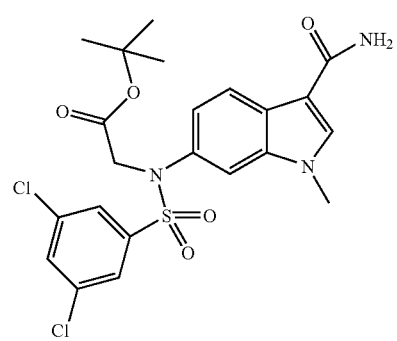

Mass spectrum (ESI⁺): m/z=512 [M+H]⁺

(39) tert.butyl [(3,5-dichloro-phenylsulphonyl)-(3-methylcarbamoyl-benzo[b]thiophen-5-yl)-amino]-acetate

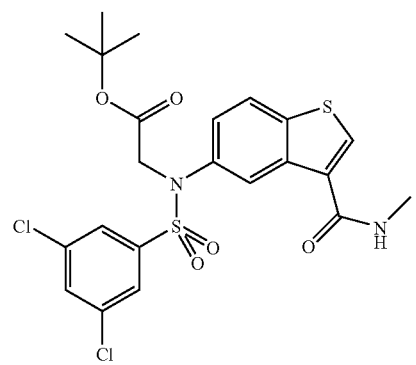

Mass spectrum (ESI⁺): m/z=546 [M+NH₄]⁺

(40) tert.butyl [(3,5-dichloro-phenylsulphonyl)-(3-methylcarbamoyl-benzo[b]thiophen-6-yl)-amino]-acetate

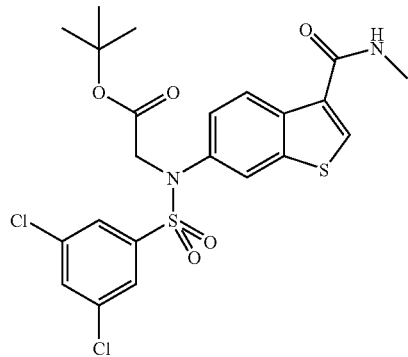

Mass spectrum (ESI⁺): m/z=529 [M+H]⁺

(41) tert-butyl 6-[tert-butoxycarbonylmethyl-(3,5-dichloro-phenylsulphonyl)-amino]-3-(4-tert-butoxy-carbonyl-3-oxo-piperazin-1-carbonyl)-indole-1-carboxylate

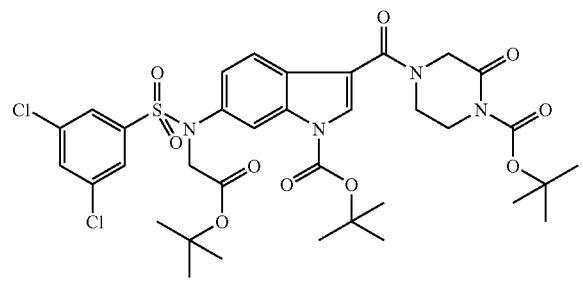

Mass spectrum (ESI⁺): m/z=798 [M+NH₄]⁺

(42) tert.butyl {(3,5-dichloro-phenylsulphonyl)-[3-(1-methylcarbamoyl-ethylcarbamoyl)-1H-indol-6-yl]-amino}-acetate

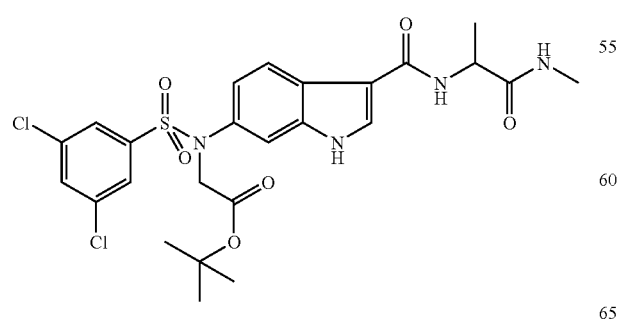

Mass spectrum (ESI⁻): m/z=581 [M–H]⁻

(43) tert.butyl {(3,5-dichloro-phenylsulphonyl)-[1-methyl-3-(morpholine-4-carbonyl)-1H-indol-6-yl]-amino}-acetate

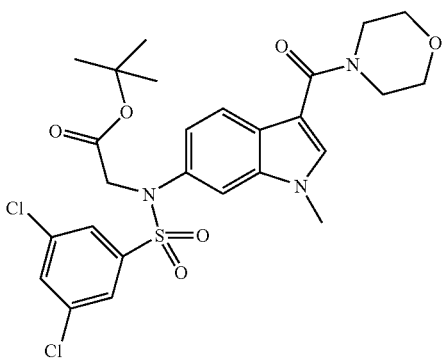

Mass spectrum (ESI⁻): m/z=582 [M–H]⁻

(44) tert.butyl {(3,5-dichloro-phenylsulphonyl)-(1-methyl-3-methylcarbamoyl-1H-indol-6-yl)-amino}-acetate

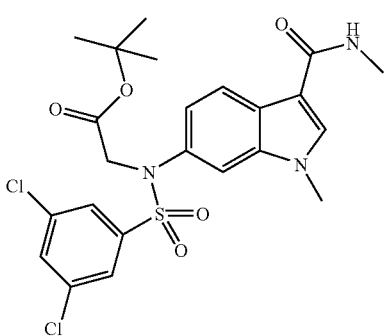

Mass spectrum (ESI⁺): m/z=526 [M+H]⁺

(45) tert.butyl {(3,5-dichloro-phenylsulphonyl)-[1-methyl-3-(pyrrolidine-1-carbonyl)-1H-indol-6-yl]-amino}-acetate

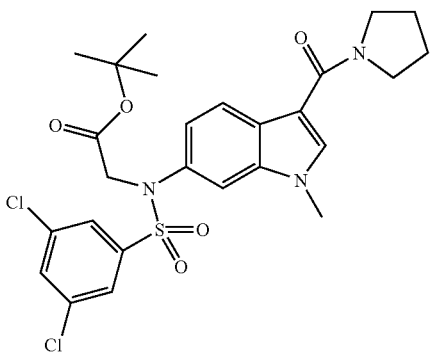

Mass spectrum (ESI⁺): m/z=566 [M+H]⁺

(46) tert.butyl {(3,5-dichloro-phenylsulphonyl)-[1-methyl-3-(piperidine-1-carbonyl)-1H-indol-6-yl]-amino}acetate

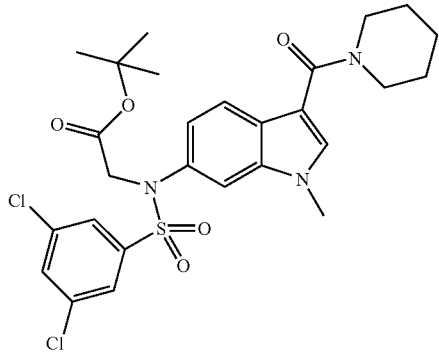

Mass spectrum (ESI⁺): m/z=580 [M+H]⁺

(47) tert.butyl (3,5-dichloro-phenylsulphonyl)-(1-methyl-3-phenylcarbamoyl-1H-indol-6-yl)-amino]-acetate

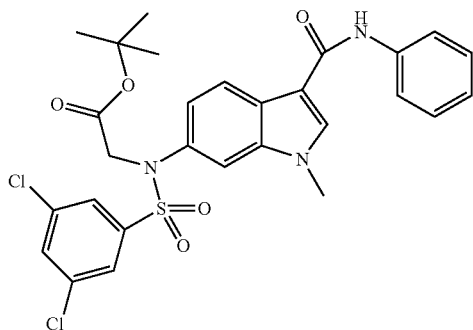

Mass spectrum (ESI⁺): m/z=588 [M+H]⁺

(48) tert.butyl [(3-benzylcarbamoyl-1-methyl-1H-indol-6-yl)-(3,5-dichloro-phenylsulphonyl)-amino]-acetate

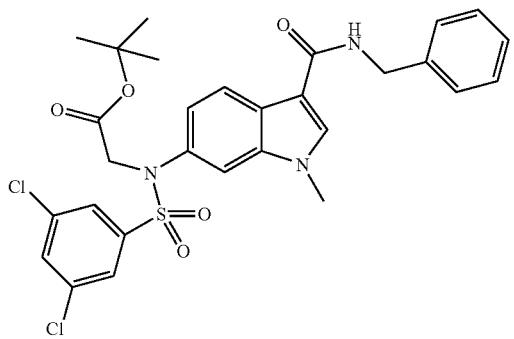

Mass spectrum (ESI⁺): m/z=602 [M+H]⁺

(49) tert.butyl [(3,5-dimethyl-phenylsulphonyl)-(1-methylcarbamoyl-2,3-dihydro-1H-indol-5-yl)-amino]-acetate

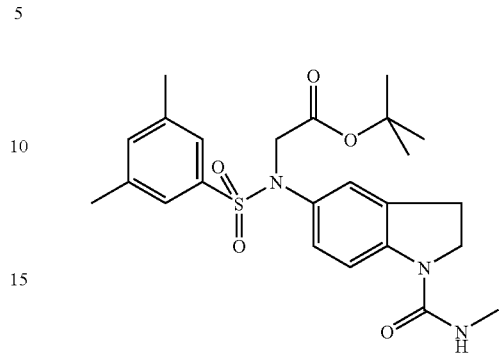

Mass spectrum (ESI⁺): m/z=474 [M+H]⁺

(50) tert-butyl 6-[tert-butoxycarbonylmethyl-(3,5-dichloro-phenylsulphonyl)-amino]-3-dimethylcarbamoyl-indole-1-carboxylate

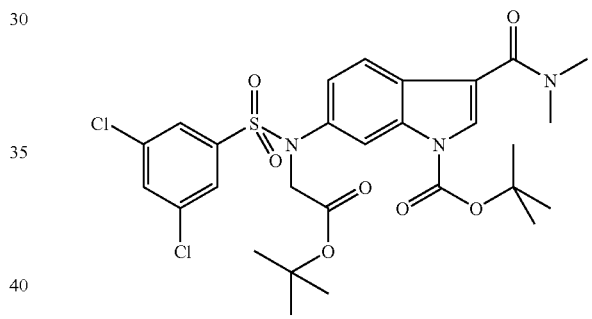

Mass spectrum (ESI⁺): m/z=626 [M+H]⁺

(51) tert.butyl [(3-aminooxalyl-1-methyl-1H-indol-6-yl)-(3,5-dichloro-phenylsulphonyl)-amino]-acetate

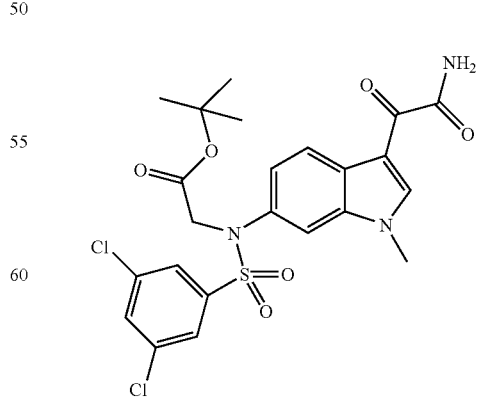

Mass spectrum (ESI⁺): m/z=540 [M+H]⁺

(52) tert.butyl [(3,5-dichloro-phenylsulphonyl)-(1-methyl-3-methylaminooxalyl-1H-indol-6-yl)-amino]-acetate

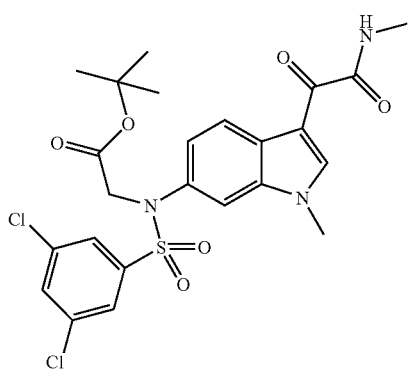

Mass spectrum (ESI+): m/z=554 [M+H]+

(53) tert.butyl [(3,5-dichloro-phenylsulphonyl)-(3-dimethylamidooxalyl-1-methyl-1H-indol-6-yl)-amino]-acetate

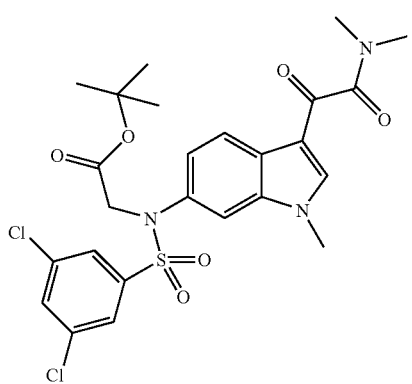

Mass spectrum (ESI+): m/z=568 [M+H]+

(54) tert.butyl {(3,5-dichloro-phenylsulphonyl)-[1-methyl-3-(2-oxo-2-pyrrolidin-1-yl-acetyl)-1H-indol-6-yl]-amino}-acetate

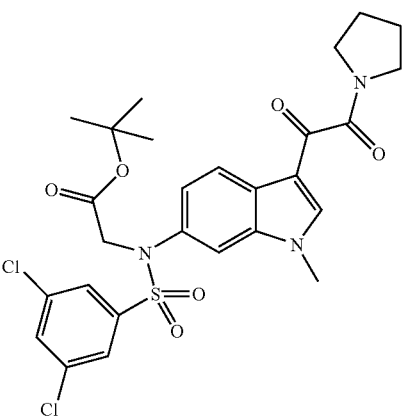

Mass spectrum (ESI+): m/z=594 [M+H]+

(55) tert.butyl [[3-(azetidine-1-carbonyl)-1-methyl-1H-indol-6-yl]-(3,5-dichloro-phenylsulphonyl)-amino]-acetate

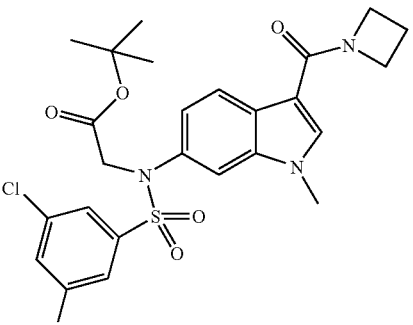

Mass spectrum (ESI+): m/z=552 [M+H]+

(56) tert.butyl [(3,5-dichloro-phenylsulphonyl)-(1,3-dimethyl-2-oxo-2,3-dihydro-1H-benzoimidazol-5-yl)-amino]-acetate

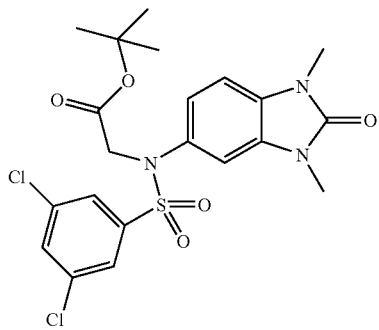

Mass spectrum (ESI⁺): m/z=500 [M+H]⁺

(57) methyl 5-[tert-butoxycarbonylmethyl-(3,5-dichloro-phenylsulphonyl)-amino]-1-methylcarbamoyl-2,3-dihydro-1H-indole-3-carboxylate

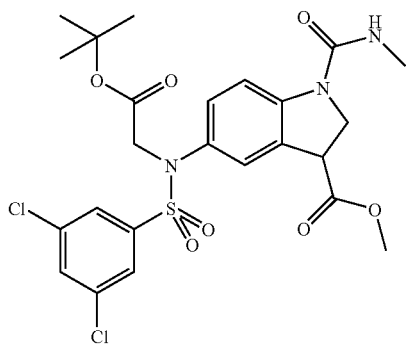

Mass spectrum (ESI⁺): m/z=572 [M+H]⁺

(58) tert.butyl {(3,5-dichloro-phenylsulphonyl)-[3-(3-hydroxy-pyrrolidine-1-carbonyl)-1-methyl-1H-indol-6-yl]-amino}-acetate

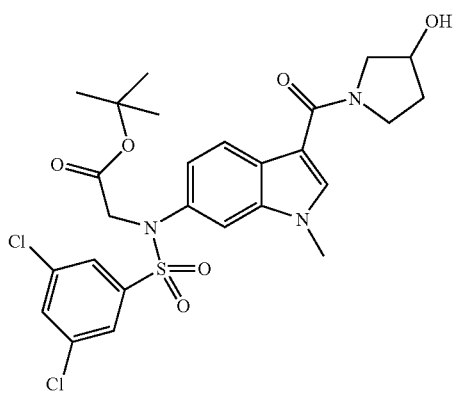

$R_f$ value: 0.27 (silica gel: dichloromethane/methanol 9:1)

(59) tert.butyl [(3-cyclopropylcarbamoyl-1-methyl-1H-indol-6-yl)-(3,5-dichloro-phenylsulphonyl)-amino]-acetate

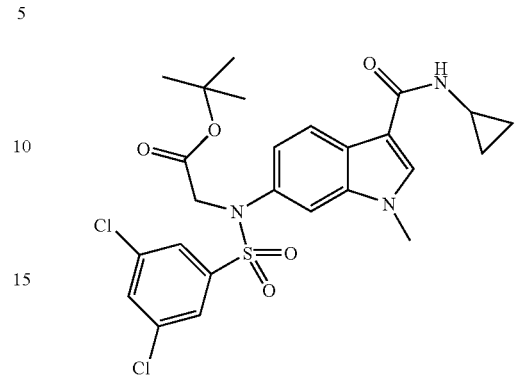

$R_f$ value: 0.39 (silica gel: petroleum ether/ethyl acetate 1:2)

(60) tert.butyl [[3-(cyclopropyl-methyl-carbamoyl)-1-methyl-1H-indol-6-yl]-(3,5-dichloro-phenylsulphonyl)-amino]-acetate

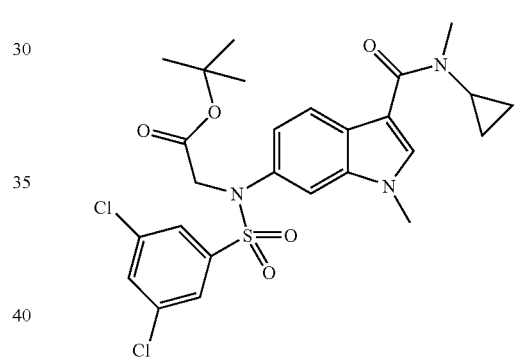

$R_f$ value: 0.34 (silica gel: petroleum ether/ethyl acetate 1:2)

(61) tert.butyl {(3,5-dichloro-phenylsulphonyl)-[1-methyl-3-(2-methylcarbamoyl-pyrrolidine-1-carbonyl)-1H-indol-6-yl]-amino}-acetate

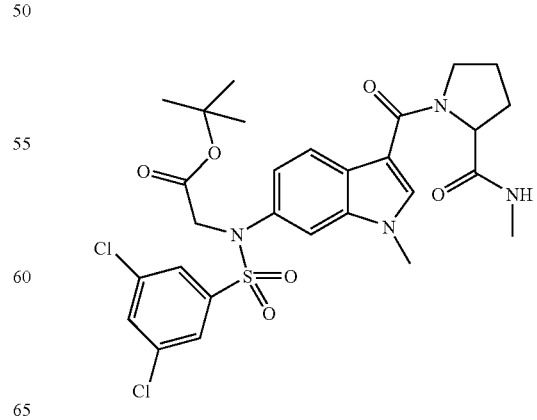

$R_f$ value: 0.44 (silica gel: dichloromethane/methanol 9:1)

(62) tert.butyl {(3-chloro-5-methyl-phenylsulphonyl)-[1-methyl-3-(pyrrolidine-1-carbonyl)-1H-indol-6-yl]-amino}-acetate

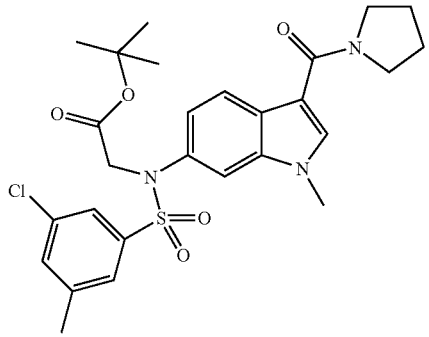

Mass spectrum (ESI⁺): m/z=546 [M+H]⁺

(63) tert.butyl {(3,5-dimethyl-phenylsulphonyl)-[1-methyl-3-(pyrrolidine-1-carbonyl)-1H-indol-6-yl]-amino}-acetate

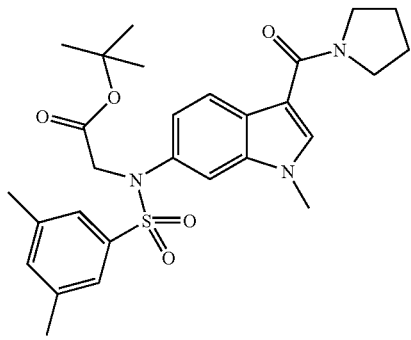

Mass spectrum (ESI⁺): m/z=526 [M+H]⁺

(64) tert.butyl {(3,5-dichloro-phenylsulphonyl)-[1-methyl-3-(pyrrolidine-1-carbonyl)-1H-indazol-6-yl]-amino}-acetate

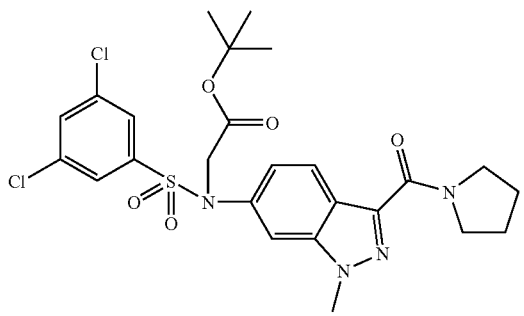

Mass spectrum (ESI⁺): m/z=567 [M+H]⁺

(65) tert.butyl [(3,5-dichloro-phenylsulphonyl)-(1-methyl-3-methylcarbamoyl-1H-indazol-6-yl)-amino]-acetate

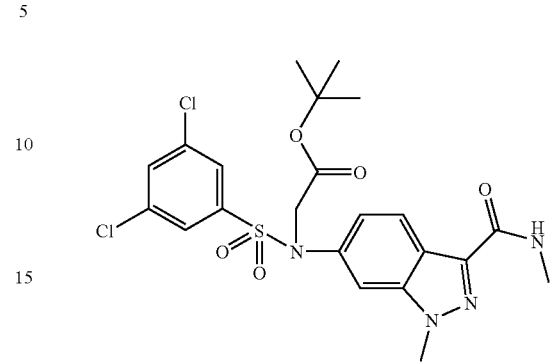

Mass spectrum (ESI⁺): m/z=527 [M+H]⁺

(66) tert.butyl [(3-carbamoyl-benzo[b]thiophen-6-yl)-(3,5-dichloro-phenylsulphonyl)-amino]-acetate

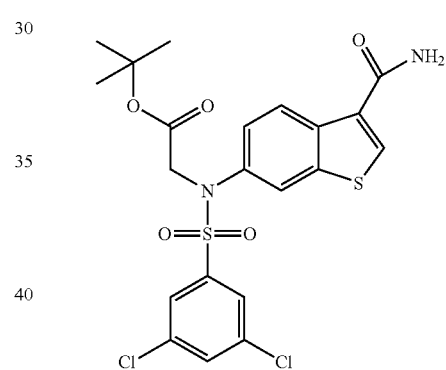

Mass spectrum (ESI⁺): m/z=532 [M+NH₄]⁺

(67) tert.butyl [(3-carbamoyl-benzo[b]thiophen-5-yl)-(3,5-dichloro-phenylsulphonyl)-amino]-acetate

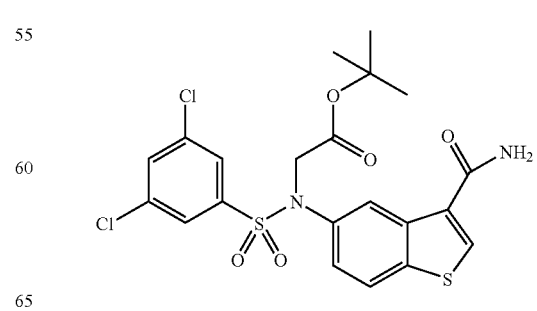

Mass spectrum (ESI⁺): m/z=532 [M+NH₄]⁺

EXAMPLE VII

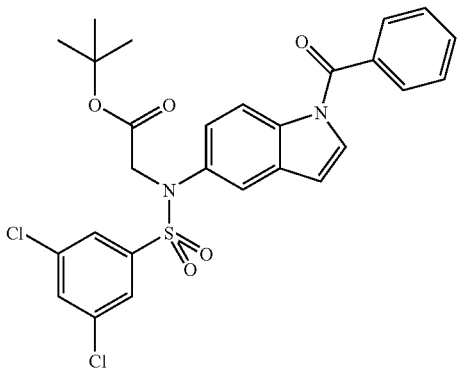

tert.butyl [(1-benzoyl-1H-indol-5-yl)-(3,5-dichloro-phenylsulphonyl)-amino]-acetate 50 mg tert.butyl [(3,5-dichloro-phenylsulphonyl)-(1H-indol-5-yl)-amino]-acetate are dissolved in 2 ml dichloromethane. 5 mg powdered sodium hydroxide and 19 µl benzoyl chloride are added. Then the mixture is stirred for 4 hours at ambient temperature, divided between 1 N sodium hydroxide solution and ethyl acetate, the aqueous phase is extracted with ethyl acetate and the combined organic phases are dried with magnesium sulphate. The solvents are eliminated in vacuo and the residue is chromatographed on silica gel (cyclohexane/ethyl acetate 10:1 to 1:2).

Yield: 15 mg (24% of theory)

Mass spectrum (ESI$^+$): m/z=576 [M+NH$_4$]$^{30}$

EXAMPLE VIII

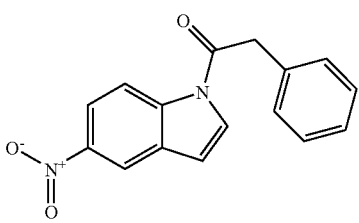

1-(5-nitro-indol-1-yl)-2-phenyl-ethanone 300 mg 5-nitroindole are dissolved in 10 ml of tetrahydrofuran. 81 mg sodium hydride (60% in mineral oil) are added and the mixture is stirred for 1 hour at ambient temperature. Then 294 µl phenylacetic acid chloride are added dropwise and the mixture is stirred for another 3 hours. It is divided between saturated ammonium chloride solution and ethyl acetate. The aqueous phase is extracted with ethyl acetate and the combined organic phases are dried on magnesium sulphate. The solvents are eliminated in vacuo and the residue is chromatographed on silica gel (cyclohexane/ethyl acetate 10:1 to 1:3).

Yield: 250 mg (48% of theory)

Mass spectrum (ESI$^+$): m/z=281 [M+H]$^+$

The following compounds are obtained analogously to Example VIII:

(1) 5-nitro-1-(phenylethyl)-1H-indole

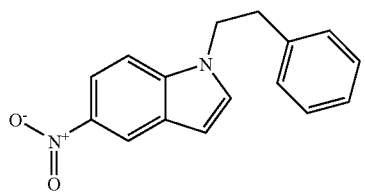

Dimethylformamide is used instead of tetrahydrofuran.

Mass spectrum (ESI$^+$): m/z=267 [M+H]$^+$ (2) 5-nitro-1-(phenylethyl)-1H-benzimidazole

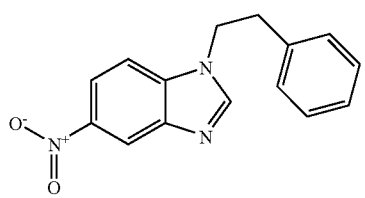

and 6-nitro-1-(phenylethyl)-1H-benzimidazole

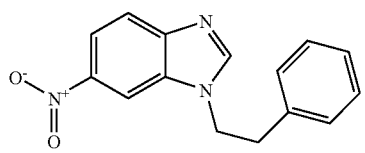

Dimethylformamide is used instead of tetrahydrofuran.

The compounds are obtained as a mixture of regioisomers.

Mass spectrum (ESI$^+$): m/z=268 [M+H]$^+$

EXAMPLE IX

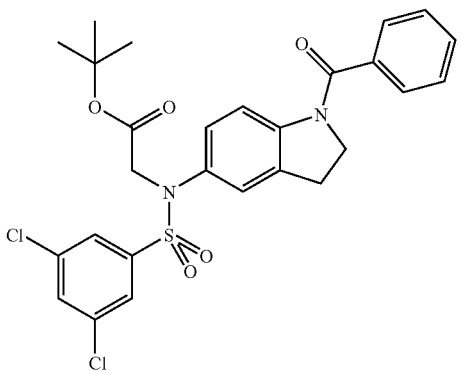

tert.butyl [(1-benzoyl-2,3-dihydro-1H-indol-5-yl)-(3,5-dichloro-phenylsulphonyl)-amino]-acetate 150 mg tert.butyl [(3,5-dichloro-phenylsulphonyl)-(2,3-dihydro-1H-indol-5-yl)-amino]-acetate are dissolved in 5 ml dichloromethane. 110 mg potassium carbonate and 45 µl benzoyl chloride are added, the mixture is stirred for 3 hours at ambient temperature and then divided between dichloromethane and water. The organic phase is washed with water and then dried on magnesium sulphate. The solvents are eliminated in vacuo.

Yield: 170 mg (92% of theory)

Mass spectrum (ESI$^+$): m/z=561 [M+H]$^+$

The following compounds are obtained analogously to Example IX:

(1) tert.butyl [(1-phenylsulphonyl-2,3-dihydro-1H-indol-5-yl)-(3,5-dichloro-phenylsulphonyl)-amino]-acetate

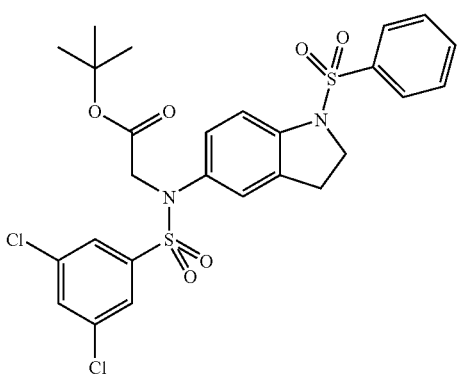

Phenylsulphonyl chloride is used instead of benzoyl chloride.

Mass spectrum (ESI$^+$): m/z=614 [M+NH$_4$]$^+$ (2) tert.butyl [(3,5-dichloro-phenylsulphonyl)-(1-phenylmethanesulphonyl-2,3-dihydro-1H-indol-5-yl)-amino]-acetate

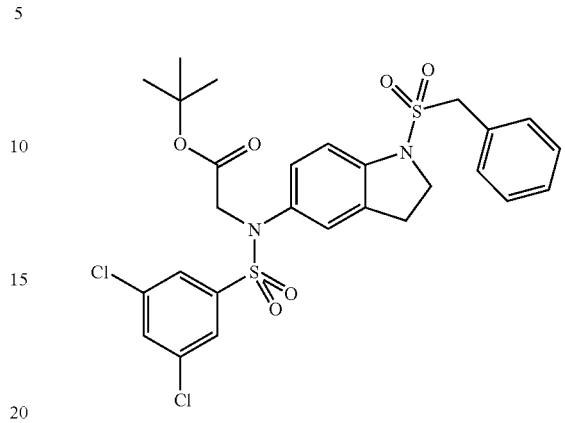

Phenylmethanesulphonyl chloride is used instead of benzoyl chloride.

Mass spectrum (ESI$^+$): m/z=628 [M+NH$_4$]$^+$

EXAMPLE X

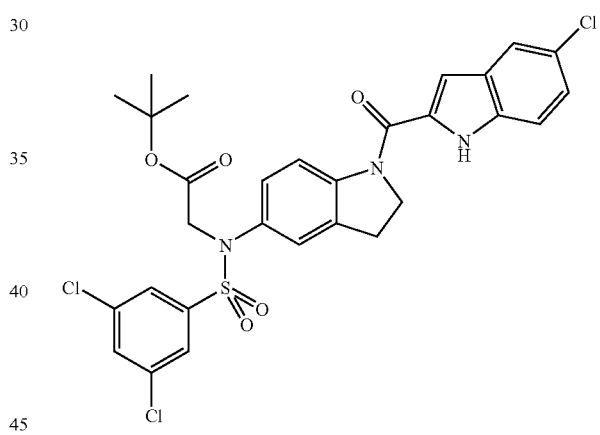

tert.butyl [[1-(5-chloro-1H-indol-2-carbonyl)-2,3-dihydro-1H-indol-5-yl]-(3,5-dichloro-phenylsulphonyl)-amino]-acetate 55 mg 5-chloro-1H-indol-2-carboxylic acid are dissolved in 2 ml of thionyl chloride and heated to 80° C. for 1 hour. The solvent is eliminated in vacuo and the residue is twice combined with dichloromethane and the latter is eliminated again in vacuo. The residue is taken up in 5 ml dichloromethane and the solution is added dropwise to a mixture of 100 mg tert-.butyl [(3,5-dichloro-phenylsulphonyl)-(2,3-dihydro-1H-indol-5-yl)-amino]-acetate and 60 mg potassium carbonate in 2 ml dimethylformamide. The mixture is stirred for 2 hours at ambient temperature, diluted with ethyl acetate and washed with 1 N HCl and saturated sodium chloride solution. After drying with magnesium sulphate the solvents are eliminated in vacuo and the residue is chromatographed on silica gel (cyclohexane/ethyl acetate 10:1 to 1:2)

Yield: 60 mg (43% of theory)

Mass spectrum (ESI$^+$): m/z=634 [M+H]$^+$.

EXAMPLE XI

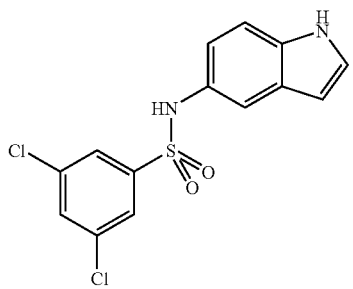

3,5-dichloro-N-(1H-indol-5-yl)-phenylsulphonamide 100 mg 5-aminoindole are dissolved in 10 ml of pyridine. 186 mg 3,5-dichlorophenylsulphonyl chloride are added thereto and the mixture is stirred for 4 hours at ambient temperature. The solvent is eliminated in vacuo and the residue is divided between water and ethyl acetate. The aqueous phase is extracted with ethyl acetate and the combined organic phases are washed with saturated sodium chloride solution. After drying with magnesium sulphate the solvents are eliminated in vacuo and the residue is chromatographed on silica gel (cyclohexane/ethyl acetate 10:1 to 1:5).

Yield: 240 mg (93% of theory)

Mass spectrum (ESI$^+$): m/z=341 [M+H]$^+$

The following compounds are obtained analogously to Example XI:

(1) 3,5-dichloro-N-(1H-indol-4-yl)-phenylsulphonamide

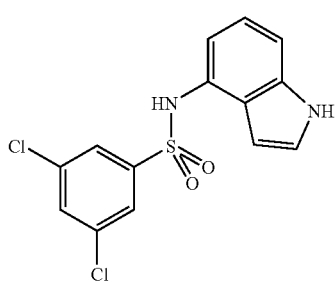

Mass spectrum (ESI$^+$): m/z=341 [M+H]$^+$ (2) tert-butyl 5-(3,5-dichloro-phenylsulphonylamino)-2,3-dihydro-indole-1-carboxylate

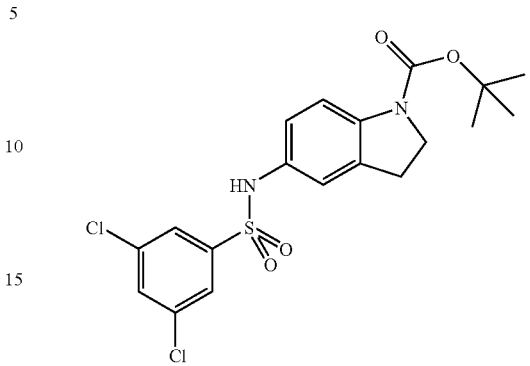

Mass spectrum (ESI$^+$): m/z=460 [M+NH$_4$]$^+$ (3) 5-(3,5-dichloro-phenylsulphonylamino)-2,3-dihydro-indole-1-carboxylic acid-methylamide

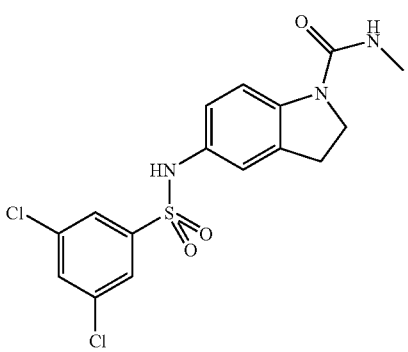

The crude product is extracted from diisopropylether.

Mass spectrum (ESI$^+$): m/z=400 [M+H]$^+$ (4) 4-(3,5-dichloro-phenylsulphonylamino)-2,3-dihydro-indole-1-carboxylic acid-methylamide

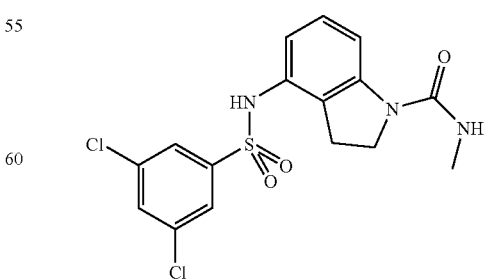

Mass spectrum (ESI$^+$): m/z=400 [M+H]$^+$ (5) 4-(3,5-dichloro-phenylsulphonylamino)-2,3-dihydro-indole-1-carboxylic acid-phenylamide

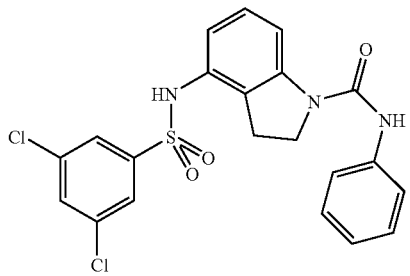

Mass spectrum (ESI$^+$): m/z=462 [M+H]$^+$ (6) 4-(3,5-dichloro-phenylsulphonylamino)-2,3-dihydro-indole-1-carboxylic acid-pyridin-3-ylamide

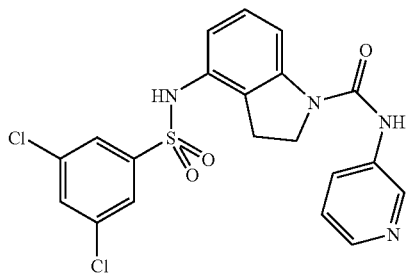

Mass spectrum (ESI$^+$): m/z=463 [M+H]$^+$ (7) 3,5-dichloro-N-[4-ethyl-3-(1-methyl-3-phenyl-ureido)-phenyl]-phenylsulphonamide

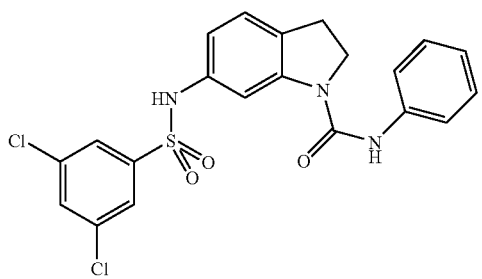

The reaction is carried out in dichloromethane/pyridine 2:1. The crude product is extracted from diisopropylether.
Mass spectrum (ESI$^+$): m/z=462 [M+H]$^+$ (8) 3,5-dichloro-N-(2-methyl-benzothiazole-5-yl)-phenylsulphonamide

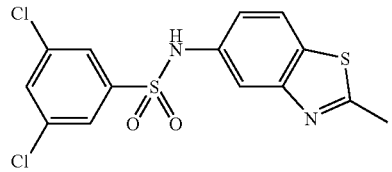

The reaction is carried out in dichloromethane with 2 equivalents of triethylamine.
Mass spectrum (ESI$^+$): m/z=373 [M+H]$^+$ (9) methyl 5-(3,5-dichloro-phenylsulphonylamino)-benzo[b]thiophen-2-carboxylate

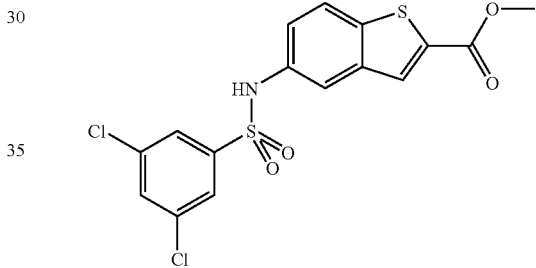

Mass spectrum (ESI$^-$): m/z=414 [M−H]$^-$

(10) 3,5-dichloro-N-(9-ethyl-9H-carbazol-3-yl)-phenylsulphonamide

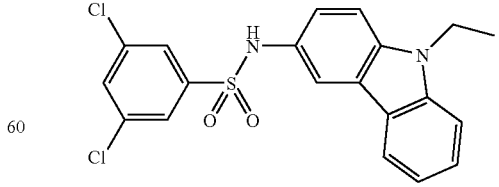

The reaction is carried out in dichloromethane/pyridine 5:1.
The product is further reacted directly in Example VI (24).

(11) N-(9H-carbazol-3-yl)-3,5-dichloro-phenylsulphonamide

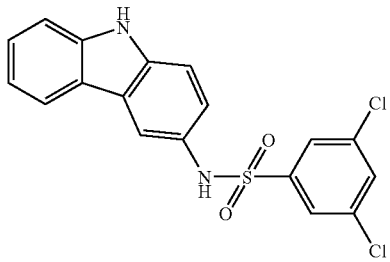

The reaction is carried out in dichloromethane/pyridine 5:1.

Mass spectrum (ESI⁺): m/z=389 [M+H]⁺

(12) 3-chloro-N-(9-ethyl-9H-carbazol-3-yl)-5-methoxy-phenylsulphonamide

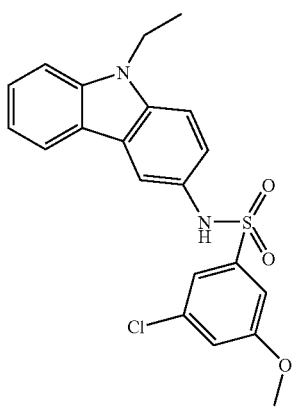

Mass spectrum (ESI⁺): m/z=415 [M+H]⁺

(13) 3,5-dichloro-N-(1H-indazol-5-yl)-phenylsulphonamide

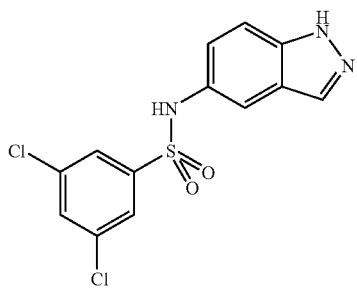

The product additionally contains 3,5-dichloro-N-[1-(3,5-dichloro-phenylsulphonyl)-3-methyl-1H-indazol-5-yl]-phenylsulphonamide.

Mass spectrum (ESI⁻): m/z=340 [M−H]⁻

R$_f$ value: 0.60 (silica gel: ethyl acetate/petroleum ether 2:1)

(14) 3-chloro-N-(9-ethyl-9H-carbazol-3-yl)-5-trifluoromethylsulphonyloxy-phenylsulphonamide

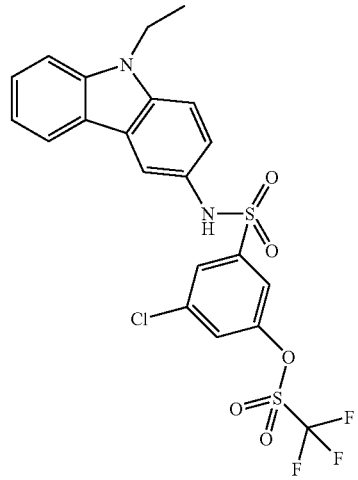

Mass spectrum (ESI⁺): m/z=533 [M+H]⁺

(15) tert-butyl 3-(tert-butoxycarbonyl-methyl-aminocarbonyl)-6-(3,5-dichloro-phenylsulphonylamino)-indole-1-carboxylate

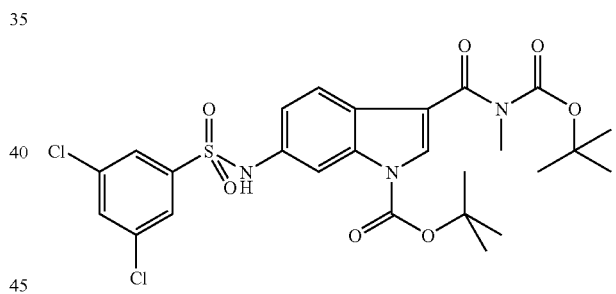

R$_f$ value: 0.63 (silica gel: petroleum ether/ethyl acetate 2:1)

(16) 3,5-dichloro-N-(9-ethyl-9H-carbazol-3-yl)-phenylsulphonamide

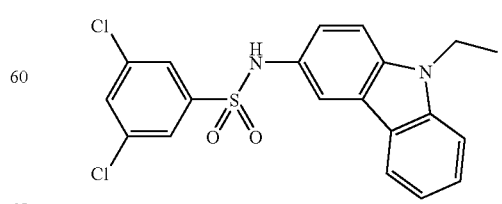

Mass spectrum (ESI⁺): m/z=533 [M+H]⁺

(17) N-[9-(2-phenylsulphonyl-ethyl)-9H-carbazol-3-yl]-3,5-dichloro-phenylsulphonamide

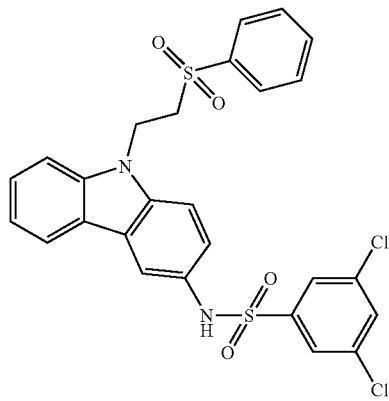

Mass spectrum (ESI+): m/z=576 [M+NH4]+

(18) methyl 5-(3,5-dichloro-phenylsulphonylamino)-benzo[b]thiophen-2-carboxylate

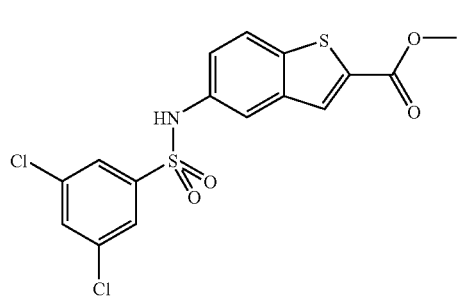

Mass spectrum (ESI+): m/z=433 [M+NH4]+

(19) N-(9H-carbazol-3-yl)-3,5-dichloro-phenylsulphonamide

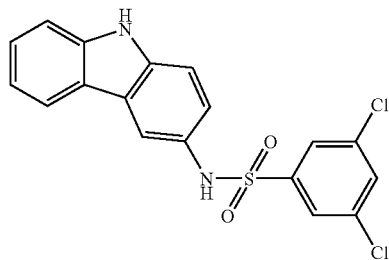

Mass spectrum (ESI−): m/z=389 [M−H]−

(20) methyl 6-(3,5-dichloro-phenylsulphonylamino)-1H-indole-3-carboxylate

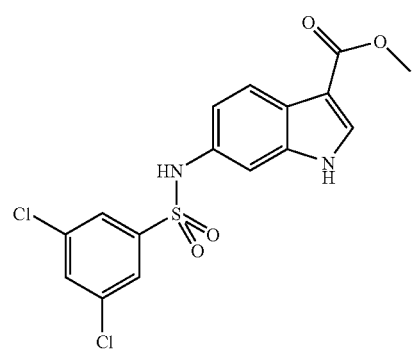

Mass spectrum (ESI+): m/z=399 [M+H]+

(21) 3,5-dichloro-N-[1-(phenylethyl)-1H-benzimidazol-5-yl]-phenylsulphonamide

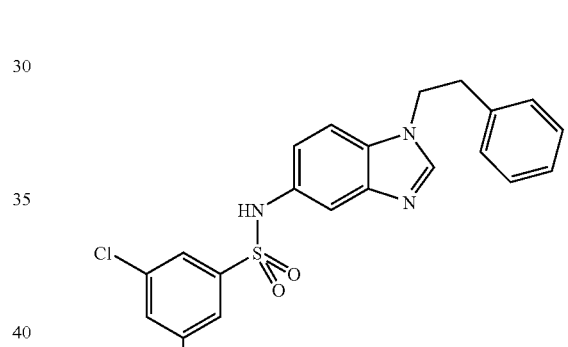

and 3,5-dichloro-N-[3-(phenylethyl)-3H-benzimidazol-5-yl]-phenylsulphonamide

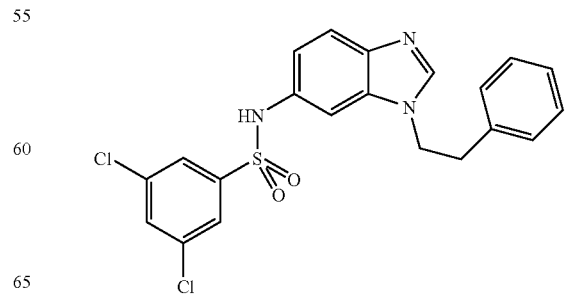

are obtained as a mixture and used as such in VI (29). Mass spectrum (ESI⁺): m/z=446 [M+H]⁺

(22) ethyl 5-(3,5-dichloro-phenylsulphonylamino)-1H-indole-2-carboxylate

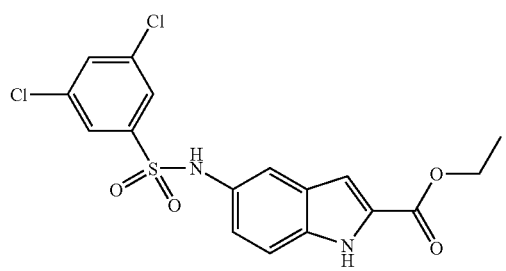

The reaction is carried out in dichloromethane. 1.4 equivalents 2,6-lutidine are used as the base.

Mass spectrum (ESI⁻): m/z=411 [M−H]⁻

(23) tert-butyl 6-(3,5-dichloro-phenylsulphonylamino)-3-(morpholine-4-carbonyl)-indole-1-carboxylate

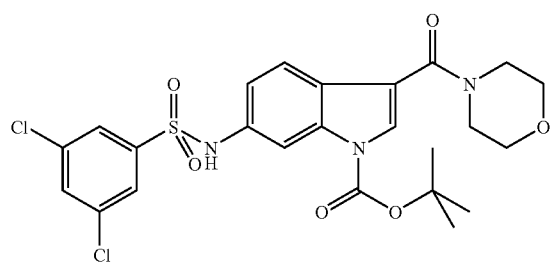

$R_f$ value: 0.41 (silica gel: petroleum ether/ethyl acetate 1:1)

(24) tert-butyl 3-(4-tert-butoxycarbonyl-piperazin-1-carbonyl)-6-(3,5-dichloro-phenylsulphonylamino)-indole-1-carboxylate

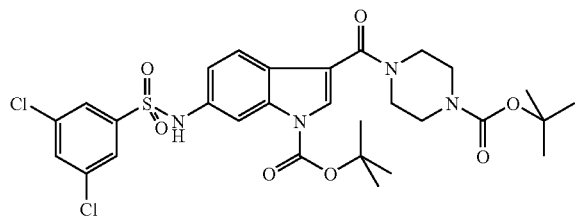

$R_f$ value: 0.63 (silica gel: petroleum ether/ethyl acetate 1:1)

(25) tert-butyl 3-(benzyl-tert-butoxycarbonyl-aminocarbonyl)-6-(3,5-dichloro-phenylsulphonylamino)-indole-1-carboxylate

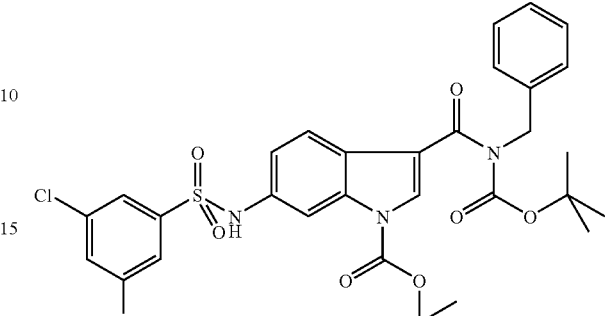

$R_f$ value: 0.65 (silica gel: petroleum ether/ethyl acetate 2:1)

(26) tert-butyl 3-(bis-tert.-butyloxycarbonyl)-aminocarbonyl-6-(3,5-dichloro-phenylsulphonylamino)-indole-1-carboxylate

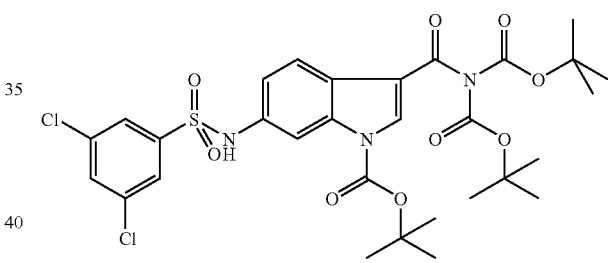

$R_f$ value: 0.67 (silica gel: petroleum ether/ethyl acetate 2:1)

(27) tert-butyl 3-(tert-butoxycarbonyl-phenyl-aminocarbonyl)-6-(3,5-dichloro-phenylsulphonylamino)-indole-1-carboxylate

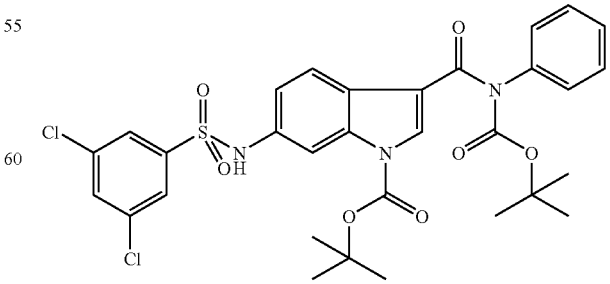

$R_f$ value: 0.74 (silica gel: petroleum ether/ethyl acetate 2:1)

(28) 3,5-dichloro-N-(3-cyano-1-methyl-1H-indol-6-yl)-phenylsulphonamide

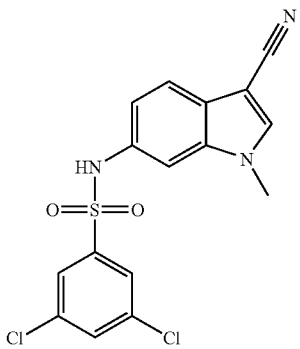

Mass spectrum (ESI⁻): m/z=378 [M−H]⁻

(29) 5-(3,5-dichloro-phenylsulphonylamino)-benzo[b]thiophen-3-carboxylic acid-methylamide

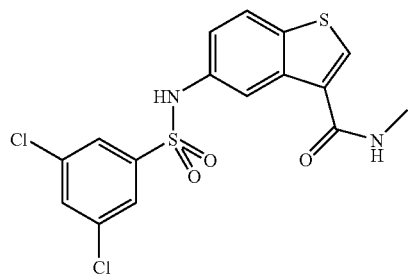

Mass spectrum (ESI⁻): m/z=413 [M−H]⁻

(30) 6-(3,5-dichloro-phenylsulphonylamino)-benzo[b]thiophen-3-carboxylic acid-methylamide

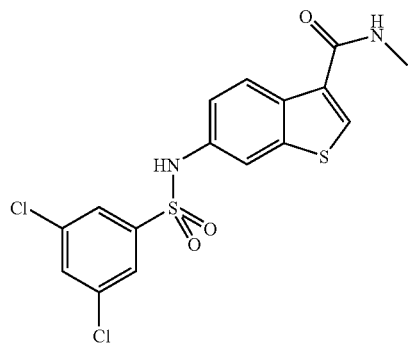

Mass spectrum (ESI⁺): m/z=415 [M+H]⁺

(31) tert-butyl 3-(4-tert-butoxycarbonyl-3-oxo-piperazin-1-carbonyl)-6-(3,5-dichloro-phenylsulphonylamino)-indole-1-carboxylate

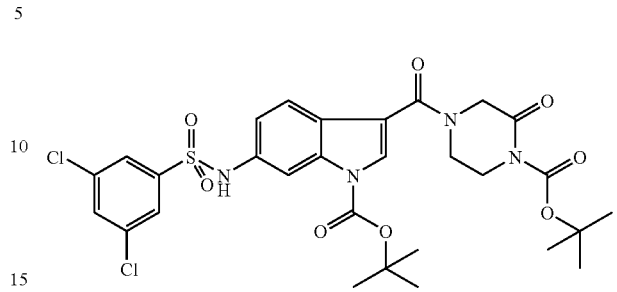

R$_f$ value: 0.73 (silica gel: petroleum ether/ethyl acetate 1:1)

(32) 6-(3,5-dichloro-phenylsulphonylamino)-1H-indole-3-carboxylic acid-(1-methyl carbamoyl-ethyl)-amide

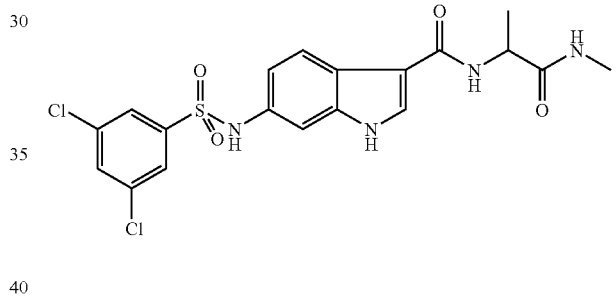

R$_f$ value: 0.35 (silica gel: dichloromethane/methanol 9:1)

(33) 5-(3,5-dimethyl-phenylsulphonylamino)-2,3-dihydro-indole-1-carboxylic acid-methylamide

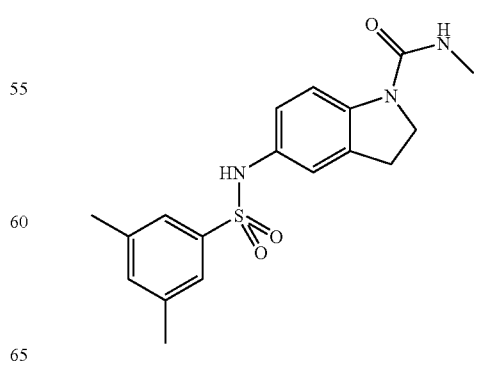

Mass spectrum (ESI⁺): m/z=360 [M+H]⁺

81

(34) tert-butyl 6-(3,5-dichloro-phenylsulphony-lamino)-3-dimethylcarbamoyl-indole-1-carboxylate

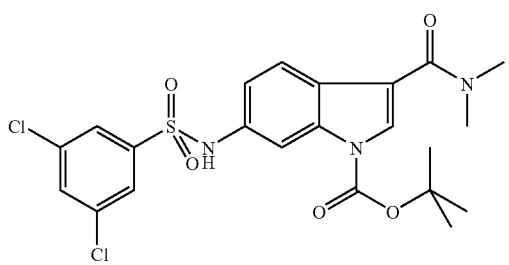

R$_f$ value: 0.60 (silica gel: petroleum ether/ethyl acetate 1:2)

(35) 3,5-dichloro-N-(1-methyl-1H-indol-6-yl)-phenylsulphonamide

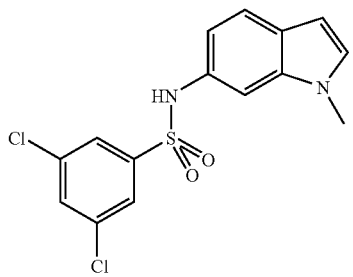

Mass spectrum (ESI$^+$): m/z=355 [M+H]$^+$

(36) 3,5-dichloro-N-(1,3-dimethyl-2-oxo-2,3-dihydro-1H-benzimidazol-5-yl)-phenylsulphonamide

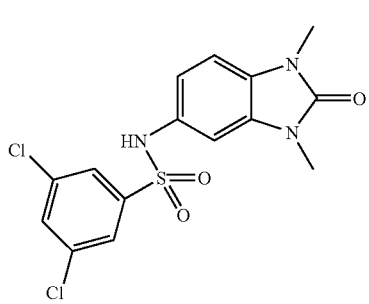

Mass spectrum (ESI$^+$): m/z=386 [M+H]$^+$

82

(37) 1-tert-butyl-3-methyl 5-(3,5-dichloro-phenylsulphonylamino)-2,3-dihydro-indole-1,3-dicarboxylate

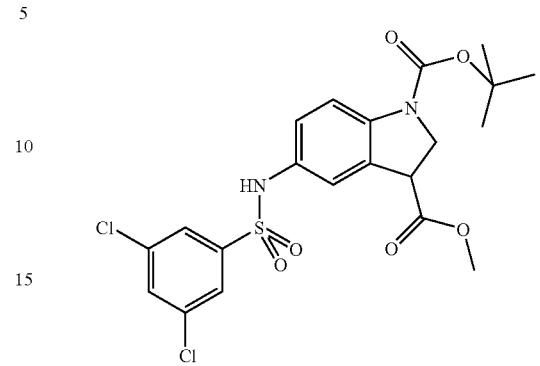

R$_f$ value: 0.30 (silica gel: petroleum ether/ethyl acetate 3:1)

(38) 3-chloro-5-methyl-N-[1-methyl-3-(pyrrolidine-1-carbonyl)-1H-indol-6-yl]-phenylsulphonamide

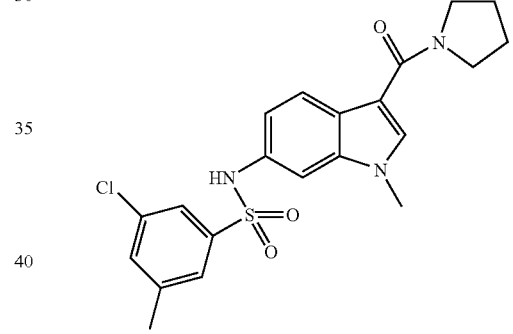

Mass spectrum (ESI$^+$): m/z=432 [M+H]$^+$

(39) 3,5-dimethyl-N-[1-methyl-3-(pyrrolidine-1-carbonyl)-1H-indol-6-yl]-phenylsulphonamide

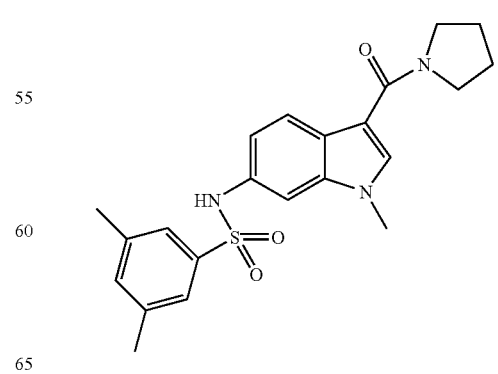

Mass spectrum (ESI$^+$): m/z=412 [M+H]$^+$

(40) 3,5-dichloro-N-[1-methyl-3-(pyrrolidine-1-carbonyl)-1H-indazol-6-yl]-phenylsulphonamide

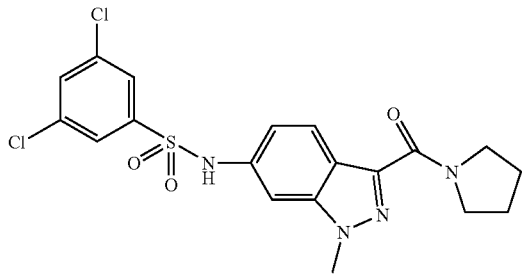

Mass spectrum (ESI$^+$): m/z=453 [M+H]$^+$

(41) 6-(3,5-dichloro-phenylsulphonylamino)-1-methyl-1H-indazol-3-carboxylic acid-methylamide

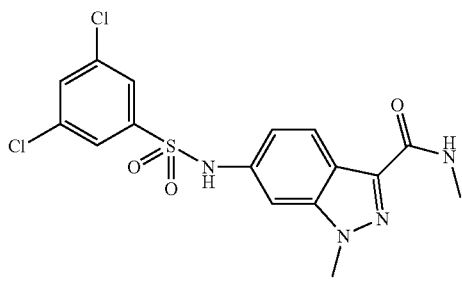

Mass spectrum (ESI$^+$): m/z=413 [M+H]$^+$

(42) 6-(3,5-dichloro-phenylsulphonylamino)-benzo[b]thiophen-3-carboxylic acid-amide

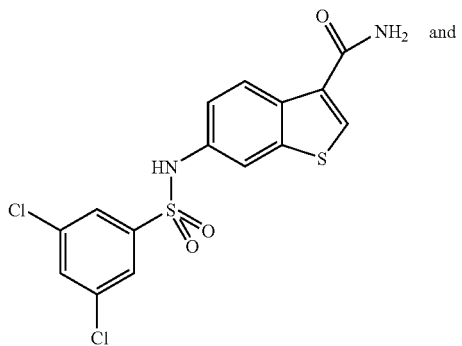

5-(3,5-dichloro-phenylsulphonylamino)-benzo[b]thiophen-3-carboxylic acid-amide

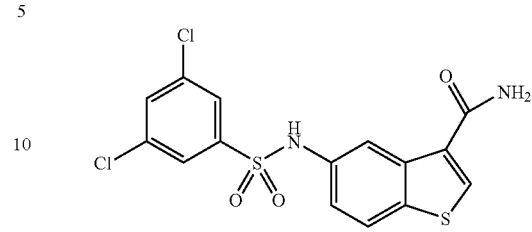

Obtained from the reaction of a mixture of 6-amino-benzo[b]thiophene-3-carboxylic acid-amide and 5-amino-benzo[b]thiophene-3-carboxylic acid-amide (Example XII (30)). The crude product is dissolved in hot ethyl acetate. After cooling to ambient temperature the precipitated solid (5-(3,5-dichloro-phenylsulphonylamino)-benzo[b]thiophene-3-carboxylic acid-amide) is filtered off. The mother liquor is freed from the solvents in vacuo and the residue is chromatographed on silica gel, to obtain 6-(3,5-dichloro-phenylsulphonylamino)-benzo[b]thiophene-3-carboxylic acid-amide.

Mass spectrum (ESI$^+$): m/z=401 [M+H]$^+$ 6-(3,5-dichloro-phenylsulphonylamino)-benzo[b]thiophene-3-carboxylic acid-amide and 5-(3,5-dichloro-phenylsulphonylamino)-benzo[b]thiophene-3-carboxylic acid-amide

EXAMPLE XII

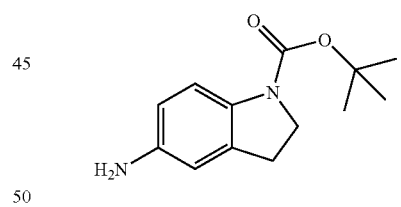

tert-butyl 5-amino-2,3-dihydro-indole-1-carboxylate 6.8 g tert-butyl 5-nitro-indole-1-carboxylate are dissolved in 120 ml of methanol. 600 mg palladium on charcoal (10%) are added thereto and the mixture is hydrogenated for 1.5 hours at ambient temperature. Then the catalyst is filtered off and the solvent is eliminated in vacuo.

Yield: 6 g (100% of theory)

Mass spectrum (ESI$^+$): m/z=235 [M+H]$^+$

The following compounds are obtained analogously to Example XII:

(1) 5-amino-2,3-dihydro-indole-1-carboxylic acid-methylamide

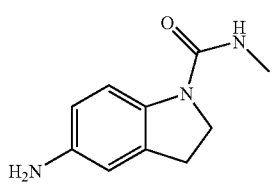

Mass spectrum (ESI$^+$): m/z=192 [M+H]$^+$ (2) 4-amino-2,3-dihydro-indole-1-carboxylic acid-methylamide

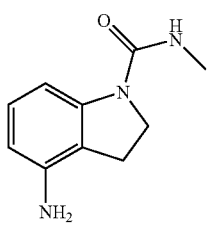

Mass spectrum (ESI$^+$): m/z=192 [M+H]$^+$ (3) 4-amino-2,3-dihydro-indole-1-carboxylic acid-phenylamide

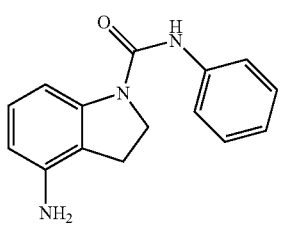

Mass spectrum (ESI$^+$): m/z=254 [M+H]$^+$ (4) 4-amino-2,3-dihydro-indole-1-carboxylic acid-pyridin-3-ylamide

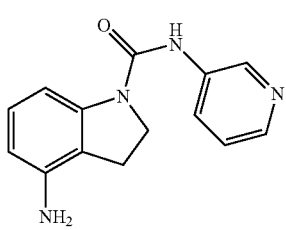

Mass spectrum (ESI$^+$): m/z=255 [M+H]$^+$ (5) 1-(5-amino-2-ethyl-phenyl)-1-methyl-3-phenyl-urea

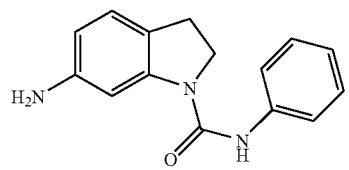

The crude product is extracted from diisopropylether.
Mass spectrum (ESI$^+$): m/z=254 [M+H]$^+$ (6) 9H-carbazol-3-ylamine

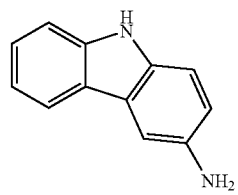

Tetrahydrofuran is used as solvent.
Mass spectrum (ESI$^+$): m/z=183 [M+H]$^+$ (7) 1-chloro-3-methoxy-5-amino-benzene

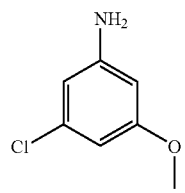

Tetrahydrofuran is used as solvent.
Mass spectrum (ESI$^+$): m/z=158 [M+H]$^+$ (8) 3-amino-5-chloro-phenyl trifluoromethanesulphonate

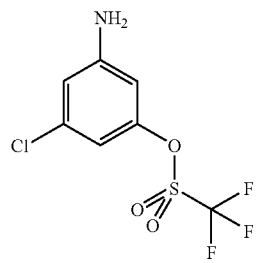

Tetrahydrofuran is used as solvent
The product is further reacted directly in XVII (2). .

(9) tert-butyl 6-amino-3-(tert-butoxycarbonyl-methyl-aminocarbonyl)-indole-1-carboxylate

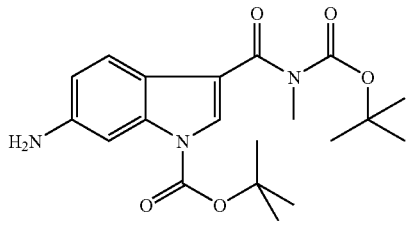

Tetrahydrofuran is used as solvent.
$R_f$ value: 0.42 (silica gel: petroleum ether/ethyl acetate 2:1)

(10) 9-(2-phenylsulphonyl-ethyl)-9H-carbazol-3-ylamine

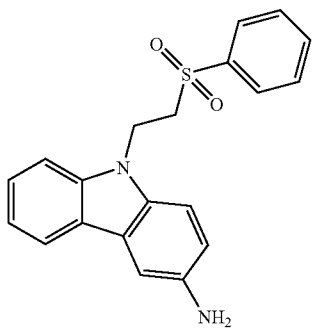

Mass spectrum (ESI$^+$): m/z=351 [M+H]$^+$

(11) 9H-carbazol-3-ylamine

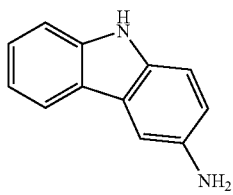

Mass spectrum (ESI$^+$): m/z=183 [M+H]$^+$

(12) ethyl 5-amino-1H-indole-2-carboxylate

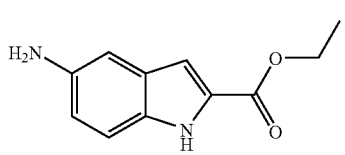

A 3:2:2 mixture of ethyl acetate, methanol and tetrahydrofuran is used as solvent.
Mass spectrum (ESI$^+$): m/z=205 [M+H]$^+$

(13) tert-butyl 6-amino-3-(morpholine-4-carbonyl)-indole-1-carboxylate

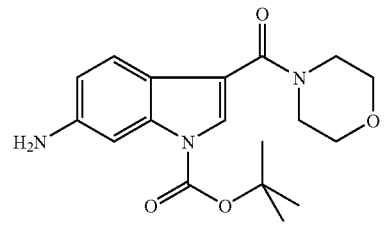

Tetrahydrofuran is used as solvent.
$R_f$ value: 0.21 (silica gel: petroleum ether/ethyl acetate 1:1)

(14) tert-butyl 6-amino-3-(4-tert-butoxycarbonyl-piperazin-1-carbonyl)-indole-1-carboxylate

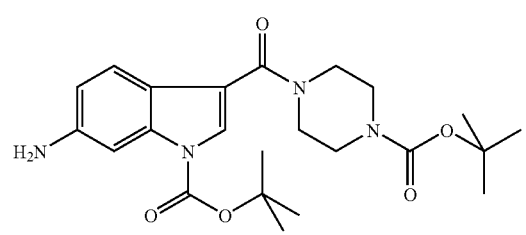

Tetrahydrofuran is used as solvent.
$R_f$ value: 0.33 (silica gel: petroleum ether/ethyl acetate 1:1)

(15) tert-butyl 6-amino-3-(benzyl-tert-butoxycarbonyl-aminocarbonyl)-indole-1-carboxylate

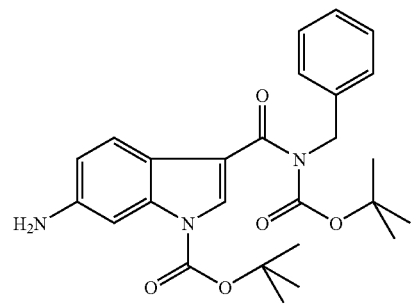

Tetrahydrofuran is used as solvent.
$R_f$ value: 0.44 (silica gel: petroleum ether/ethyl acetate 2:1)

(16) tert-butyl 6-amino-3-(bis-tert-butoxycarbonyl)-aminocarbonyl-indole-1-carboxylate

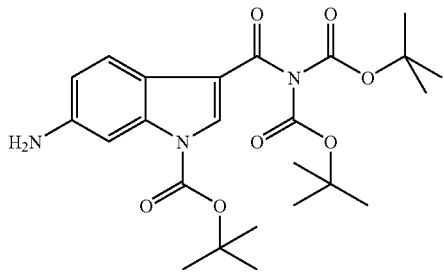

Tetrahydrofuran is used as solvent.
$R_f$-value: 0.62 (silica gel: petroleum ether/ethyl acetate 2:1)

(17) tert-butyl 6-amino-3-(tert-butoxycarbonyl-phenyl-aminocarbonyl)-indole-1-carboxylate

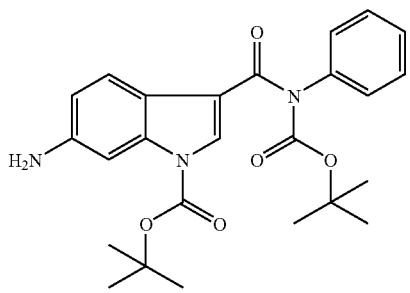

Tetrahydrofuran is used as solvent.
$R_f$-value: 0.45 (silica gel: petroleum ether/ethyl acetate 2:1)

(18) 6-amino-1-methyl-1H-indole-3-carbonitrile

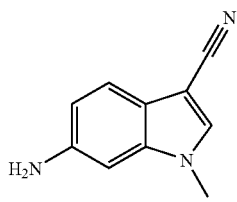

The crude product is crystallised from isopropanol.
Mass spectrum (ESI$^+$): m/z=172 [M+H]$^+$

(19) 5-amino-benzo[b]thiophene-3-carboxylic acid-methylamide

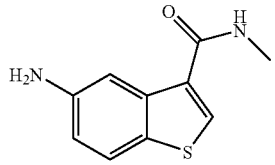

Tetrahydrofuran/methanol 2:1 is used as solvent. The crude product is further reacted directly in XI (29).

(20) 6-amino-benzo[b]thiophene-3-carboxylic acid-methylamide

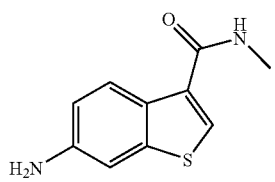

Tetrahydrofuran/methanol 2:1 is used as solvent. The crude product is further reacted directly in XI (30).

(21) tert-butyl 6-amino-3-(4-tert-butoxycarbonyl-3-oxo-piperazin-1-carbonyl)-indole-1-carboxylate

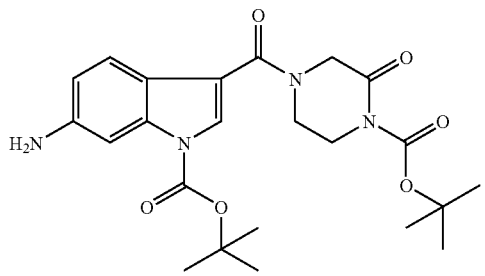

Tetrahydrofuran is used as solvent.
$R_f$-value: 0.54 (silica gel: petroleum ether/ethyl acetate 1:1)

(22) 6-amino-1H-indole-3-carboxylic acid-(1-methylcarbamoyl-ethyl)amide

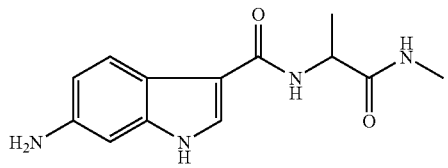

Tetrahydrofuran is used as solvent
$R_f$-value: 0.46 (silica gel: dichloromethane/methanol 5:1).

(23) tert-butyl 6-amino-3-dimethylcarbamoyl-indole-1-carboxylate

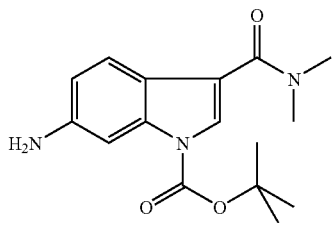

Tetrahydrofuran is used as solvent.
$R_f$ value: 0.32 (silica gel: petroleum ether/ethyl acetate 1:2)

(24) 1-methyl-1H-indol-6-ylamine

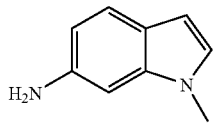

Tetrahydrofuran is used as solvent.
Mass spectrum (ESI$^+$): m/z=147 [M+H]$^+$

(25) 5-amino-1,3-dimethyl-1,3-dihydro-benzimidazol-2-one

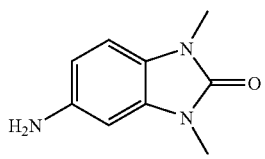

Tetrahydrofuran is used as solvent.
Mass spectrum (ESI$^+$): m/z=178 [M+H]$^+$

(26) 1-tert-butyl-3-methyl 5-amino-2,3-dihydro-indole-1,3-dicarboxylate

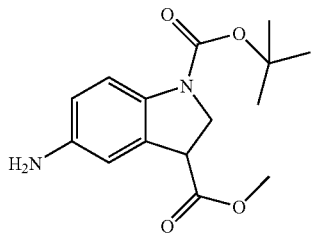

Obtained from the hydrogenation of 1-tert-butyl-3-methyl 5-nitro-indole-1,3-dicarboxylate in ethyl acetate/methanol/tetrahydrofuran 10:7:7. It is hydrogenated at 50° C. and 15 bar.
$R_f$ value: 0.30 (silica gel: petroleum ether/ethyl acetate 1:1)

(27) (6-amino-1-methyl-1H-indol-3-yl)-pyrrolidin-1-yl-methanone

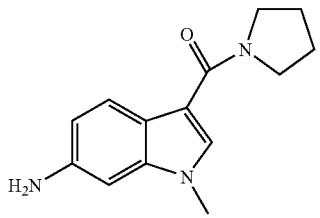

Mass spectrum (ESI$^+$): m/z=244 [M+H]$^+$

(28) (6-amino-1-methyl-1H-indazol-3-yl)-pyrrolidin-1-yl-methanone

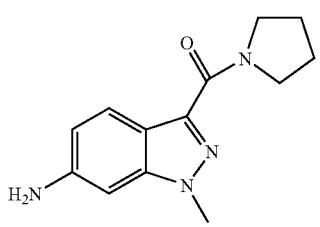

$R_f$ value: 0.40 (silica gel: dichloromethane/methanol 95:5)

(29) 6-amino-1-methyl-1H-indazol-3-carboxylic acid-methylamide

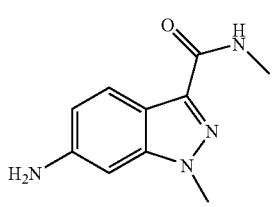

$R_f$ value: 0.40 (silica gel: dichloromethane/methanol 95:5)

(30) 6-amino-benzo[b]thiophene-3-carboxylic acid-amide

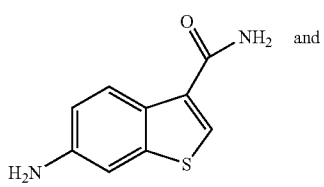

5-amino-benzo[b]thiophene-3-carboxylic acid-amide

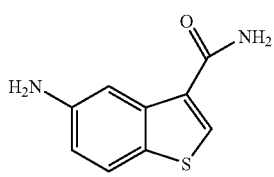

Obtained as a mixture from the reaction of a mixture of 6-nitro-benzo[b]thiophene-3-carboxylic acid-amide and 5-nitro-benzo[b]thiophene-3-carboxylic acid-amide (Example IXXX (9)). The crude product is further reacted directly in Example XI (42).

EXAMPLE XIII tert-butyl 5-(3,5-dichloro-phenylsulphonylamino)-2,3-dihydro-indole-1-carboxylate

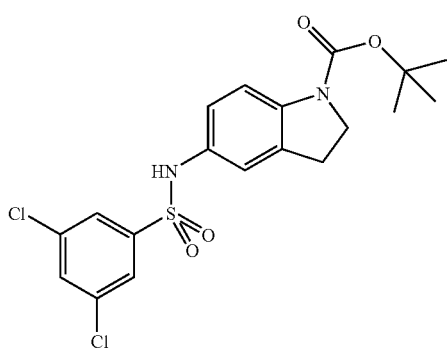

6.6 g tert-butyl 5-nitro-2,3-dihydro-indole-1-carboxylate are dissolved in 120 ml of methanol. 600 mg palladium on charcoal (10%) are added and the mixture is hydrogenated until no more educt can be detected by thin layer chromatography. The catalyst is suction filtered and washed with methanol. The solvent is eliminated in vacuo and the residue is taken up in 30 ml of pyridine. 6.1 g of 3,5-dichlorophenylsulphonyl chloride are added and the mixture is stirred for 5 hours at ambient temperature. Then the pyridine is eliminated in vacuo and the residue is divided between 1 N HCl and ethyl acetate. The organic phase is washed with saturated sodium hydrogen carbonate solution and with saturated sodium chloride solution. After drying with magnesium sulphate the solvent is eliminated in vacuo.

Yield: 11 g (99% of theory)

Mass spectrum (ESI$^-$): m/z=441 [M−H]$^-$

The following compounds are obtained analogously to Example XIII:

(1) 3,5-dichloro-N-(1-phenylacetyl-1H-indol-5-yl)-phenylsulphonamide

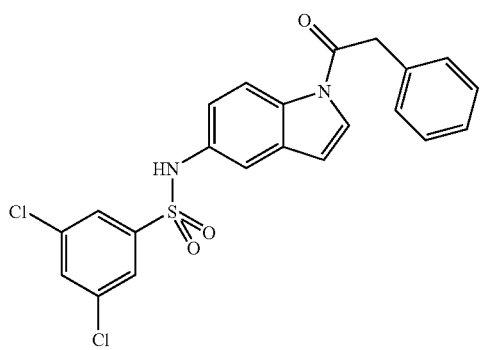

and 3,5-dichloro-N-(1-phenylacetyl-2,3-dihydro-1H-indol-5-yl)-phenylsulphonamide

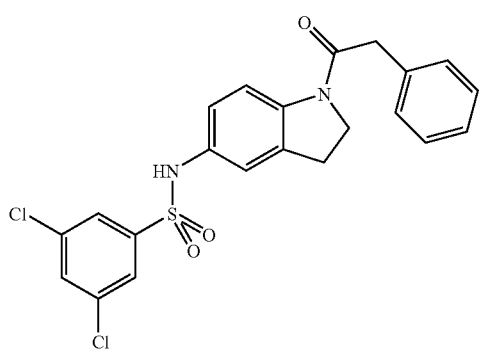

The hydrogenation is carried out in the presence of 1.2 equivalents of 1 N HCl. The crude product is chromatographed on silica gel.

Mass spectrum (ESI⁻): m/z=457 [M−H]⁻ (3,5-dichloro-N-(1-phenylacetyl-1H-indol-5-yl)-phenylsulphonamide)

Mass spectrum (ESI⁻): m/z=459 [M−H]⁻ (3,5-dichloro-N-(1-phenylacetyl-2,3-dihydro-1H-indol-5-yl)-phenylsulphonamide)

(2) 3,5-dichloro-N-[1-(phenylethyl)-1H-indol-5-yl]-phenylsulphonamide

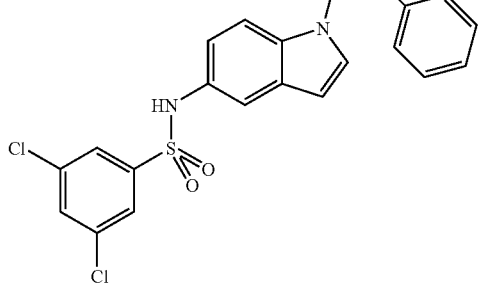

Mass spectrum (ESI⁺): m/z=445 [M+H]⁺

EXAMPLE XIV

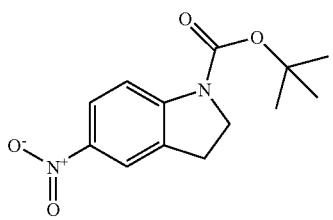

tert-butyl 5-nitro-2,3-dihydro-indole-1-carboxylate 5 g 5-nitro-2,3-dihydro-1H-indole are dissolved in 70 ml acetonitrile. 7.3 g di-tert-butyl-dicarbonate and 900 mg 4-dimethylaminopyridine are added thereto. After stirring for 24 hours at ambient temperature the mixture is divided between 1 N HCl and ethyl acetate. The aqueous phase is extracted with ethyl acetate and the combined organic phases are washed with saturated sodium hydrogen carbonate solution and saturated sodium chloride solution. After drying with magnesium sulphate the solvents are eliminated in vacuo. The residue is extracted from diisopropylether/petroleum ether.

Yield: 6.6 g (82% of theory)

Mass spectrum (ESI⁺): m/z=265 [M+H]⁺

EXAMPLE XV

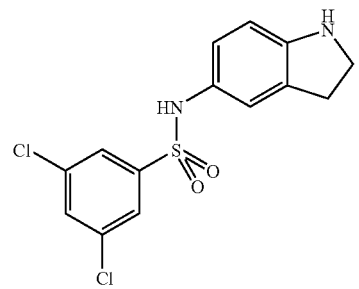

3,5-dichloro-N-(2,3-dihydro-1H-indol-5-yl)-indolsulphonamide 4.08 g tert-butyl 5-(3,5-dichloro-phenylsulphonylamino)-2,3-dihydro-indole-1-carboxylate are dissolved in 70 ml dichloromethane. To this are added 25 ml trifluoroacetic acid and the solution is stirred for 2 hours at ambient temperature. The solvents are eliminated in vacuo and the residue is divided between saturated sodium hydrogen carbonate solution and ethyl acetate. The aqueous phase is extracted with ethyl acetate and the combined organic phases are washed with saturated sodium chloride solution. After drying with magnesium sulphate the solvents are eliminated in vacuo.

Yield: 3.0 g (97% of theory)

Mass spectrum (ESI⁻): m/z=341 [M−H]⁻

The following compounds are obtained analogously to Example XV:

(1) methyl 5-(3,5-dichloro-phenylsulphonylamino)-2,3-dihydro-1H-indole-3-carboxylate

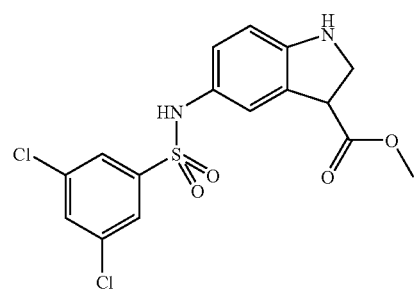

$R_f$ value: 0.50 (silica gel: petroleum ether/ethyl acetate 1:1)

EXAMPLE XVI

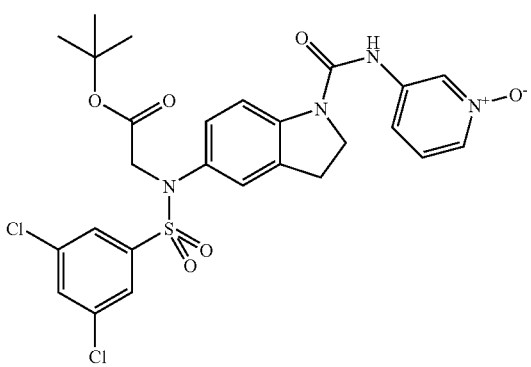

tert.butyl {(3,5-dichloro-phenylsulphonyl)-[1-(1-oxy-pyridin-3-ylcarbamoyl)-2,3-dihydro-1H-indol-5-yl]-amino}-acetate 85 mg tert.butyl {(3,5-dichloro-phenylsulphonyl)-[1-(pyridin-3-ylcarbamoyl)-2,3-dihydro-1H-indol-5-yl]-amino}-acetate are dissolved in 3 ml dichloromethane and 100 mg 3-chloro-perbenzoic acid are added. The mixture is stirred overnight at ambient temperature, diluted with ethyl acetate and washed with saturated sodium hydrogen carbonate solution and saturated sodium chloride solution. After drying with magnesium sulphate the solvents are eliminated in vacuo and the residue is chromatographed on silica gel (dichloromethane/methanol 99:1 to 4:1).

Yield: 75 mg (86% of theory)
Mass spectrum (ESI⁻): m/z=591 [M−H]⁻

EXAMPLE XVII

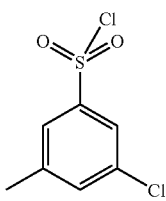

3-chloro-5-methyl-phenylsulphonyl-chloride 300 mg 3-chloro-5-methyl-phenylamine are dissolved in 1 ml concentrated HCl and cooled to 0° C. A solution of 170 mg sodium nitrite in 0.3 ml of water is added dropwise thereto. The solution thus prepared is added dropwise at 0° C. to a solution of 85 mg copper-II-chloride, 0.3 ml of water and 7 ml sulphur dioxide in glacial acetic acid (30%). The cooling bath is removed and the mixture is stirred for another 20 minutes at ambient temperature. Then it is heated to 40° C. for 10 minutes. It is then diluted with ice water, the solid is suction filtered and dried in the desiccator. The product is further reacted directly in Example XI without any further purification.

Yield: 370 mg (78% of theory)

The following compounds are obtained analogously to Example XVII:

(1) 3-chloro-5-methoxy-phenylsulphonyl chloride

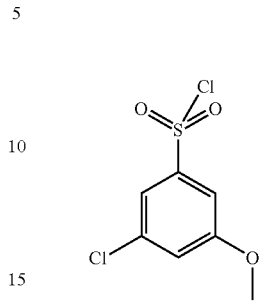

The aqueous phase is twice extracted with ethyl acetate. The combined organic phases are dried on magnesium sulphate and the solvent is eliminated in vacuo.

R$_f$ value: 0.95 (silica gel; dichloromethane)

(2) 3-chloro-5-chlorosulphonyl-phenyl trifluoromethanesulphonate

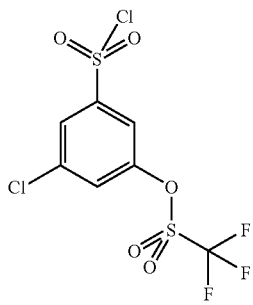

The product is further reacted directly in Example XI(14) without any further purification.

EXAMPLE XVIII

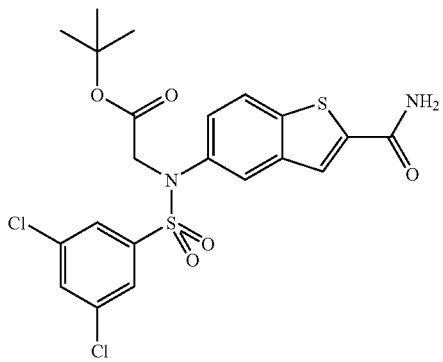

tert.butyl[(2-carbamoyl-benzo[b]thiophene-5-yl)-(3,5-dichloro-phenylsulphonyl)-amino]-acetate 250 mg methyl 5-[tert-butoxycarbonylmethyl-(3,5-dichloro-phenylsulphonyl)-amino]-benzo[b]thiophen-2-carboxylate are dissolved in 30 ml ammonia-saturated methanol and stirred for 24 hours at ambient temperature. Then the solution is heated to 80° C. in a pressurised vessel for 8 hours. Then the solvent is eliminated in vacuo and the residue is extracted from diisopropylether. The product thus obtained is chromatographed on silica gel with cyclohexane/ethyl acetate (9:1 to 1:4).

Yield: 141 mg (58% of theory)
Mass spectrum (ESI+): m/z=515 [M+H]+

EXAMPLE IXX

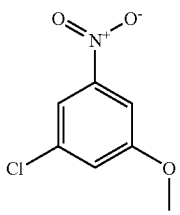

1-chloro-3-methoxy-5-nitro-benzene 10 g 3-chloro-5-nitrophenol are dissolved in 250 ml of ethanol. 11.9 g potassium carbonate and 6 ml dimethylsulphate are added and the mixture is stirred for 12 hours at ambient temperature. Then 3 ml of a 33% ammonia solution are added and then the ethanol is eliminated in vacuo. The residue is taken up in water and the precipitated solid is suction filtered and dried.

Yield: 10.37 g (96% of theory)
Mass spectrum (EI): m/z=187 [M]+

EXAMPLE XX

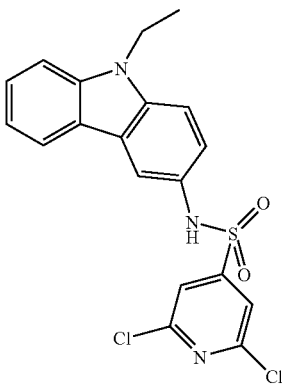

2,6-dichloro-pyridine-4-sulphonic acid-(9-ethyl-9H-carbazol-3-yl)-amide 2 g 4-amino-2,6-dichloropyridine are dissolved in 8 ml concentrated HCl and cooled to 0° C. A solution of 900 mg sodium nitrite in 2 ml of water is added dropwise thereto. The solution thus prepared is added dropwise at 0° C. to a solution of 550 mg copper-II-chloride, 1 ml of water and 10 ml sulphur dioxide in glacial acetic acid (30%). The cooling bath is removed and the mixture is stirred for 15 minutes at ambient temperature. Then it is diluted with ice water and the solid is suction filtered. The aqueous phase is extracted with ethyl acetate. The solid filtered off is dissolved in ethyl acetate. The combined ethyl acetate phases are dried on magnesium sulphate and the solvent is eliminated in vacuo. 1.2 g of (9-ethyl-9H-carbazol-3-yl)-methyl-amine and 15 ml of pyridine are added to the residue. The mixture is stirred for 12 hours at ambient temperature, the solvent is eliminated in vacuo and the residue is chromatographed on silica gel with dichloromethane.

Yield: 210 mg (10% of theory)
Mass spectrum (ESI−): m/z=418 [M−H]−

EXAMPLE XXI

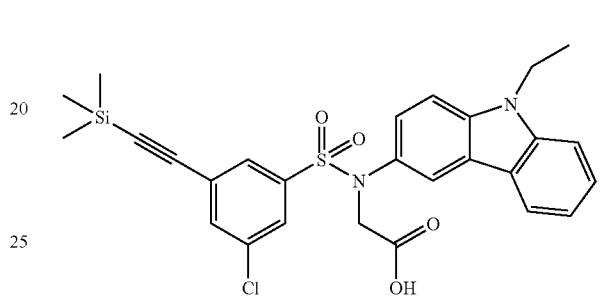

[(3-chloro-5-trimethylsilylethynyl-Phenylsulphonyl)-(9-ethyl-9H-carbazol-3-yl)-amino]-acetic acid 180 mg tert-butyl [(3-chloro-5-trimethylsilylethynyl-phenylsulphonyl)-(9-ethyl-9H-carbazol-3-yl)-amino]-acetate are dissolved in 5 ml dichloromethane. 1 ml of trifluoroacetic acid is added with stirring. The mixture is stirred overnight at ambient temperature and then the solvents are eliminated in vacuo. The residue is chromatographed on silica gel (dichloromethane/methanol 100:0 to 95:5).

Yield: 134 mg (74% of theory)
Mass spectrum (ESI−): m/z=537 [M−H]−

EXAMPLE XXII

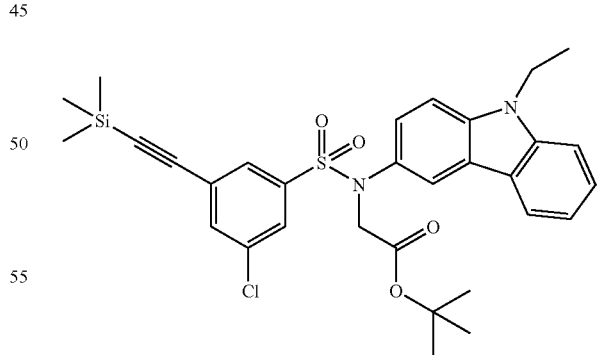

tert-butyl[(3-chloro-5-trimethylsilylethynyl-Phenylsulphonyl)-(9-ethyl-9H-carbazol-3-yl)-amino]-acetate 320 mg tert-butyl [(3-chloro-5-trifluoromethylsulphonyloxy-phenylsulphonyl)-(9-ethyl-9H-carbazol-3-yl)-amino]-acetate are dissolved in 4 ml dimethylformamide. 20 mg copper-1-iodide, 40 mg bis-triphenylphosphine-palladium-dichloride and 210 μl trimethylsilylacetylene are added under argon. Then the mixture is heated to 60° C. for 6 hours and then stirred overnight at ambient temperature. The mixture is then divided between saturated potassium carbonate solution and ethyl acetate. The organic phase is dried on magnesium sulphate and the solvents are eliminated in vacuo. The residue is chromatographed on silica gel (dichloromethane/methanol 100:0 to 95:5).

Yield: 223 mg (76% of theory)
Mass spectrum (ESI$^+$): m/z=595 [M+H]$^{30}$

EXAMPLE XXIII

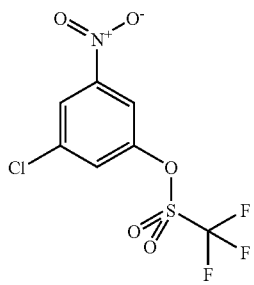

3-chloro-5-nitro-phenyl trifluoromethanesulphonate 2.2 g 3-chloro-5-nitrophenol are dissolved in 30 ml dichloromethane, combined with 1.1 ml of pyridine and cooled to −10° C. A solution of 2.2 ml trifluoromethanesulphonic acid anhydride in 5 ml dichloromethane is added thereto, the mixture is left overnight to warm up to ambient temperature and then divided between dichloromethane and saturated sodium hydrogen carbonate solution. The organic phase is washed with saturated sodium chloride solution and dried on magnesium sulphate. The solvent is eliminated in vacuo.

Yield: 3.5 g (81% of theory)
R$_f$ value: 0.90 (silica gel: dichloromethane)

EXAMPLE XXIV

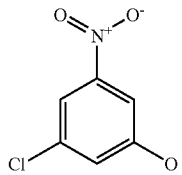

3-chloro-5-nitrophenol 1.65 g 3-chloro-5-nitroanisole are combined with 20.3 g pyridinium hydrochloride and heated to 200° C. for 1 hour. Then the mixture is left overnight to come up to ambient temperature, 200 ml of water are added, the precipitated solid is suction filtered and dried in vacuo.

Yield: 860 mg (56% of theory)
Mass spectrum (ESI$^-$): m/z=162 [M−H]$^-$

EXAMPLE XXV

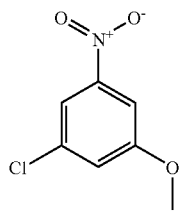

3-chloro-5-nitroanisol 11.1 g 1-chloro-3,5-dinitrobenzene are dissolved in 100 ml of methanol and combined with 3 g sodium methoxide. Then the mixture is refluxed for 48 hours, cooled to ambient temperature and the solid is suction filtered.

Yield: 2.27 g (22% of theory)
Mass spectrum (EI): m/z=187 [M]$^{30}$

EXAMPLE XXVI

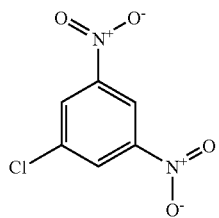

1-chloro-3,5-dinitrobenzene 18 g 3,5-dinitroaniline are suspended in 45 ml concentrated hydrochloric acid and 15 ml of water and cooled to 0° C. A solution of 7.6 g sodium nitrite in 25 ml of water is added dropwise thereto. Then the diazonium salt solution thus obtained is added dropwise at 0° C. to a solution of 13 g of copper-1-chloride in 45 ml concentrated hydrochloric acid. Then the mixture is refluxed for 10 minutes. After cooling to ambient temperature it is extracted 3 times with 150 ml of ethyl acetate and the combined organic phases are washed with water.

Then the mixture is dried on magnesium sulphate, the solvents are eliminated in vacuo and the residue is chromatographed on silica gel with petroleum ether/ethyl acetate.

Yield: 11.15 g (58% of theory)
Mass spectrum (EI): m/z=202 [M]$^{30}$

EXAMPLE XXVII

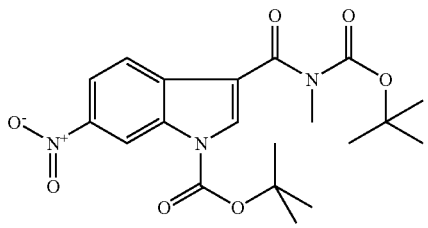

tert-butyl 3-(tert-butoxycarbonyl-methyl-aminocarbonyl)-6-nitro-indole-1-carboxylate 220 mg of 6-nitro-1H-indole-3-carboxylic acid-methylamide are dissolved in 10 ml of tetrahydrofuran. 350 mg di-tert.-butyl-dicarbonate are added thereto and the mixture is stirred for 3 hours at ambient temperature. Then the solvent is eliminated in vacuo and the residue is chromatographed on silica gel (cyclohexane/ethyl acetate 90:10 to 20:80)

Yield: 95 mg (23% of theory)

Mass spectrum (ESI$^+$): m/z=420 [M+H]$^+$

The following compounds are obtained analogously to Example XXVII:

(1) tert-butyl 3-(morpholine-4-carbonyl)-6-nitro-indole-1-carboxylate

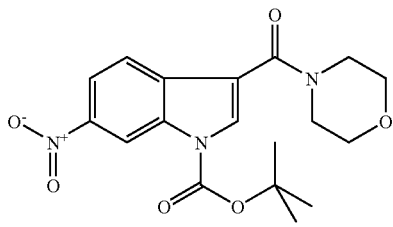

Mass spectrum (ESI$^+$): m/z=376 [M+H]$^+$ (2) tert-butyl 3-(4-tert-butoxycarbonyl-piperazine-1-carbonyl)-6-nitro-indole-1-carboxylate

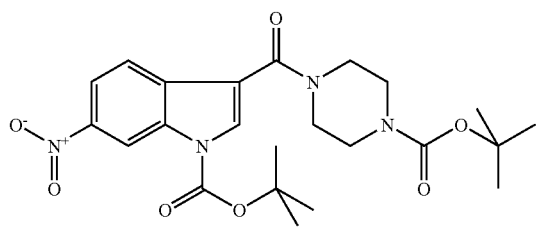

Mass spectrum (ESI$^+$): m/z=475 [M+H]$^+$ (3) tert-butyl 3-(benzyl-tert-butoxycarbonyl-aminocarbonyl)-6-nitro-indole-1-carboxylate

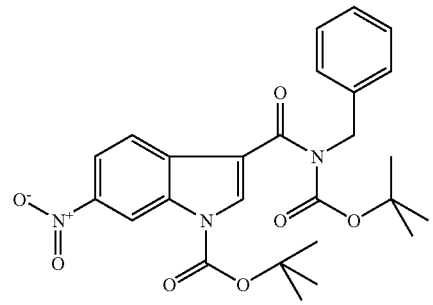

Mass spectrum (ESI$^+$): m/z=496 [M+H]$^+$ (4) tert-butyl 3-(bis-tert.-butoxycarbonyl)-aminocarbonyl-6-nitro-indole-1-carboxylate

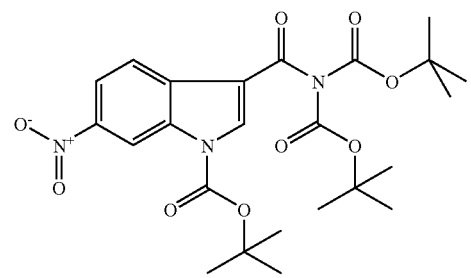

The reaction is carried out in the presence of a catalytic amount of 4-N,N-dimethylamino-pyridine at 60° C. The product is obtained in admixture with 3-(bis-tert.-butoxycarbonyl)-aminocarbonyl-6-nitro-1H-indole.

R$_f$ value: 0.50 (silica gel; petroleum ether/ethyl acetate 4:1)

(5) tert-butyl 3-(tert-butoxycarbonyl-phenyl-aminocarbonyl)-6-nitro-indole-1-carboxylate

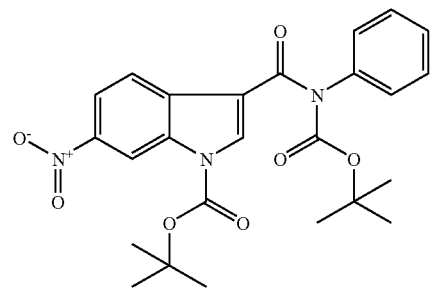

The reaction is carried out in the presence of a catalytic amount of 4-N,N-dimethylamino-pyridine at 60° C.

R$_f$ value: 0.39 (silica gel; petroleum ether/ethyl acetate 4:1)

Mass spectrum (ESI$^+$): m/z=482 [M+H]$^+$ (6) tert-butyl 3-(4-tert-butoxycarbonyl-3-oxo-piperazine-1-carbonyl)-6-nitro-indole-1-carboxylate

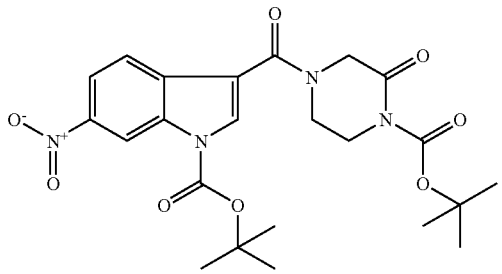

The reaction is carried out in the presence of a catalytic amount of 4-N,N-dimethylamino-pyridine at 60° C.
Mass spectrum (ESI$^+$): m/z=489 [M+H]$^+$ (7) tert-butyl 3-dimethylcarbamoyl-6-nitro-indole-1-carboxylate

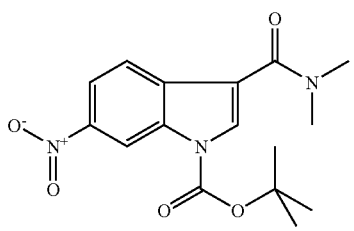

The reaction is carried out in the presence of a catalytic amount of 4-N,N-dimethylamino-pyridine.
Mass spectrum (ESI$^+$): m/z=334 [M+H]$^+$

EXAMPLE XXVIII

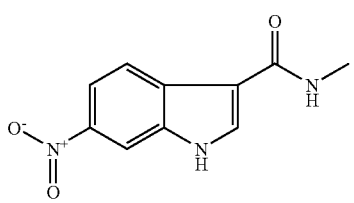

6-nitro-1H-indole-3-carboxylic acid-methylamide 250 mg 6-nitro-1H-indole-3-carboxylic acid are dissolved in 10 ml of tetrahydrofuran, combined with 240 mg carbonyldiimidazole and stirred for 30 minutes at 60° C. Then 750 µl of a 2 M solution of methylamine in tetrahydrofuran is added and the mixture is stirred overnight at 60° C. Then 1 N hydrochloric acid is added and the precipitated solid is suction filtered. Then the solid is extracted from ethyl acetate, suction filtered and dried.
Yield: 225 mg (82% of theory)
Mass spectrum (ESI$^+$): m/z=220 [M+H]$^+$ The following compounds are obtained analogously to Example XXVIII:

(1) morpholin-4-yl-(6-nitro-1H-indol-3-yl)-methanone

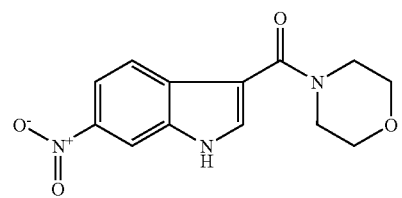

Mass spectrum (ESI$^+$): m/z=276 [M+H]$^+$ (2) tert-butyl 4-(6-nitro-1H-indole-3-carbonyl)-piperazine-1-carboxylate

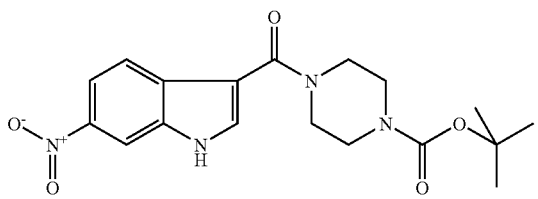

Mass spectrum (ESI$^-$): m/z=373 [M−H]$^-$ (3) 6-nitro-1H-indole-3-carboxylic acid-benzylamide

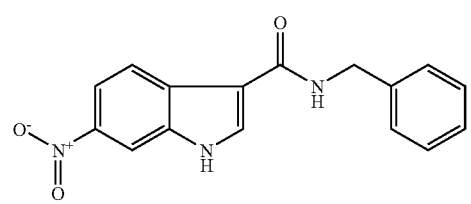

Mass spectrum (ESI$^+$): m/z=296 [M+H]$^+$ (4) 6-(3,5-dichloro-phenylsulphonylamino)-1-methyl-1H-indole-3-carboxylic acid-amide

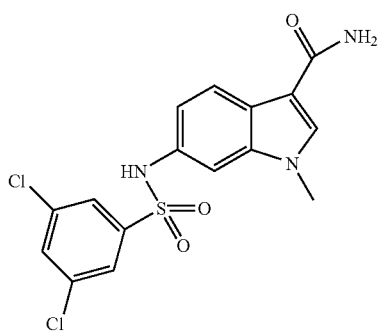

The crude product is chromatographed on silica gel (cyclohexane/ethyl acetate 40:60 to 0:100).

Mass spectrum (ESI+): m/z=398 [M+H]+

(5) 5-nitro-benzo[b]thiophene-3-carboxylic acid-methylamide

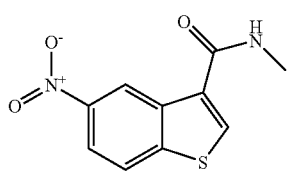

Mass spectrum (ESI+): m/z=237 [M+H]+

(6) 6-nitro-benzo[b]thiophene-3-carboxylic acid-methylamide

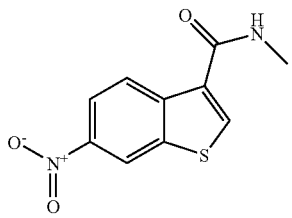

Mass spectrum (ESI+): m/z=237 [M+H]+

(7) tert.butyl (1-methylcarbamoyl-ethyl)-carbamate

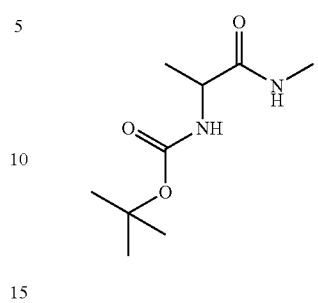

After the reaction has ended the mixture is diluted with ethyl acetate, washed with 1 M phosphoric acid solution and dried on magnesium sulphate. The solvents are then eliminated in vacuo.

Mass spectrum (ESI+): m/z=203 [M+H]+

(8) tert-butyl 2-methylcarbamoyl-pyrrolidine-1-carboxylate

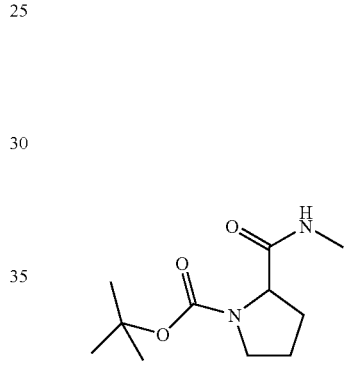

After the reaction has ended the mixture is divided between ethyl acetate and 1 M phosphoric acid solution. The organic phase is washed with 1 M sodium hydroxide solution and dried on magnesium sulphate. The solvents are eliminated in vacuo.

Mass spectrum (ESI+): m/z=229 [M+H]+

(9) 6-nitro-benzo[b]thiophene-3-carboxylic acid-amide

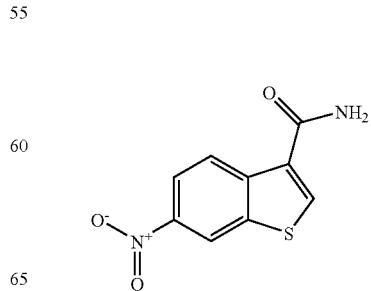

5-nitro-benzo[b]thiophene-3-carboxylic acid-amide

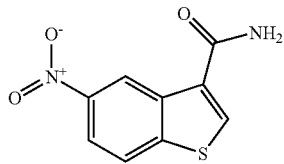

are obtained as a mixture during the reaction of a mixture of 6-nitro-benzo[b]-thiophene-3-carboxylic acid and 5-nitro-benzo[b]thiophene-3-carboxylic acid (Example XLV). The crude product is chromatographed on silica gel, while the two products are obtained as a mixture and further reacted directly in Example XII (30).

EXAMPLE XXIX

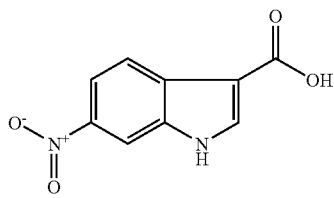

6-nitro-1H-indole-3-carboxylic acid 3.7 g 2,2,2-trifluoro-1-(6-nitro-1H-indol-3-yl)-ethanone are combined with 20 ml of a 40% sodium hydroxide solution solution and refluxed for 4 hours. After cooling to 0° C. the mixture is diluted with a little water and adjusted to pH 1 by the careful addition of concentrated hydrochloric acid. The precipitated solid is suction filtered and dissolved in dichloromethane/methanol 10:1. After drying with magnesium sulphate the solvents are eliminated in vacuo and the residue is extracted from diethyl ether.

Yield: 3 g (100% of theory)

Mass spectrum (ESI$^-$): m/z=205 [M–H]$^-$

The following compounds are obtained analogously to Example XXIX:

(1) 1-methyl-6-nitro-1H-indole-3-carboxylic acid

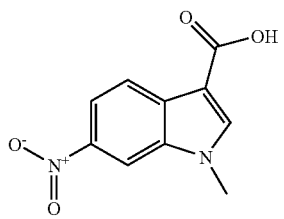

Mass spectrum (ESI$^-$): m/z=219 [M–H]$^-$ (2) 5-nitro-1H-indole-3-carboxylic acid

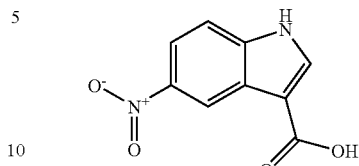

R$_f$ value: 0.30 (silica gel: dichloromethane/methanol 10:1)

EXAMPLE XXX

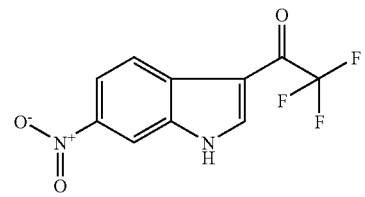

2,2,2-trifluoro-1-(6-nitro-1H-indol-3-yl)-ethanone 2.5 g 6-nitro-1H-indole are dissolved in 10 ml dimethylformamide. 5 ml trifluoroacetic anhydride are added thereto and the mixture is heated to 60° C. for 3 hours. Then the mixture is diluted with ethyl acetate and the organic phase is washed with saturated sodium hydrogen carbonate solution and with saturated sodium chloride solution. After drying with magnesium sulphate the solvents are eliminated in vacuo and the residue is extracted from dichloromethane.

Yield: 3.7 g (96% of theory)

Mass spectrum (ESI$^-$): m/z=257 [M–H]$^-$

The following compounds are obtained analogously to Example XXX:

(1) 2,2,2-trifluoro-1-(1-methyl-6-nitro-1H-indol-3-yl)-ethanone

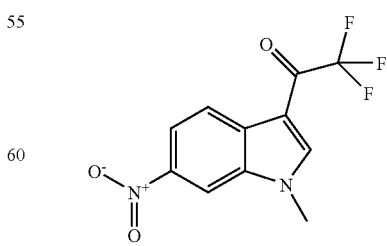

Tetrahydrofuran is used as solvent.

Mass spectrum (ESI$^-$): m/z=317 [M–HCOO]$^-$ (2) 2,2,2-trifluoro-1-(5-nitro-1H-indol-3-yl)-ethanone

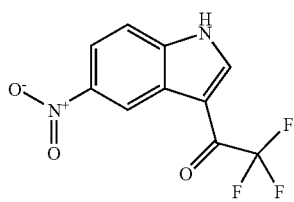

The reaction is carried out overnight at ambient temperature. The product is extracted from ethyl acetate.

$R_f$ value: 0.50 (silica gel: petroleum ether/ethyl acetate 1:1)

EXAMPLE XXXI

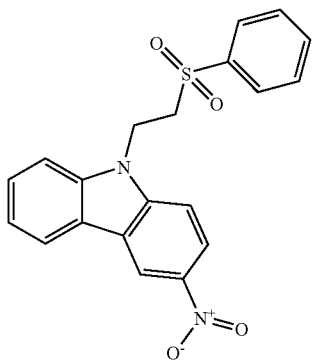

9-(2-phenylsulphonyl-ethyl)-3-nitro-9H-carbazole 3.39 g 9-(2-phenylsulphonyl-ethyl)-9H-carbazole are dissolved in 120 ml acetonitrile, and combined with 6.4 g ammonium-cerium-nitrate and 5 g silica gel. Then the mixture is heated to 70° C. for 4 hours, filtered hot and the solid is washed with hot acetonitrile. The mother liquor is freed from the solvent in vacuo and the residue is chromatographed on silica gel (dichloromethane/methanol 100:0 to 98:2).

Yield: 1.53 g (40% of theory)

Mass spectrum (ESI$^+$): m/z=381 [M+H]$^+$

EXAMPLE XXXII

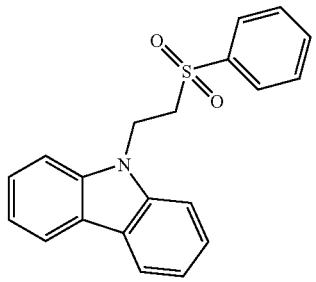

9-(2-phenylsulphonyl-ethyl)-9H-carbazole 1.8 g 9H-carbazole and 9.8 g phenylvinylsulphone are suspended in 3 ml of tetrahydrofuran, cooled to 0° C., combined with 60 µl benzyltrimethylammonium hydroxide (40% solution in water) and stirred for 20 minutes. Then the mixture is heated to 115° C. for 7 hours. Then it is divided between ethyl acetate and 1 N hydrochloric acid, the organic phase is dried on magnesium sulphate and the solvent is eliminated in vacuo. The residue is chromatographed on silica gel (cyclohexane/ethyl acetate 2:1).

Yield: 2.35 g (65% of theory)

Mass spectrum (ESI$^+$): m/z=336 [M+H]$^{30}$

EXAMPLE XXXIII

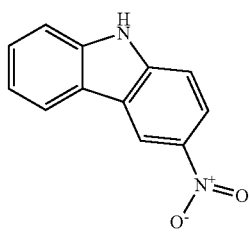

3-nitro-9H-carbazole 2.2 g 9-(2-phenylsulphonyl-ethyl)-3-nitro-9H-carbazole are dissolved in 40 ml of tetrahydrofuran, combined with 700 mg potassium-tert.-butoxide and stirred for 2 hours at ambient temperature. A further 100 mg potassium-tert.-butoxide are added and the mixture is stirred for 4 hours at ambient temperature. Then another 100 mg potassium-tert.-butoxide are added. The mixture is heated for 2 hours to 50° C., divided between ethyl acetate and 1 N hydrochloric acid, the organic phase is washed with saturated sodium chloride solution and dried with magnesium sulphate. After elimination of the solvents in vacuo the residue is chromatographed on silica gel (cyclohexane/ethyl acetate 90:10 to 80:20).

Yield: 900 mg (73% of theory)

Mass spectrum (ESI$^+$): m/z=213 [M+H]$^{30}$

EXAMPLE XXXIV

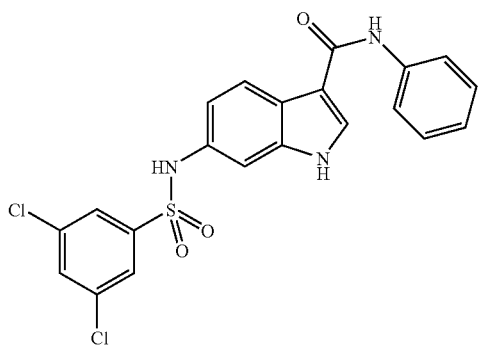

6-(3,5-dichloro-phenylsulphonylamino)-1H-indole-3-carboxylic acid-phenylamide 100 mg methyl 6-(3,5-dichloro-phenylsulphonylamino)-1H-indole-3-carboxylate are dissolved in 5 ml of methanol, combined with 2 ml 1 N sodium hydroxide solution and stirred for 2 hours at ambient temperature. Then the mixture is divided between ethyl acetate and 2 N hydrochloric acid, the aqueous phase is extracted twice with ethyl acetate and the combined organic phases are dried on sodium sulphate. The solvents are eliminated in vacuo and the residue is taken up in 3 ml dimethylformamide. 114 mg O-(7-azabenzotriazol-1-yl)-N,N,N',N'-tetramethyluronium-hexafluorophosphate (HATU) and 65 µl N,N-diisopropyl-N-ethyl-amine are added and the mixture is stirred for 3 hours at 50° C. Then it is divided between water and ethyl acetate, the aqueous phase is extracted twice with ethyl acetate and the combined organic phases are dried on sodium sulphate. After elimination of the solvents in vacuo the residue is chromatographed on silica gel (cyclohexane/ethyl acetate 90:10 to 20:80). The product thus obtained is further reacted directly in VI (28).

EXAMPLE XXXV

methyl 6-nitro-1H-indole-3-carboxylate 1 g methyl 1H-indole-3-carboxylate is dissolved in 5 ml acetic acid, combined with 500 µl concentrated nitric acid (>90%) and heated to 60° C. for 1 hour. The mixture is divided between water and dichloromethane and the aqueous phase is extracted twice with dichloromethane. The combined organic phases are dried on sodium sulphate, freed from the solvent in vacuo and the residue is chromatographed on silica gel (cyclohexane/ethyl acetate 90:10 to 40:60).

Yield: 290 mg (23% of theory)

Mass spectrum (ESI⁻): m/z=219 [M−H]⁻

In addition 275 mg of methyl 4-nitro-1H-indole-3-carboxylate are obtained.

EXAMPLE XXXVI

5-nitro-1-(phenylethyl)-1H-benzimidazole and

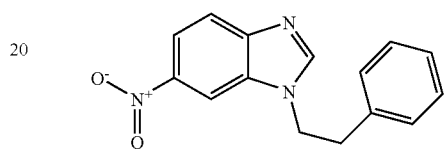

6-nitro-1-(phenylethyl)-1H-benzimidazole 1 g 5-nitro-1H-benzimidazole is dissolved in 10 ml dimethylformamide and combined with 270 mg NaH (60% in mineral oil). The mixture is left for 1 hour with stirring and 1 ml phenylethylbromide is added. Then the mixture is stirred for 3 hours at ambient temperature and divided between saturated ammonium chloride solution and ethyl acetate. The aqueous phase is extracted with ethyl acetate and the combined organic phases are dried on magnesium sulphate. After elimination of the solvents in vacuo the residue is chromatographed on silica gel (cyclohexane/ethyl acetate 90:10 to 60:40).

Yield: 820 mg (50% of theory) as an isomer mixture of 5-nitro-1-(phenylethyl)-1H-benzimidazole and 6-nitro-1-(phenylethyl)-1H-benzimidazole Mass spectrum (ESI⁺): m/z=268 [M+H]⁺

EXAMPLE XXXVII

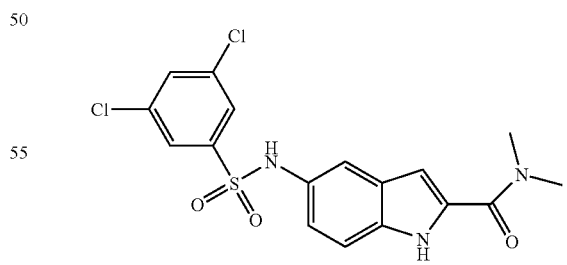

5-(3,5-dichloro-phenylsulphonylamino)-1H-indol-2-carboxylic acid-dimethylamide 55 mg 5-(3,5-dichloro-phenylsulphonylamino)-1H-indole-2-carboxylic acid are dissolved in 2 ml of tetrahydrofuran, combined with 25 mg carbonyldiimidazole, stirred for 3 hours at ambient temperature and for 1 hour at 40° C. Then the mixture is combined with 300 µl dimethylamine (2 M in tetrahydrofuran) and stirred overnight. The solvent is eliminated in vacuo and the residue is divided between ethyl acetate and 0.5 N hydrochloric acid. The organic phase is washed with water and saturated sodium chloride solution and dried on magnesium sulphate. After elimination of the solvents in vacuo the residue is chromatographed on silica gel (cyclohexane/ethyl acetate 90:10 to 30:70).

Yield: 26 mg (44% of theory)
Mass spectrum (ESI⁻): m/z=410 [M−H]⁻

The following compounds are obtained analogously to Example XXXVII:

(1) tert.butyl [(3-carbamoyl-1-methylcarbamoyl-2,3-dihydro-1H-indol-5-yl)-(3,5-dichloro-phenylsulphonyl)-amino]-acetate

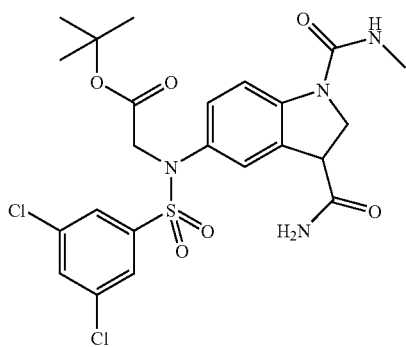

To form the imidazolide the mixture is heated to 60° C. for 1 hour. To form the methylamide the mixture is heated to 60° C. overnight. After the reaction has ended the mixture is divided between ethyl acetate and water and the organic phase is washed with saturated sodium chloride solution.

Mass spectrum (ESI⁺): m/z=557 [M+H]⁺

EXAMPLE XXXVIII

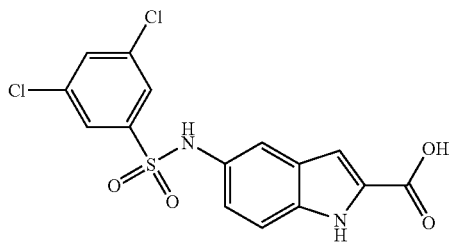

5-(3,5-dichloro-phenylsulphonylamino)-1H-indol-2-carboxylic acid 100 mg ethyl 5-(3,5-dichloro-phenylsulphonylamino)-1H-indole-2-carboxylate are dissolved in 2 ml of tetrahydrofuran and combined with 2 ml of 1 N sodium hydroxide solution. The mixture is stirred for 48 hours at ambient temperature, the tetrahydrofuran is eliminated in vacuo, the residue is diluted with water, and 1 N hydrochloric acid is added until the pH is 2. The precipitated solid is suction filtered, washed with water and dried in vacuo.

Yield: 60 mg (64% of theory)
Mass spectrum (ESI⁻): m/z=383 [M−H]⁻

EXAMPLE XXXIX

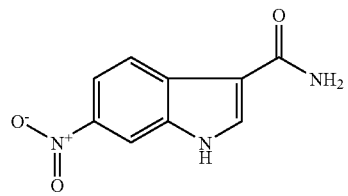

6-nitro-1H-indole-3-carboxylic acid-amide 250 mg 6-nitro-1H-indole-3-carboxylic acid are dissolved in 10 ml of toluene, combined with 3 ml of thionyl chloride and refluxed for 1 hour. Then the volatile constituents are eliminated in vacuo, the residue is taken up in dichloromethane and this is in turn eliminated in vacuo. Then it is taken up in 10 ml of tetrahydrofuran, combined with 6 ml of a 0.5 M solution of ammonia in dioxane and heated to 60° C. for 12 hours. The solvents are eliminated in vacuo, the residue is extracted from 1 N hydrochloric acid and the solid obtained is suction filtered and dried in vacuo.

Yield: 230 mg (92% of theory)
Mass spectrum (ESI⁺): m/z=206 [M+H]⁺

The following compounds are obtained analogously to Example XXXIX:

(1) 6-nitro-1H-indole-3-carboxylic acid-phenylamide

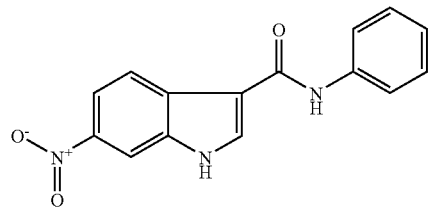

Mass spectrum (ESI⁺): m/z=282 [M+H]⁺

(2) 4-(6-nitro-1H-indole-3-carbonyl)-piperazin-2-one

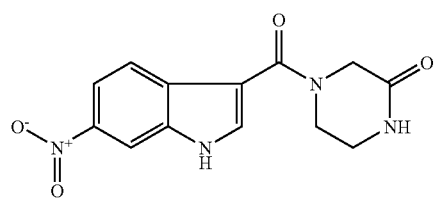

The acid chloride formed is reacted in dichloromethane with 2-oxo-piperazine in the presence of 1 equivalent of pyridine.

Mass spectrum (ESI⁻): m/z=287 [M−H]⁻

(3) 6-nitro-1H-indole-3-carboxylic acid-(1-methyl-carbamoyl-ethyl)-amide

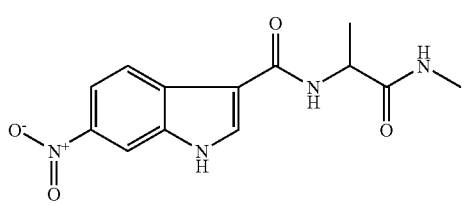

The acid chloride formed is reacted in dichloromethane with 2-oxo-piperazine in the presence of 1 equivalent of pyridine.

Mass spectrum (ESI$^+$): m/z=291 [M+H]$^+$ (4) 6-nitro-1H-indole-3-carboxylic acid-dimethylamide

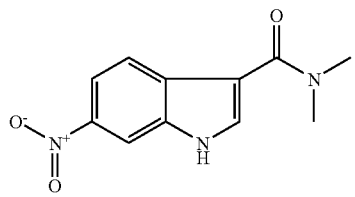

The acid chloride formed is reacted in dichloromethane with dimethylamine (2M in tetrahydrofuran) in the presence of 1 equivalent of pyridine.

Mass spectrum (ESI$^+$): m/z=234 [M+H]$^+$ (5) methyl 5-nitro-1H-indole-3-carboxylate

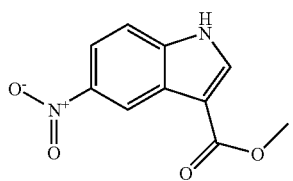

During the formation of the acid chloride, 2 drops of dimethylformamide are added and the mixture is refluxed for 5 hours. To form the methylester the mixture is refluxed in methanol for 5 hours. After cooling to ambient temperature the precipitated solid is suction filtered and dried in vacuo.

$R_f$ value: 0.40 (silica gel: dichloromethane/methanol 40:1)

EXAMPLE XL

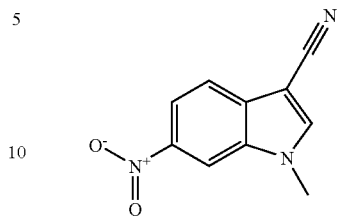

1-methyl-6-nitro-1H-indole-3-carbonitrile 1.6 g 6-nitro-1H-indole-3-carbonitrile are dissolved in 45 ml of tetrahydrofuran, combined with 1 g potassium-tert.-butoxide and stirred for 30 minutes. Then a solution of 560 μl methyl iodide in 5 ml of tetrahydrofuran is slowly added dropwise and the mixture is stirred for 5 hours. The solvents are eliminated in vacuo, water is added and the pH is adjusted to 4 by the addition of citric acid. The solid is suction filtered and washed with water and some cold methanol.

Yield: 1.59 g (65% of theory)

Mass spectrum (ESI$^+$): m/z=219 [M+NH$_4$]$^+$

EXAMPLE XLI

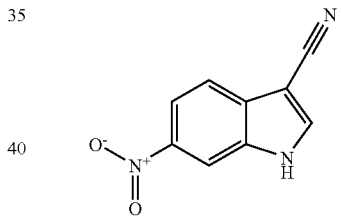

6-nitro-1H-indole-3-carbonitrile 6.1 g 6-nitro-1H-indole are dissolved in 100 ml acetonitrile and cooled to 0° C. A solution of 3.2 ml chlorosulphonyl isocyanate in 25 ml acetonitrile is added dropwise and the mixture is stirred for 2 hours. Then a solution of 5 ml triethylamine in 25 ml acetonitrile is added dropwise. The mixture is stirred for 1 hour at ambient temperature and for 50 minutes at 80° C. Then the solvents are eliminated in vacuo, the residue is extracted from cold water, the solid is suction filtered and washed successively with water, saturated sodium hydrogen carbonate solution and water. The solid thus obtained is dried in the desiccator. Then the solid is taken up in 500 ml dichloromethane/methanol 95:5 and stirred with some aluminium oxide. It is suction filtered through a thin layer of aluminium oxide and washed with 400 ml dichloromethane/methanol 95:5. The filtrate is evaporated down in vacuo and the residue is dried in vacuo.

Yield: 2.76 g (40% of theory)

Mass spectrum (ESI$^-$): m/z=186 [M−H]$^-$

EXAMPLE XLII

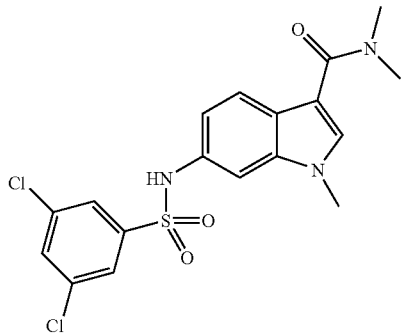

6-(3,5-dichloro-phenylsulphonylamino)-1-methyl-1H-indole-3-carboxylic acid-dimethylamide 300 mg 6-(3,5-dichloro-phenylsulphonylamino)-1-methyl-1H-indole-3-carboxylic acid are dissolved in 2 ml dimethylformamide, combined with 319 μl N,N-diisopropyl-N-ethyl-amine and 241 mg O-(benzotriazol-1-yl)-N,N,N',N'-tetramethyluronium-tetrafluoroborate (TBTU) and stirred for 15 minutes at ambient temperature. 751 μl of a 2 M solution of dimethylamine in tetrahydrofuran are added and the mixture is stirred overnight at ambient temperature. Then it is divided between water and ethyl acetate, the aqueous phase is extracted with ethyl acetate and the combined organic phases are dried on magnesium sulphate. The solvents are eliminated in vacuo.

Yield: 360 mg (112% of theory)

Mass spectrum (ESI$^-$): m/z=424 [M–H]$^-$

The following compounds are obtained analogously to Example XLII:

(1) 3,5-dichloro-N-[1-methyl-3-(morpholine-4-carbonyl)-1H-indol-6-yl]-phenylsulphonamide

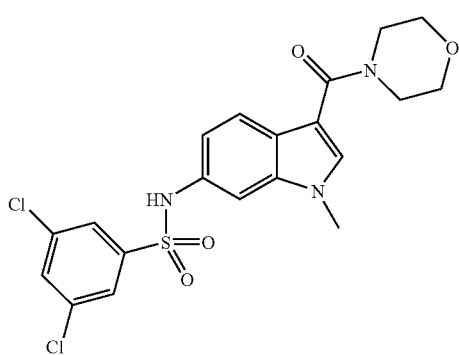

Mass spectrum (ESI$^-$): m/z=466 [M–H]$^-$ (2) 6-(3,5-dichloro-phenylsulphonylamino)-1-methyl-1H-indole-3-carboxylic acid-methylamide

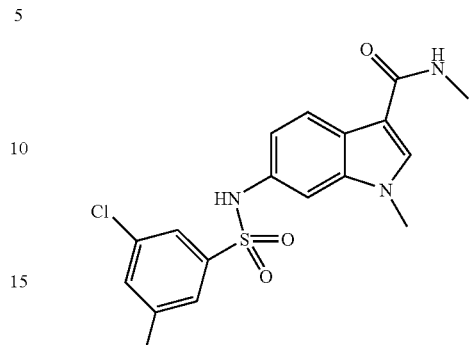

Mass spectrum (ESI$^-$): m/z=410 [M–H]$^-$ (3) 3,5-dichloro-N-[1-methyl-3-(pyrrolidine-1-carbonyl)-1H-indol-6-yl]-phenylsulphonamide

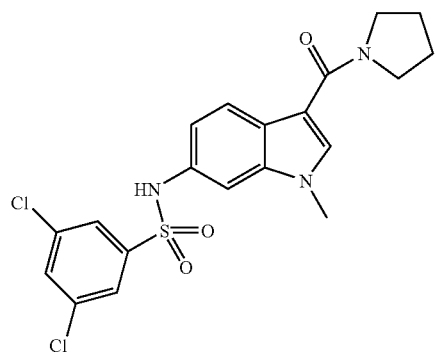

Mass spectrum (ESI$^-$): m/z=450 [M–H]$^-$ (4) 3,5-dichloro-N-[1-methyl-3-(piperidine-1-carbonyl)-1H-indol-6-yl]-phenylsulphonamide

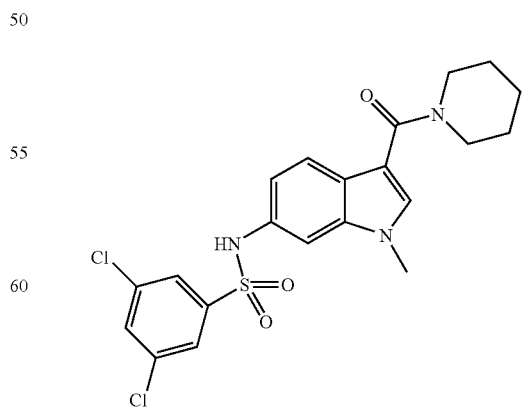

Mass spectrum (ESI$^-$): m/z=464 [M–H]$^-$ (5) 6-(3,5-dichloro-phenylsulphonylamino)-1-methyl-1H-indole-3-carboxylic acid-phenylamide

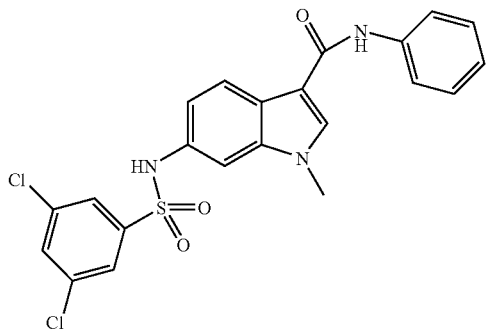

Mass spectrum (ESI⁻): m/z=472 [M−H]⁻

(6) 6-(3,5-dichloro-phenylsulphonylamino)-1-methyl-1H-indole-3-carboxylic acid-benzylamide

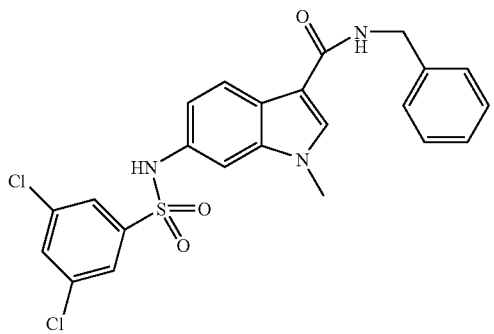

Mass spectrum (ESI⁻): m/z=486 [M−H]⁻

(7) N-[3-(azetidine-1-carbonyl)-1-methyl-1H-indol-6-yl]-3,5-dichloro-phenylsulphonamide

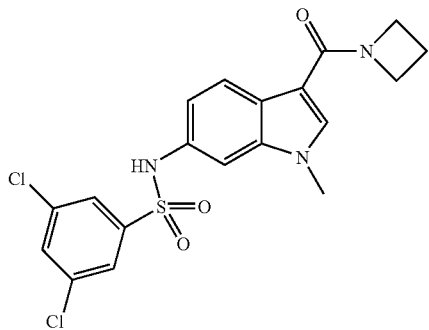

Mass spectrum (ESI⁺): m/z=438 [M+H]⁺

(8) 3,5-dichloro-N-[3-(3-hydroxy-pyrrolidine-1-carbonyl)-1-methyl-1H-indol-6-yl]-phenylsulphonamide

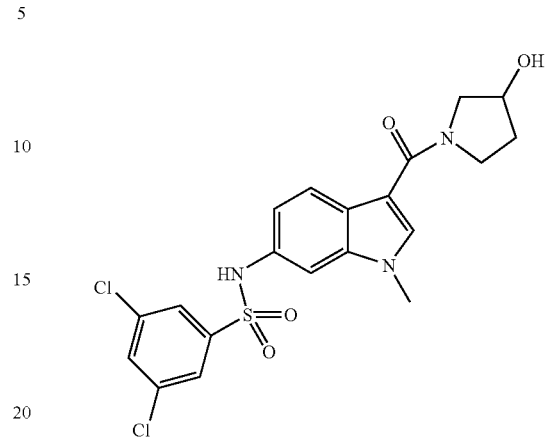

Mass spectrum (ESI⁺): m/z=468 [M+H]⁺

(9) 6-(3,5-dichloro-phenylsulphonylamino)-1-methyl-1H-indole-3-carboxylic acid-cyclopropylamide

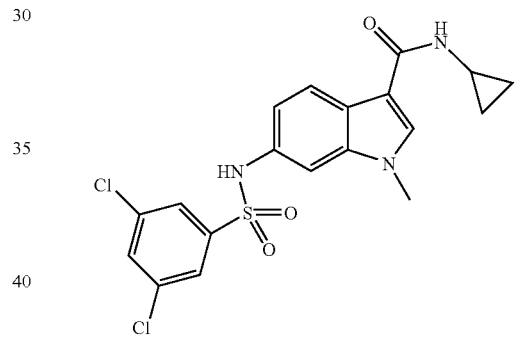

$R_f$ value: 0.34 (silica gel: petroleum ether/ethyl acetate 1:2)

(10) 6-(3,5-dichloro-phenylsulphonylamino)-1-methyl-1H-indole-3-carboxylic acid-cyclopropyl-methyl-amide

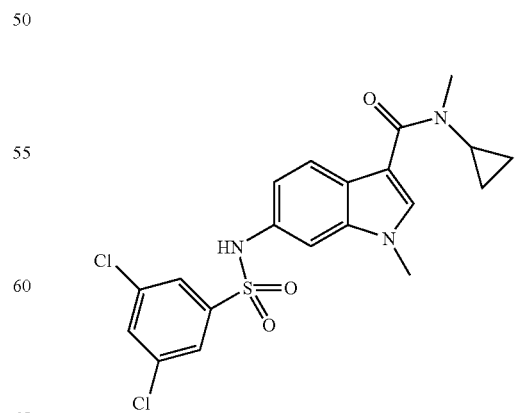

Mass spectrum (ESI⁺): m/z=452 [M+H]⁺

(11) 1-[6-(3,5-dichloro-phenylsulphonylamino)-1-methyl-1H-indole-3-carbonyl]-pyrrolidin-2-carboxylic acid-methylamide

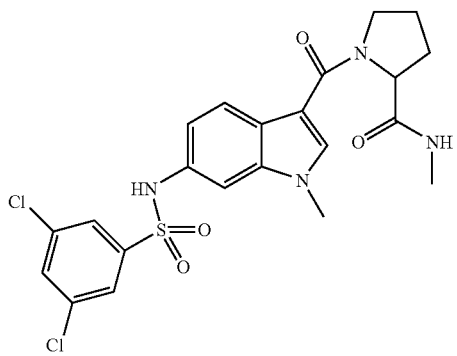

Mass spectrum (ESI⁺): m/z=509 [M+H]⁺

(12) (1-methyl-6-nitro-1H-indol-3-yl)-pyrrolidin-1-yl-methanone

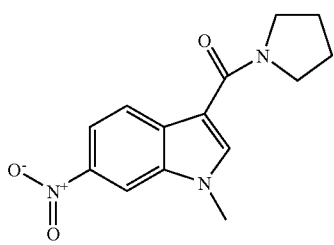

Mass spectrum (ESI⁺): m/z=274 [M+H]⁺

(13) (1-methyl-6-nitro-1H-indazol-3-yl)-pyrrolidin-1-yl-methanone

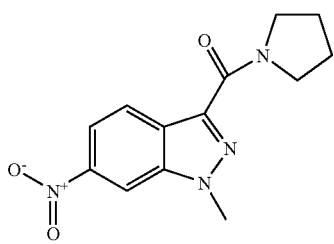

Obtained during the reaction of a mixture of 1-methyl-6-nitro-1H-indazole-3-carboxylic acid and 2-methyl-6-nitro-2H-indazole-3-carboxylic acid. The product is purified by chromatography on silica gel.

Mass spectrum (ESI⁺): m/z=275 [M+H]⁺

(14) 1-methyl-6-nitro-1H-indazole-3-carboxylic acid-methylamide

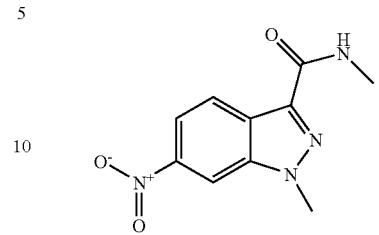

Obtained during the reaction of a mixture of 1-methyl-6-nitro-1H-indazole-3-carboxylic acid and 2-methyl-6-nitro-2H-indazole-3-carboxylic acid. The product is purified by chromatography on silica gel.

Mass spectrum (ESI⁺): m/z=235 [M+H]⁺

EXAMPLE XLIII

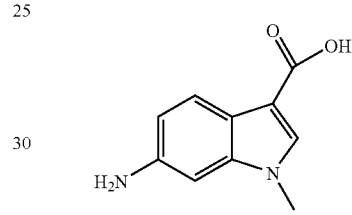

6-amino-1-methyl-1H-indole-3-carboxylic acid 12 g 6-nitro-1-methyl-1H-indole-3-carboxylic acid are dissolved in 500 ml of water, 60 ml 1 N sodium hydroxide solution and 30 ml of methanol. 1.2 g Raney nickel are added and the mixture is hydrogenated for 26 hours at 1.5 bar. Then the catalyst is filtered off and the solvent is eliminated in vacuo. The residue is suspended in 100 ml of pyridine. 16.3 g 3,5-dichlorophenylsulphonyl chloride are added and the mixture is stirred overnight at ambient temperature. The pyridine is eliminated in vacuo. The residue is divided between water and ethyl acetate and the pH is adjusted to 5 by the addition of citric acid. The aqueous phase is extracted 3 times with ethyl acetate and the combined organic phases are dried on magnesium sulphate. After elimination of the solvents the residue is chromatographed on silica gel (dichloromethane/methanol/acetic acid 95:5:1 to 89:10:1)

Yield: 2.5 g (9% of theory)

Mass spectrum (ESI⁻): m/z=397 [M–H]⁻

EXAMPLE XLIV

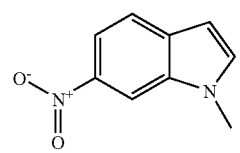

1-methyl-6-nitro-1H-indole 4 g of 6-nitro-1H-indole are added batchwise at 0° C. to 800 mg sodium hydride (60% in mineral oil) in 20 mg dimethylformamide. The mixture is stirred for 10 minutes, then 1.86 ml methyl iodide are added dropwise and the mixture is left overnight to come up to ambient temperature. Then it is divided between water and ethyl acetate, the aqueous phase is extracted with ethyl acetate and the combined organic phases are washed with saturated sodium chloride solution. After drying with magnesium sulphate the solvents are eliminated in vacuo.

Yield: 4.54 g (104% of theory)
Mass spectrum (ESI$^+$): m/z=177 [M+H]$^+$

The following compounds are obtained analogously to Example XLIV:

(1) 1,3-dimethyl-5-nitro-1,3-dihydro-benzimidazol-2-one

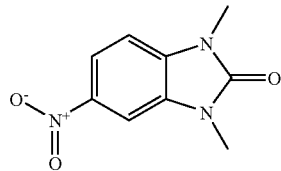

The product is extracted from ethyl acetate/methanol 95:5.
Mass spectrum (ESI$^+$): m/z=208 [M+H]$^+$

EXAMPLE XLV

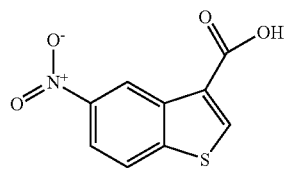

5-nitro-benzo[b]thiophene-3-carboxylic acid

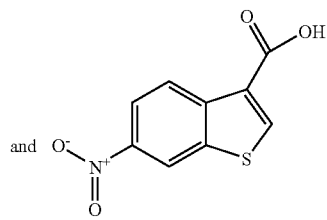

and 6-nitro-benzo[b]thiophene-3-carboxylic acid 2 g benzo[b]thiophene-3-carboxylic acid are dissolved in 11 ml acetic anhydride and cooled to 0° C. A solution of 4.4 ml concentrated nitric acid in 10 ml acetic acid is added dropwise, while not allowing the temperature to rise above 5° C. Then the mixture is stirred for 1.5 hours and then combined with 200 ml ice water. The solid is suction filtered and dried in vacuo. Then it is dissolved in hot ethanol. After cooling to ambient temperature the solid (5-nitro-benzo[b]thiophene-3-carboxylic acid, approximately 80%) is suction filtered. By elimination of the solvent in vacuo, 6-nitro-benzo[b]thiophene-3-carboxylic acid (approx. 66%) is obtained from the mother liquor.

Yield: 250 mg (10% of theory, about 80%) 5-nitro-benzo[b]thiophene-3-carboxylic acid
Mass spectrum (ESI$^-$): m/z=222 [M–H]$^-$
Yield: 624 mg (25% of theory, about 66%) 6-nitro-benzo[b]thiophene-3-carboxylic acid
Mass spectrum (ESI$^-$): m/z=222 [M–H]$^-$

EXAMPLE XLVI

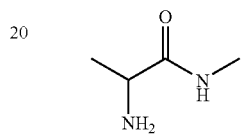

2-amino-N-methyl-propionamide 2 g tert.butyl (1-methylcarbamoyl-ethyl)-carbamate are dissolved in 20 ml dichloromethane, combined with 3.7 ml of a 4 M solution of hydrogen chloride in dioxane and stirred for 24 hours at ambient temperature. The solvents are eliminated in vacuo and the residue is divided between 10 ml 1 N sodium hydroxide solution and dichloromethane. The aqueous phase is extracted with dichloromethane and the combined organic phases are dried on magnesium sulphate. The solvents are eliminated in vacuo.

Yield: 400 mg (40% of theory)
Mass spectrum (ESI$^+$): m/z=103 [M+H]$^+$

EXAMPLE XLVII

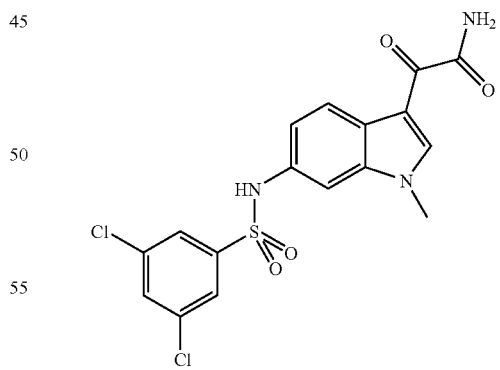

2-[6-(3,5-dichloro-phenylsulphonylamino)-1-methyl-1H-indol-3-yl]-2-oxo-acetamide 400 mg [6-(3,5-dichloro-phenylsulphonylamino)-1-methyl-1H-indol-3-yl]-oxo-acetyl-chloride are dissolved in 1.5 ml tetrahydrofuran, combined with 550 μl concentrated ammonia (32% solution in water) and stirred for 3.5 hours.

The solvent is eliminated in vacuo and the residue is extracted from a little methanol. The solid is suction filtered and dried in vacuo.

Yield: 140 mg (37% of theory)

Mass spectrum (ESI$^+$): m/z=426 [M+H]$^+$

The following compounds are obtained analogously to Example XLVII:

(1) 2-[6-(3,5-dichloro-phenylsulphonylamino)-1-methyl-1H-indol-3-yl]-N-methyl-2-oxo-acetamide

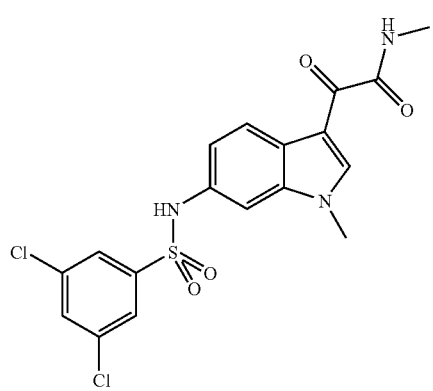

Mass spectrum (ESI$^-$): m/z=438 [M−H]$^-$ (2) 2-[6-(3,5-dichloro-phenylsulphonylamino)-1-methyl-1H-indol-3-yl]-N,N-dimethyl-2-oxo-acetamide

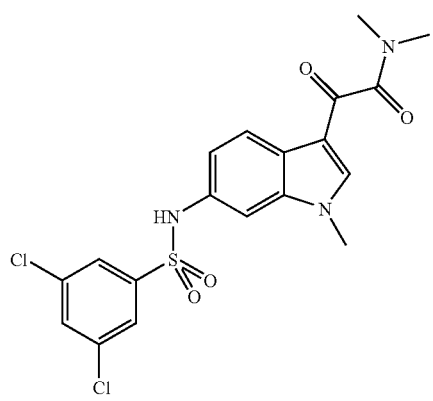

Mass spectrum (ESI$^+$): m/z=454 [M+H]$^+$ (3) 3,5-dichloro-N-[1-methyl-3-(2-oxo-2-pyrrolidin-1-yl-acetyl)-1H-indol-6-yl]-phenylsulphonamide

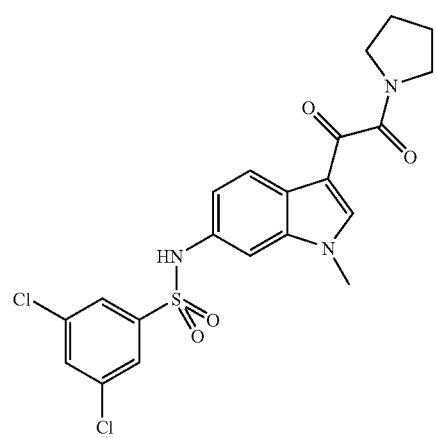

Mass spectrum (ESI$^+$): m/z=480 [M+H]$^+$

EXAMPLE XLVIII

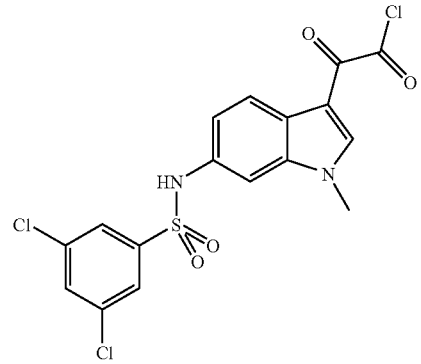

[6-(3,5-dichloro-phenylsulphonylamino)-1-methyl-1H-indol-3-yl]-oxo-acetyl-chloride 1.1 g 3,5-dichloro-N-(1-methyl-1H-indol-6-yl)phenylsulphonamide are dissolved in 15 ml diethyl ether, cooled to 0° C. and combined with 296 μl oxalyl chloride. Then the mixture is stirred for 2 hours at 0° C. and for 12 hours at ambient temp. The solvents are distilled off at 50° C. The crude product thus obtained is further reacted directly (XLVII).

Yield: 1.34 g (96% of theory)

EXAMPLE XLIX

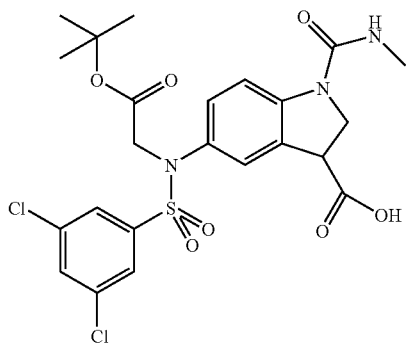

5-[tert-butoxycarbonylmethyl-(3,5-dichloro-phenyl-sulphonyl)-amino]-1-methylcarbamoyl-2,3-dihydro-1H-indole-3-carboxylic acid 100 mg methyl 5-[tert-butoxycarbonylmethyl-(3,5-dichloro-phenylsulphonyl)-amino]-1-methylcarbamoyl-2,3-dihydro-1H-indole-3-carboxylate are dissolved in 1.2 ml of tetrahydrofuran, combined with 349 μl of a 1 M solution of lithium hydroxide in water and stirred overnight at ambient temperature. Then the mixture is cooled to 0° C., combined with 350 μl 1 M hydrochloric acid and divided between ethyl acetate and saturated sodium chloride solution. The organic phase is dried on magnesium sulphate and the solvents are eliminated in vacuo. The residue is chromatographed on silica gel (dichloromethane/methanol 20:1).
Yield: 40 mg (41% of theory)
Mass spectrum (ESI$^+$): m/z=558 [M+H]$^+$

EXAMPLE L

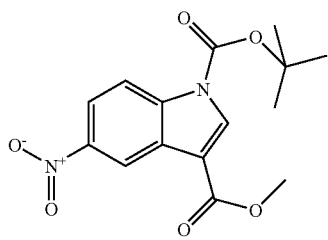

1-tert-butyl-3-methyl 5-nitro-indole-1,3-dicarboxylate 5.9 g methyl 5-nitro-1H-indole-3-carboxylate are dissolved in 100 ml acetonitrile, combined with 100 mg N,N-dimethylamino-pyridine and a solution of 6.4 g di-tert.-butyl-dicarbonate in 20 ml of tetrahydrofuran is added dropwise thereto. The mixture is stirred overnight at ambient temperature, then heated to 30° C. for 30 minutes and cooled to 0° C. The solid thus precipitated is suction filtered. The mother liquor is freed from the solvents in vacuo and the residue is extracted from petroleum ether/ethyl acetate.
Yield: 7.4 g (86% of theory)
R$_f$-value: 0.50 (silica gel: petroleum ether/ethyl acetate 3:1)

EXAMPLE LI

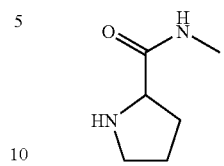

pyrrolidine-2-carboxylic acid-methylamide.CF$_3$CO$_2$H 200 mg tert-butyl 2-methylcarbamoyl-pyrrolidine-1-carboxylate are dissolved in 2 ml dichloromethane, combined with 1 ml trifluoroacetic acid and stirred for 2 hours at ambient temperature. Then the volatile constituents are eliminated in vacuo, the residue is dissolved in dichloromethane and diethyl ether and combined with some activated charcoal. Then the solution is filtered, evaporated down in vacuo and the residue is dried in vacuo.

The product thus obtained is further reacted directly in V (8).

EXAMPLE LII

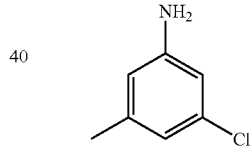

3-chloro-5-methyl-aniline 2.4 g of 3-chloro-5-nitro-toluene are dissolved in 35 ml of ethanol, combined with 15.8 g tin dichloride-dihydrate and refluxed for 3 hours. The solvent is eliminated in vacuo, the residue is taken up in 4 M sodium hydroxide solution and filtered through kieselguhr. The filter cake is washed thoroughly with ethyl acetate. The aqueous phase is extracted 3 times with ethyl acetate and the combined organic phases are washed with saturated sodium chloride solution and dried on magnesium sulphate. The solvent is eliminated in vacuo and the residue is chromatographed on silica gel (cyclohexane/ethyl acetate 81:15 to 70:30).
Yield: 1.59 g (80% of theory)
Mass spectrum (ESI$^+$): m/z=142 [M+H]$^+$

EXAMPLE LIII

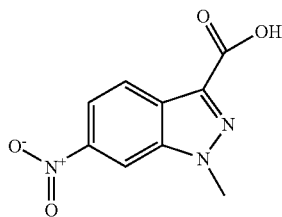

1-methyl-6-nitro-1H-indazole-3-carboxylic acid and

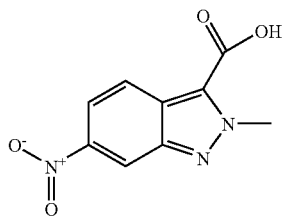

2-methyl-6-nitro-2H-indazole-3-carboxylic acid 670 mg of a mixture of methyl 1-methyl-6-nitro-1H-indazole-3-carboxylate and methyl 2-methyl-6-nitro-2H-indazole-3-carboxylate (Example LV) are dissolved in 20 ml of ethanol, combined with 10 ml of 1 M sodium hydroxide solution and stirred for 2 hours. Then 10 ml of 1 M hydrochloric acid are added, the mixture is diluted with water and the precipitated solid is suction filtered. Then the solid is dissolved in dichloromethane/methanol 90:10. After drying with magnesium sulphate the solvents are eliminated in vacuo and the residue is dried in vacuo. 640 mg of a mixture of 1-methyl-6-nitro-1H-indazole-3-carboxylic acid and 2-methyl-6-nitro-2H-indazole-3-carboxylic acid is obtained, which is further reacted directly in Example XLII (13) or in XLII (14).

EXAMPLE LIV

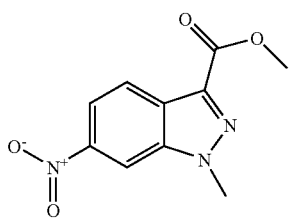

methyl 1-methyl-6-nitro-1H-indazole-3-carboxylate

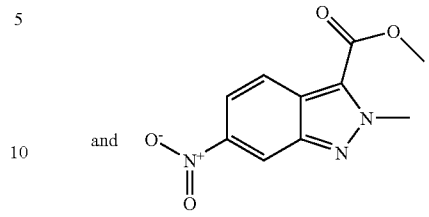

and methyl 2-methyl-6-nitro-2H-indazole-3-carboxylate 830 mg of 6-nitro-1H-indazole-3-carboxylic acid are dissolved in 16 ml dimethylformamide, combined with 1.66 g potassium carbonate and 823 µl methyl iodide and stirred for 4 hours at 50° C. After cooling to ambient temperature the mixture is divided between water and ethyl acetate. The aqueous phase is extracted twice with ethyl acetate and the combined organic phases are washed with saturated sodium chloride solution. After drying with magnesium sulphate the solvents are eliminated in vacuo. The residue is dissolved in hot dimethylformamide and after cooling to ambient temperature the precipitated solid is suction filtered and washed with diethyl ether. 670 mg of a mixture of methyl 1-methyl-6-nitro-1H-indazole-3-carboxylate and methyl 2-methyl-6-nitro-2H-indazole-3-carboxylate is obtained, which is further reacted directly in Example LIII.

EXAMPLE LV

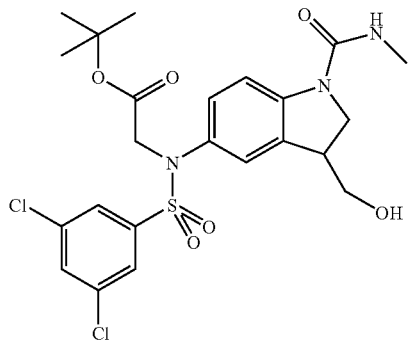

tert.butyl [(3,5-dichloro-phenylsulphonyl)-(3-hydroxymethyl-1-methylcarbamoyl-2,3-dihydro-1H-indol-5-yl)-amino]-acetate 110 mg methyl 5-[tert-butoxycarbonylmethyl-(3,5-dichloro-phenylsulphonyl)-amino]-1-methylcarbamoyl-2,3-dihydro-1H-indole-3-carboxylate are dissolved in 3 ml of tetrahydrofuran, cooled to 0° C., combined with 4.2 mg lithium borohydride and stirred for 1 hour. Then the mixture is allowed to come up to ambient temperature and stirred overnight. Then it is divided between ethyl acetate and ice water, the pH is adjusted to 4 by the addition of citric acid and the phases are separated. The organic phase is washed with water and saturated sodium chloride solution, dried on magnesium sulphate and freed from the solvents in vacuo. The residue is chromatographed on silica gel (ethyl acetate).

Yield: 43 mg (41% of theory)

Mass spectrum (ESI$^+$): m/z=544 [M+H]$^+$

Preparation of the End Compounds

EXAMPLE 1

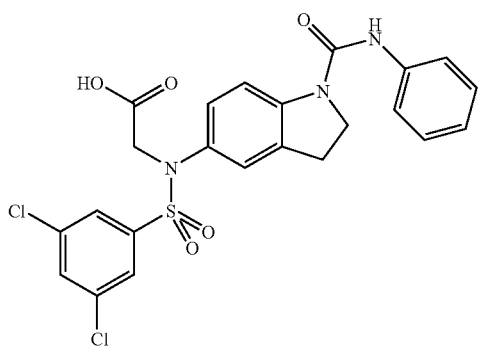

[(3,5-dichloro-phenylsulphonyl)-(1-phenylcarbamoyl-2,3-dihydro-1H-indol-5-yl)-amino]-acetic acid 1.24 g tert.butyl [(3,5-dichloro-phenylsulphonyl)-(1-phenylcarbamoyl-2,3-dihydro-1H-indol-5-yl)-amino]-acetate are dissolved in 10 ml dichloromethane. 5 ml of trifluoroacetic acid is added with stirring. The mixture is stirred for 2 hours at ambient temperature and then the solvents are eliminated in vacuo. The residue is extracted from diisopropylether and cyclohexane.

Yield: 1.09 g (97% of theory)

Mass spectrum (ESI$^+$): m/z=520 [M+H]$^{30}$

The following compounds are obtained analogously to Example 1:

(1) [(1-benzylcarbamoyl-1H-indol-5-yl)-(3,5-dichloro-phenylsulphonyl)-amino]-acetic acid

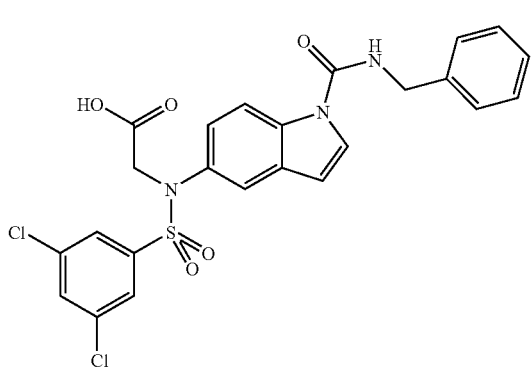

Mass spectrum (ESI$^+$): m/z=532 [M+H]$^+$ (2) [(1-benzylcarbamoyl-1H-indol-4-yl)-(3,5-dichloro-phenylsulphonyl)-amino]-acetic acid

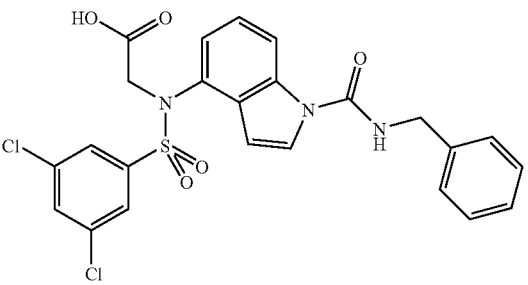

Mass spectrum (ESI$^+$): m/z=532 [M+H]$^+$ (3) [(3,5-dichloro-phenylsulphonyl)-(1-phenylcarbamoyl-1H-indol-5-yl)-amino]-acetic acid

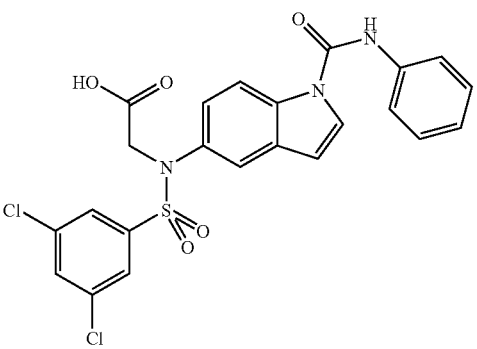

Mass spectrum (ESI$^+$): m/z=518 [M+H]$^+$ (4) [(1-benzoyl-1H-indol-5-yl)-(3,5-dichloro-phenylsulphonyl)-amino]-acetic acid

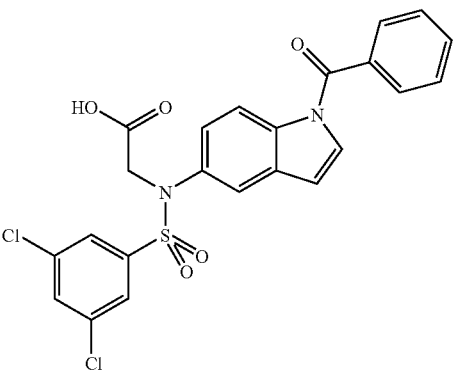

Mass spectrum (ESI$^-$): m/z=501 [M−H]$^-$ (5) [(3,5-dichloro-phenylsulphonyl)-(1-phenylacetyl-1H-indol-5-yl)-amino]-acetic acid

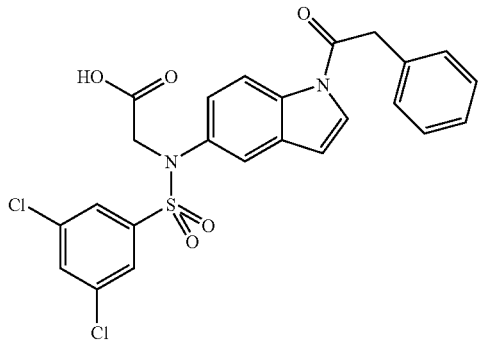

Mass spectrum (ESI⁺): m/z=517 [M+H]⁺

(6) [(3,5-dichloro-phenylsulphonyl)-(1-phenylacetyl-2,3-dihydro-1H-indol-5-yl)-amino]-acetic acid

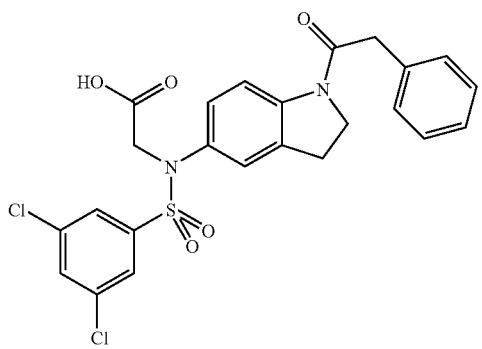

Mass spectrum (ESI⁺): m/z=519 [M+H]⁺

(7) {(3,5-dichloro-phenylsulphonyl)-[1-(phenylethyl)-1H-indol-5-yl]-amino}-acetic acid

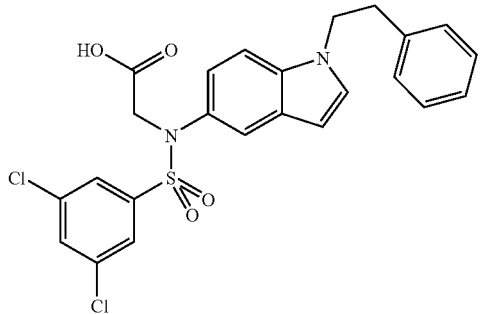

Mass spectrum (ESI⁺): m/z=503 [M+H]⁺

(8) {(3,5-dichloro-phenylsulphonyl)-[1-(phenylethyl)-3-(2,2,2-trifluoro-acetyl)-1H-indol-5-yl]-amino}-acetic acid

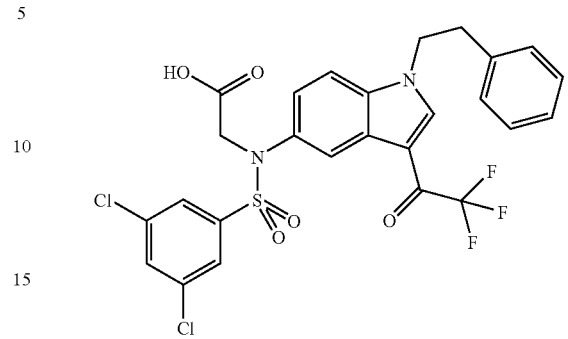

Obtained as a by-product of the cleaving of tert.butyl {(3,5-dichloro-phenylsulphonyl)-[1-(phenylethyl)-1H-indol-5-yl]-amino}-acetate to form {(3,5-dichloro-phenylsulphonyl)-[1-(phenylethyl)-1H-indol-5-yl]-amino}-acetic acid. The products are separated by preparative HPLC.

Mass spectrum (ESI⁻): m/z=597 [M−H]⁻

(9) [(1-benzoyl-2,3-dihydro-1H-indol-5-yl)-(3,5-dichloro-phenylsulphonyl)-amino]-acetic acid

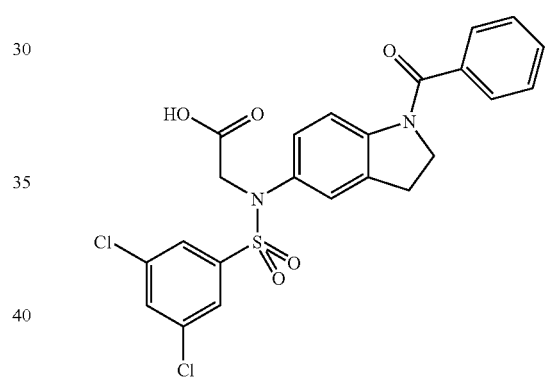

Mass spectrum (ESI⁺): m/z=505 [M+H]⁺

(10) [(1-phenylsulphonyl-2,3-dihydro-1H-indol-5-yl)-(3,5-dichloro-phenylsulphonyl)-amino]-acetic acid

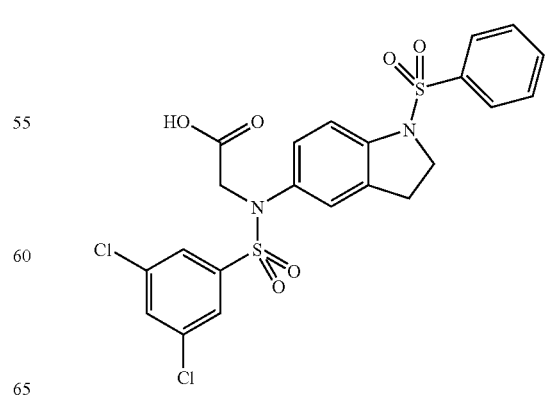

Mass spectrum (ESI⁻): m/z=539 [M−H]⁻

(11) [(1-benzylcarbamoyl-2,3-dihydro-1H-indol-5-yl)-(3,5-dichloro-phenylsulphonyl)-amino]-acetic acid

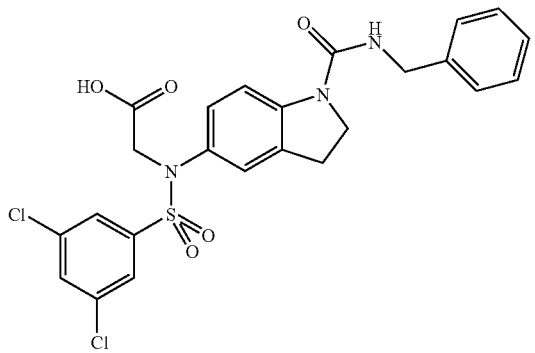

Mass spectrum (ESI⁺): m/z=534 [M+H]⁺

(12) [(3,5-dichloro-phenylsulphonyl)-(1-phenyl-methanesulphonyl-2,3-dihydro-1H-indol-5-yl)-amino]-acetic acid

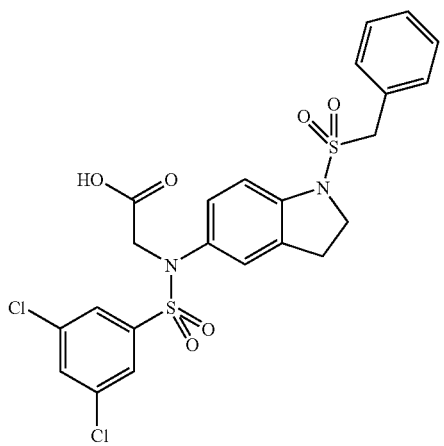

Mass spectrum (ESI⁻): m/z=553 [M−H]⁻

(13) {(3,5-dichloro-phenylsulphonyl)-[1-(3-nitro-phenylcarbamoyl)-2,3-dihydro-1H-indol-5-yl]-amino}-acetic acid

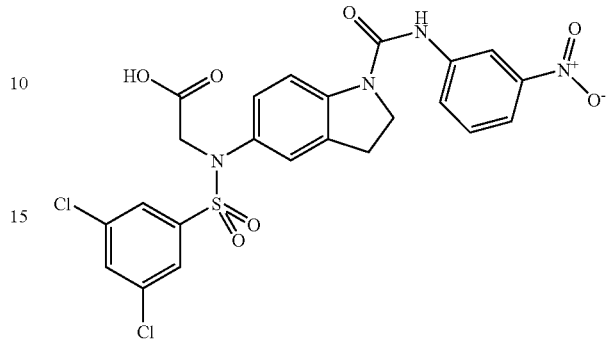

Mass spectrum (ESI⁺): m/z=565 [M+H]⁺

(14) {(3,5-dichloro-phenylsulphonyl)-[1-(2-nitro-phenylcarbamoyl)-2,3-dihydro-1H-indol-5-yl]-amino}-acetic acid

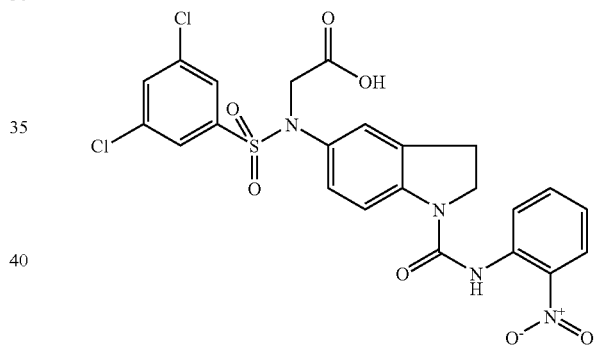

Mass spectrum (ESI⁺): m/z=565 [M+H]⁺

(15) {(3,5-dichloro-phenylsulphonyl)-[1-(pyrazin-2-ylcarbamoyl)-2,3-dihydro-1H-indol-5-yl]-amino}-acetic acid

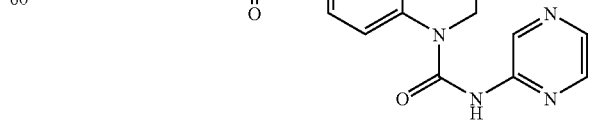

Mass spectrum (ESI⁻): m/z=520 [M−H]⁻

(16) {(3,5-dichloro-phenylsulphonyl)-[1-(1-oxy-pyridin-3-ylcarbamoyl)-2,3-dihydro-1H-indol-5-yl]-amino}-acetic acid

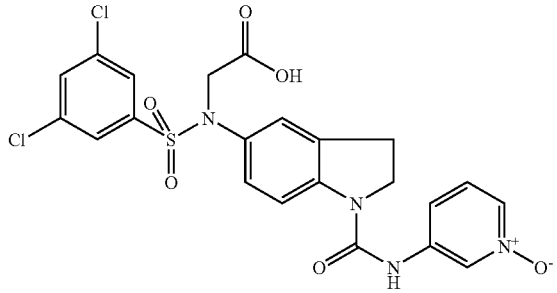

Mass spectrum (ESI+): m/z=537 [M+H]+

(17) [(3,5-dichloro-phenylsulphonyl)-(2,3-dihydro-1H-indol-5-yl)-amino]-acetic acid*CF3CO2H

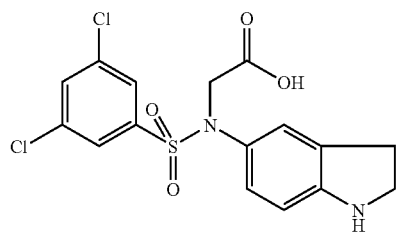

Mass spectrum (ESI+): m/z=401 [M+H]+

(18) [(3,5-dichloro-phenylsulphonyl)-(1-methylcarbamoyl-2,3-dihydro-1H-indol-5-yl)-amino]-acetic acid

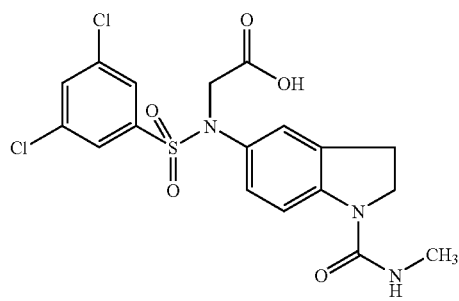

Mass spectrum (ESI+): m/z=458 [M+H]+

(19) [N-(3,5-dichloro-phenyl-sulphonyl)-N-(1-dimethylcarbamoyl-2,3-dihydro-1H-indol-5-yl)-amino]-acetic acid

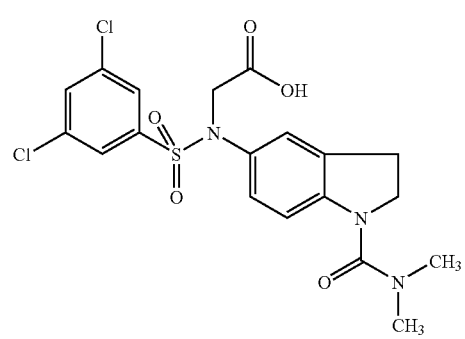

Mass spectrum (ESI+): m/z=472 [M+H]+

(20) {N-(3,5-dichloro-phenylsulphonyl)-N-[1-(2-dimethylamino-ethylcarbamoyl)-2,3-dihydro-1H-indol-5-yl]-amino}acetic acid*CF3CO2H

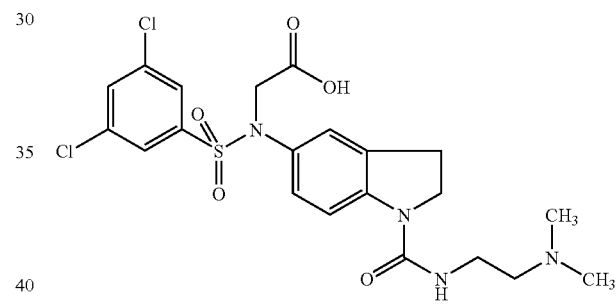

Mass spectrum (ESI+): m/z=515 [M+H]+

(21) [[1-(5-chloro-1H-indol-2-carbonyl)-2,3-dihydro-1H-indol-5-yl]-(3,5-dichloro-phenylsulphonyl)-amino]-acetic acid

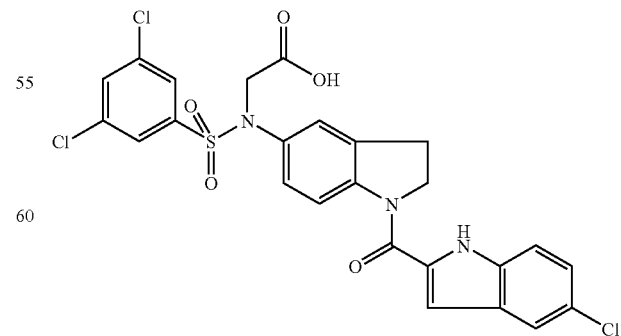

Mass spectrum (ESI+): m/z=578 [M+H]+

(22) methyl 5-[carboxymethyl-(3,5-dichloro-phenyl-sulphonyl)-amino]-benzo[b]thiophene-2-carboxylate

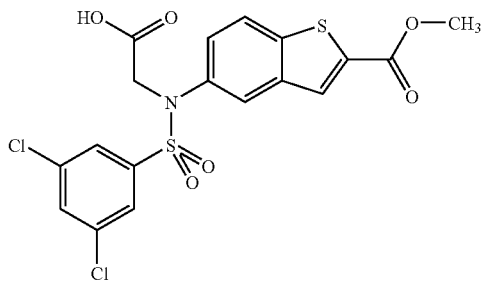

Mass spectrum (ESI⁻): m/z=472 [M−H]⁻

(23) [(2-carbamoyl-benzo[b]thiophene-5-yl)-(3,5-dichloro-phenylsulphonyl)-amino]-acetic acid

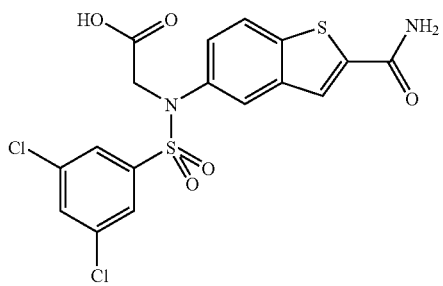

Mass spectrum (ESI⁺): m/z=459 [M+H]⁺

(24) {(3,5-dichloro-phenylsulphonyl)-[1-(phenyl-ethyl)-1H-benzimidazol-5-yl]-amino}acetic acid*CF₃CO₂H

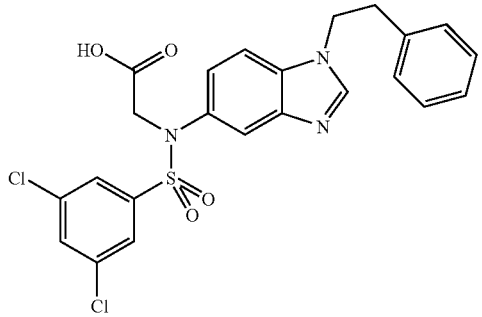

Mass spectrum (ESI⁺): m/z=504 [M+H]⁺

(25) {(3,5-dichloro-phenylsulphonyl)-[3-(phenyl-ethyl)-3H-benzimidazol-5-yl]-amino}-acetic acid*CF₃CO₂H

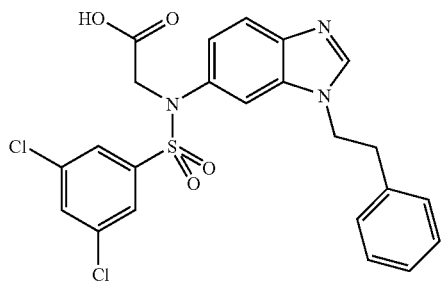

Mass spectrum (ESI⁺): m/z=504 [M+H]⁺

(26) [(9H-carbazol-3-yl)-(3,5-dichloro-phenylsul-phonyl)-amino]-acetic acid

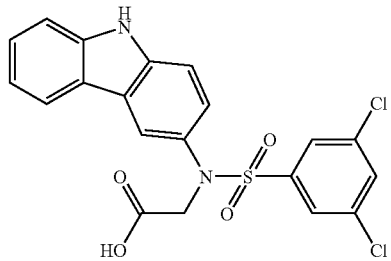

The crude product is chromatographed on silica gel.
Mass spectrum (ESI⁺): m/z=449 [M+H]⁺

(27) [(3-chloro-5-methoxy-phenylsulphonyl)-(9-ethyl-9H-carbazol-3-yl)-amino]-acetic acid

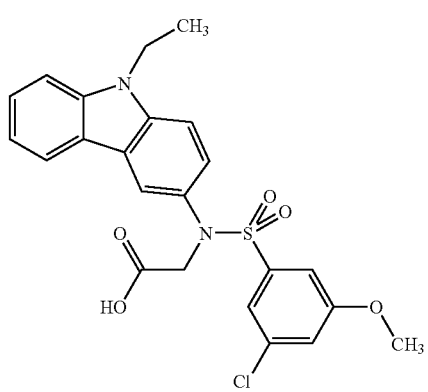

The crude product is chromatographed on silica gel.
Mass spectrum (ESI⁺): m/z=473 [M+H]⁺

(28) [(2,6-dichloro-pyridine-4-sulphonyl)-(9-ethyl-9H-carbazol-3-yl)-amino]-acetic acid

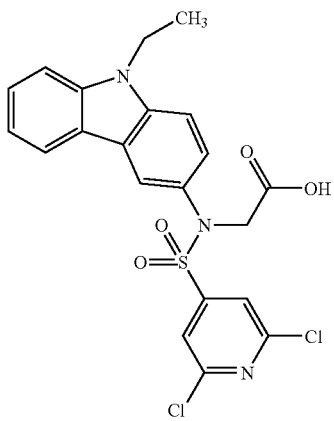

Mass spectrum (ESI+): m/z=478 [M+H]+

(29) {(3,5-dichloro-phenylsulphonyl)-[1-(3,5-dichloro-phenylsulphonyl)-3-methyl-1H-indazol-5-yl]-amino}-acetic acid

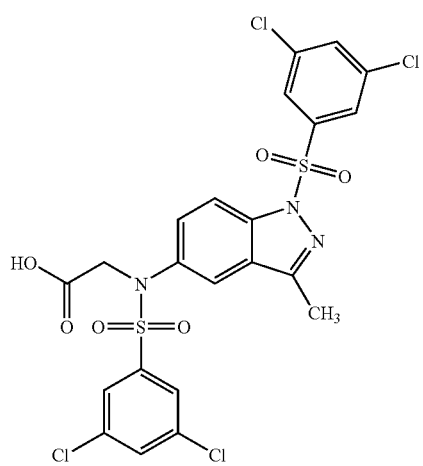

Mass spectrum (ESI−): m/z=620 [M−H]−
$R_f$ value: 0.30 (silica gel: dichloromethane/methanol 95:5)

(30) {(3,5-dichloro-phenylsulphonyl)-[3-(morpholine-4-carbonyl)-1H-indol-6-yl]-amino}-acetic acid

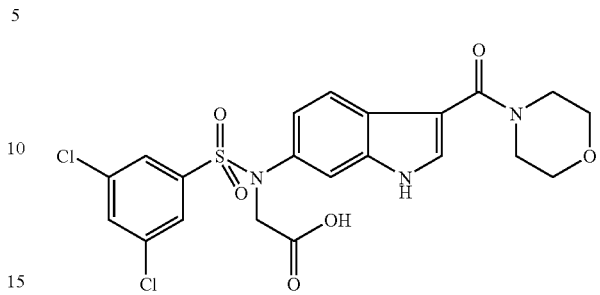

Mass spectrum (ESI+): m/z=512 [M+H]+

(31) {(3,5-dichloro-phenylsulphonyl)-[3-(piperazine-1-carbonyl)-1H-indol-6-yl]-amino}-acetic acid*CF₃CO₂H

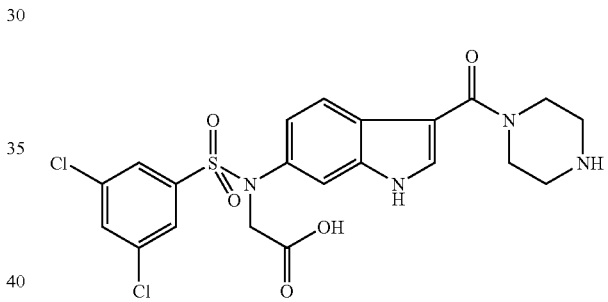

Mass spectrum (ESI+): m/z=511 [M+H]+

(32) [(3,5-dichloro-phenylsulphonyl)-(3-methylcarbamoyl-1H-indol-6-yl)-amino]-acetic acid

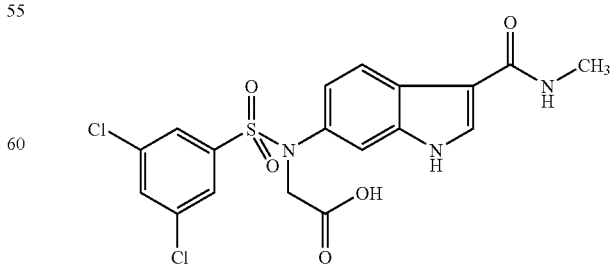

Mass spectrum (ESI−): m/z=454 [M−H]−

(33) [(3-benzylcarbamoyl-1H-indol-6-yl)-(3,5-dichloro-phenylsulphonyl)-amino]-acetic acid

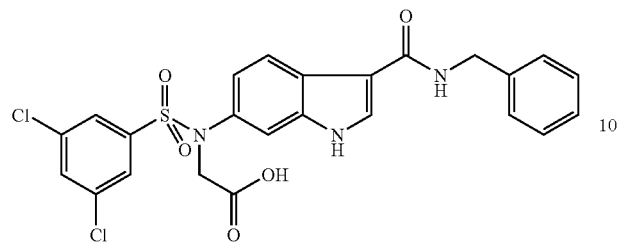

Mass spectrum (ESI+): m/z=532 [M+H]+

(34) [(3,5-dichloro-phenylsulphonyl)-(3-phenylcarbamoyl-1H-indol-6-yl)-amino]-acetic acid

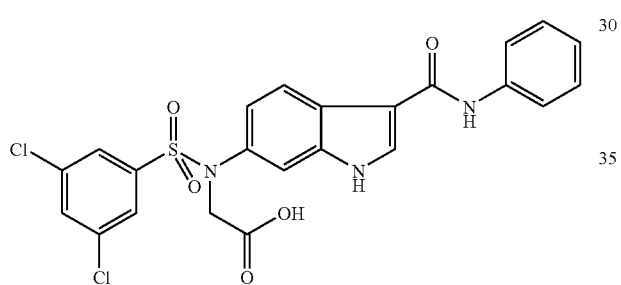

Mass spectrum (ESI+): m/z=518 [M+H]+

(35) [(3-carbamoyl-1H-indol-6-yl)-(3,5-dichloro-phenylsulphonyl)-amino]-acetic acid

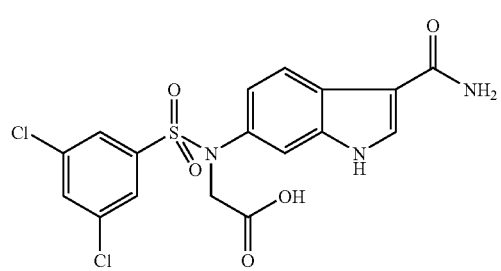

Mass spectrum (ESI+): m/z=442 [M+H]+

(36) {(3,5-dichloro-phenylsulphonyl)-[1-(3-oxo-piperazine-1-carbonyl)-2,3-dihydro-1H-indol-5-yl]-amino}-acetic acid

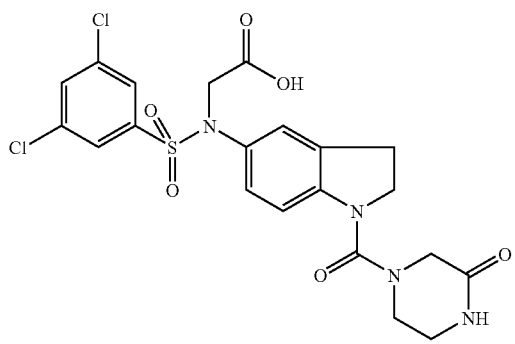

Mass spectrum (ESI+): m/z=527 [M+H]+

(37) [[9-(2-phenylsulphonyl-ethyl)-9H-carbazol-3-yl]-(3,5-dichloro-phenylsulphonyl)-amino]-acetic acid

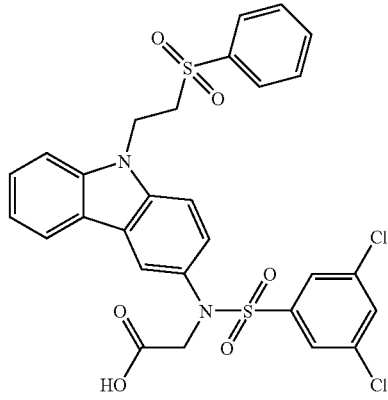

Mass spectrum (ESI−): m/z=615 [M−H]−

(38) {6-[carboxymethyl-(3,5-dichloro-phenylsulphonyl)-amino]-3-phenylcarbamoyl-indol-1-yl}-acetic acid

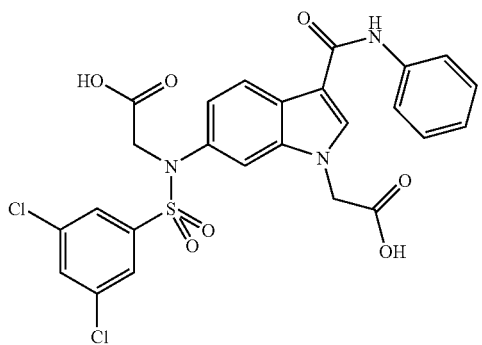

Mass spectrum (ESI⁻): m/z=574 [M−H]⁻

(39) [(3,5-dichloro-phenylsulphonyl)-(2-dimethyl-carbamoyl-1H-indol-5-yl)-amino]-acetic acid

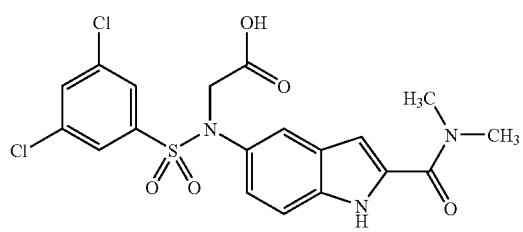

Mass spectrum (ESI⁺): m/z=470 [M+H]⁺

(40) [(3-cyano-1-methyl-1H-indol-6-yl)-(3,5-dichloro-phenylsulphonyl)-amino]-acetic acid

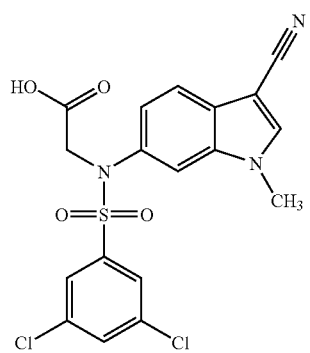

Mass spectrum (ESI⁺): m/z=438 [M+H]⁺

(41) [(3,5-dichloro-phenylsulphonyl)-(3-dimethyl-carbamoyl-1-methyl-1H-indol-6-yl)-amino]-acetic acid

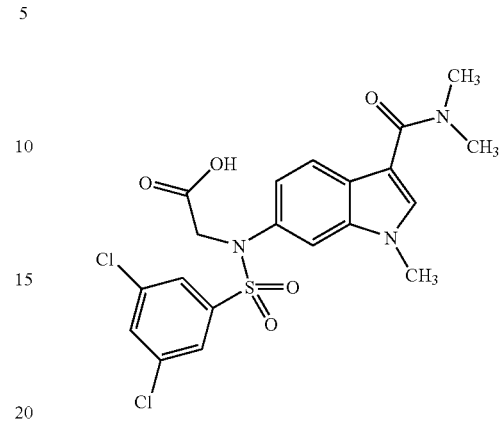

Mass spectrum (ESI⁺): m/z=484 [M+H]⁺

(42) [(3-carbamoyl-1-methyl-1H-indol-6-yl)-(3,5-dichloro-phenylsulphonyl)-amino]-acetic acid

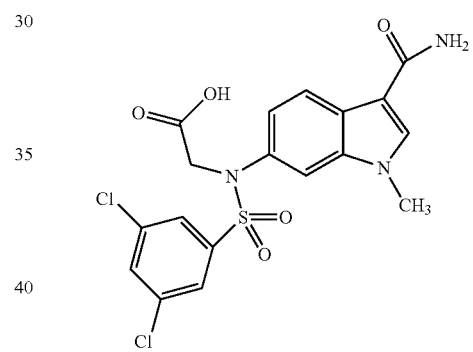

Mass spectrum (ESI⁺): m/z=456 [M+H]⁺

(43) [(3,5-dichloro-phenylsulphonyl)-(3-methylcarbamoyl-benzo[b]thiophene-5-yl)-amino]-acetic acid

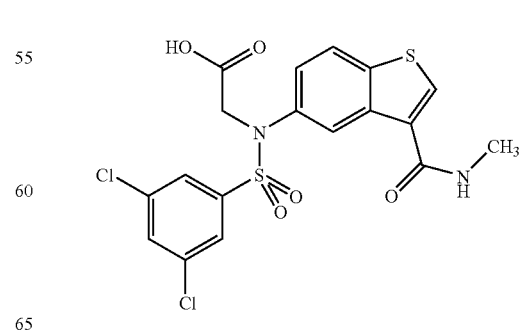

Mass spectrum (ESI⁻): m/z=471 [M−H]⁻

(44) [(3,5-dichloro-phenylsulphonyl)-(3-methylcarbamoyl-benzo[b]thiophene-6-yl)-amino]-acetic acid

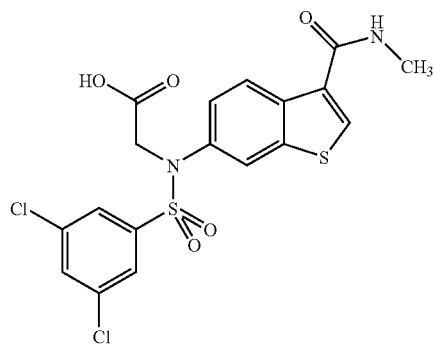

Mass spectrum (ESI−): m/z=471 [M−H]−

(45) {(3,5-dichloro-phenylsulphonyl)-[1-(1-methylcarbamoyl-ethylcarbamoyl)-2,3-dihydro-1H-indol-5-yl]-amino}-acetic acid

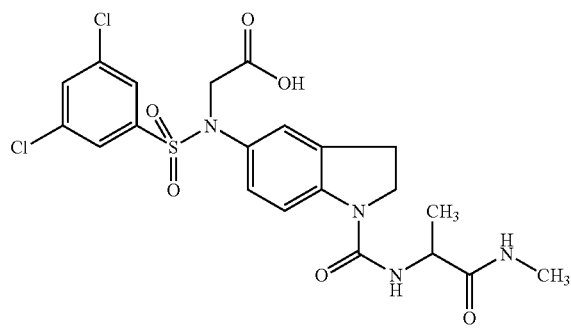

Mass spectrum (ESI−): m/z=527 [M−H]−

(46) {(3,5-dichloro-phenylsulphonyl)-[3-(3-oxo-piperazine-1-carbonyl)-1H-indol-6-yl]-amino}-acetic acid

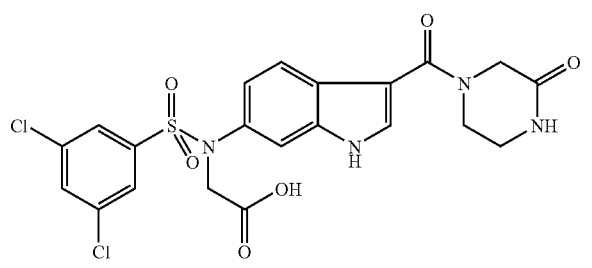

Mass spectrum (ESI+): m/z=525 [M+H]+

(47) {(3,5-dichloro-phenylsulphonyl)-[3-(1-methylcarbamoyl-ethylcarbamoyl)-1H-indol-6-yl]-amino}-acetic acid

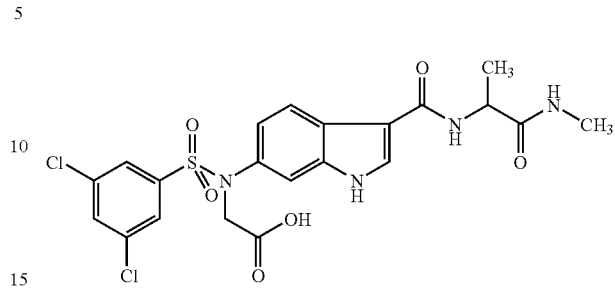

Mass spectrum (ESI+): m/z=527 [M+H]+

(48) {(3,5-dichloro-phenylsulphonyl)-[1-methyl-3-(morpholine-4-carbonyl)-1H-indol-6-yl]-amino}-acetic acid

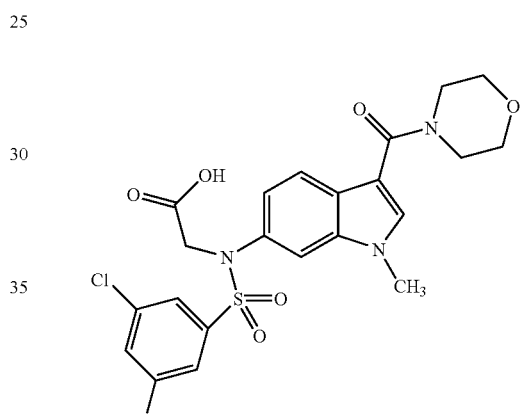

Mass spectrum (ESI+): m/z=526 [M+H]+

(49) [(3,5-dichloro-phenylsulphonyl)-(1-methyl-3-methylcarbamoyl-1H-indol-6-yl)-amino]-acetic acid

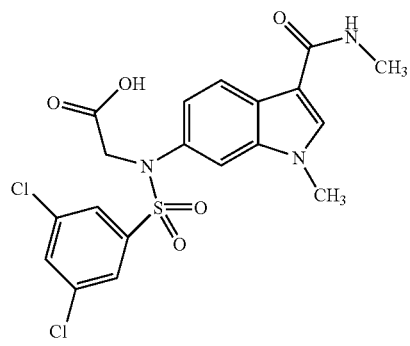

Mass spectrum (ESI+): m/z=470 [M+H]+

(50) {(3,5-dichloro-phenylsulphonyl)-[1-methyl-3-(pyrrolidine-1-carbonyl)-1H-indol-6-yl]-amino}-acetic acid

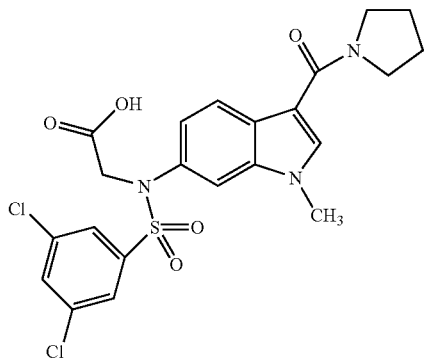

Mass spectrum (ESI⁺): m/z=510 [M+H]⁺

(51) {(3,5-dichloro-phenylsulphonyl)-[1-methyl-3-(piperidine-1-carbonyl)-1H-indol-6-yl]-amino}-acetic acid

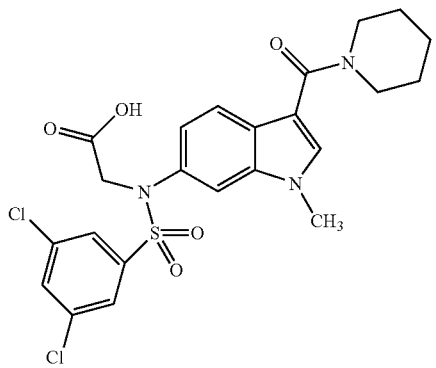

Mass spectrum (ESI⁺): m/z=524 [M+H]⁺

(52) [(3,5-dichloro-phenylsulphonyl)-(1-methyl-3-phenylcarbamoyl-1H-indol-6-yl)-amino]-acetic acid

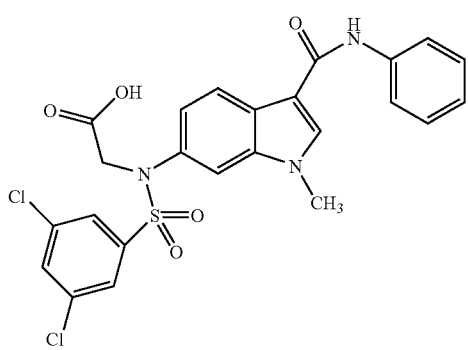

Mass spectrum (ESI⁺): m/z=532 [M+H]⁺

(53) [(3-benzylcarbamoyl-1-methyl-1H-indol-6-yl)-(3,5-dichloro-phenylsulphonyl)-amino]-acetic acid

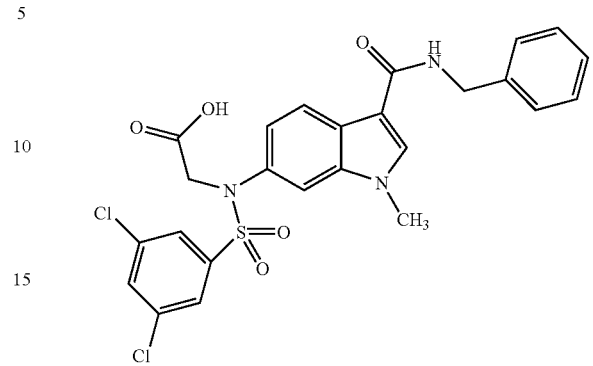

Mass spectrum (ESI⁻): m/z=544 [M−H]⁻

(54) [(3,5-dimethyl-phenylsulphonyl)-(1-methylcarbamoyl-2,3-dihydro-1H-indol-5-yl)-amino]-acetic acid

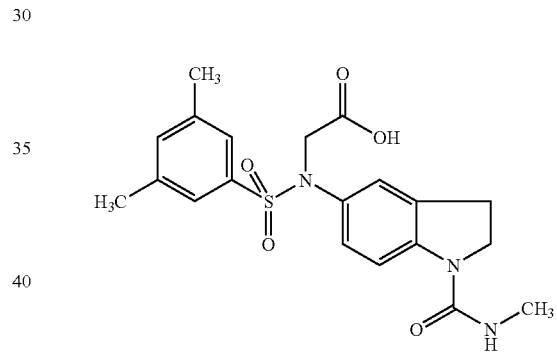

Mass spectrum (ESI⁺): m/z=418 [M+H]⁺

(55) [(3,5-dichloro-phenylsulphonyl)-(3-dimethylcarbamoyl-1H-indol-6-yl)-amino]-acetic acid

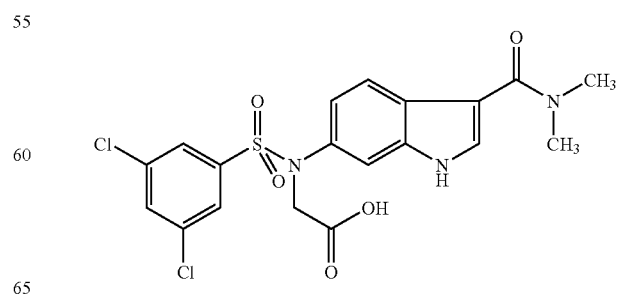

Mass spectrum (ESI⁺): m/z=470 [M+H]⁺

(56) [(3-aminooxalyl-1-methyl-1H-indol-6-yl)-(3,5-dichloro-phenylsulphonyl)-amino]-acetic acid

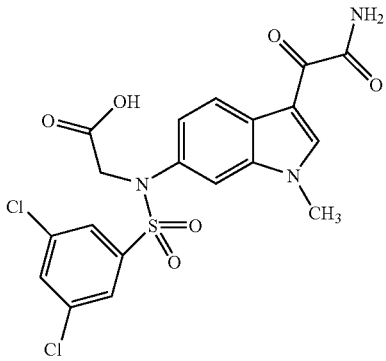

Mass spectrum (ESI⁻): m/z=482 [M–H]⁻

(57) [(3,5-dichloro-phenylsulphonyl)-(1-methyl-3-methylaminoox-alyl-1H-indol-6-yl)-amino]-acetic acid

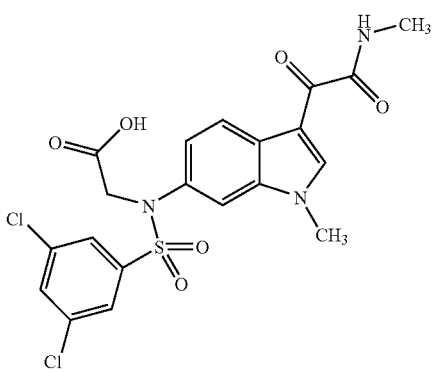

Mass spectrum (ESI⁺): m/z=498 [M+H]⁺

(58) [(3,5-dichloro-phenylsulphonyl)-(3-dimethylaminooxalyl-1-methyl-1H-indol-6-yl)-amino]-acetic acid

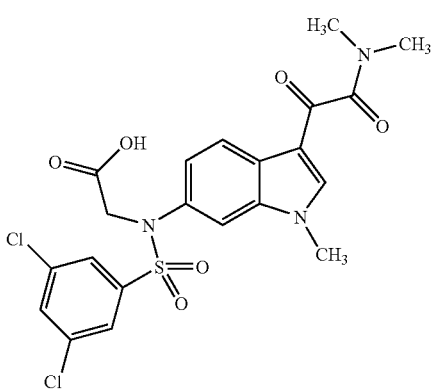

Mass spectrum (ESI⁺): m/z=512 [M+H]⁺

(59) {(3,5-dichloro-phenylsulphonyl)-[1-methyl-3-(2-oxo-2-pyrrolidin-1-yl-acetyl)-1H-indol-6-yl]-amino}-acetic acid

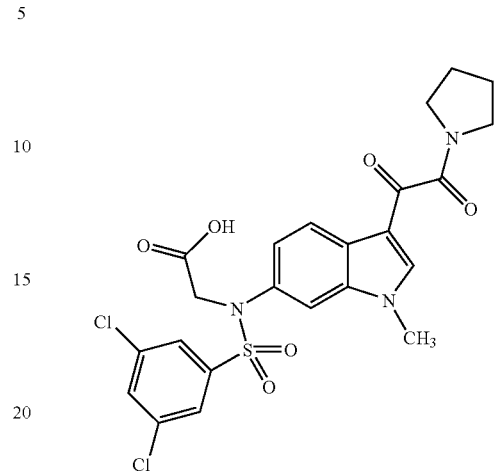

Mass spectrum (ESI⁻): m/z=536 [M–H]⁻

(60) [[3-(azetidine-1-carbonyl)-1-methyl-1H-indol-6-yl]-(3,5-dichloro-phenylsulphonyl)-amino]-acetic acid

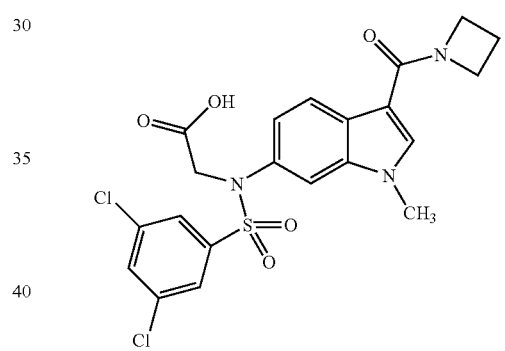

Mass spectrum (ESI⁺): m/z=496 [M+H]⁺

(61) [(3,5-dichloro-phenylsulphonyl)-(1,3-dimethyl-2-oxo-2,3-dihydro-1H-benzimidazol-5-yl)-amino]-acetic acid

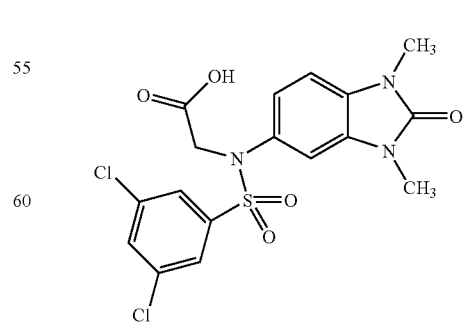

Mass spectrum (ESI⁺): m/z=444 [M+H]⁺

(62) 5-[carboxymethyl-(3,5-dichloro-phenylsulpho-nyl)-amino]-1-methylcarbamoyl-2,3-dihydro-1H-indole-3-carboxylic acid

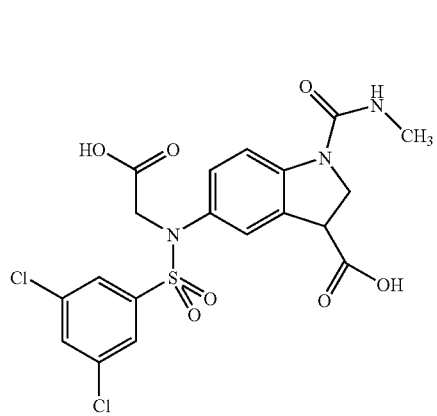

Mass spectrum (ESI⁻): m/z=500 [M−H]⁺

(63) {(3,5-dichloro-phenylsulphonyl)-[1-(2-methyl-carbamoyl-pyrrolidine-1-carbonyl)-2,3-dihydro-1H-indol-5-yl]-amino}-acetic acid

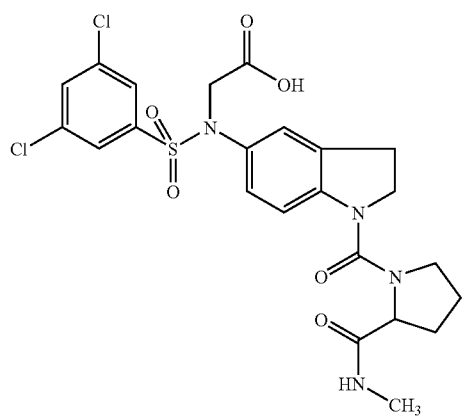

Mass spectrum (ESI⁺): m/z=555 [M+H]⁺

(64) [(3-carbamoyl-1-methylcarbamoyl-2,3-dihydro-1H-indol-5-yl)-(3,5-dichloro-phenylsulphonyl)-amino]-acetic acid

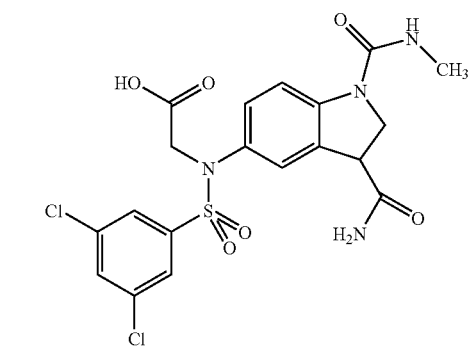

Mass spectrum (ESI⁺): m/z=501 [M+H]⁺

(65) {(3,5-dichloro-phenylsulphonyl)-[3-(3-hydroxy-pyrrolidine-1-carbonyl)-1-methyl-1H-indol-6-yl]-amino}-acetic acid

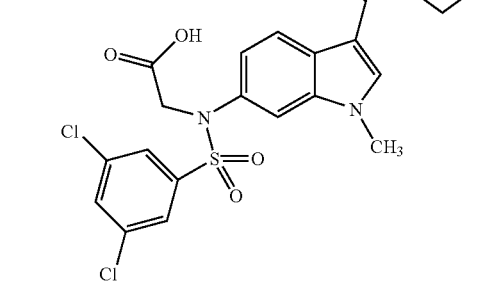

Mass spectrum (ESI⁺): m/z=526 [M+H]⁺

(66) [(3-cyclopropylcarbamoyl-1-methyl-1H-indol-6-yl)-(3,5-dichloro-phenylsulphonyl)-amino]-acetic acid

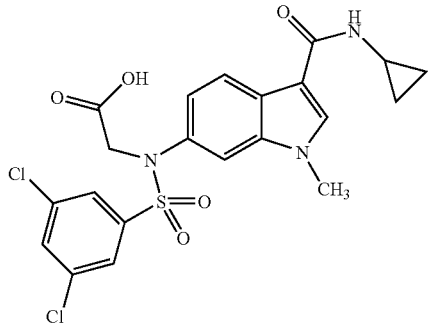

Mass spectrum (ESI⁺): m/z=496 [M+H]⁺

(67) [[3-(cyclopropyl-methyl-carbamoyl)-1-methyl-1H-indol-6-yl]-(3,5-dichloro-phenylsulphonyl)-amino]-acetic acid

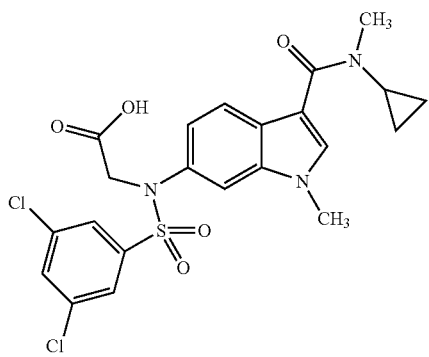

Mass spectrum (ESI⁺): m/z=510 [M+H]⁺

(68) {(3,5-dichloro-phenylsulphonyl)-[1-methyl-3-(2-methylcarbamoyl-pyrrolidine-1-carbonyl)-1H-indol-6-yl]-amino}-acetic acid

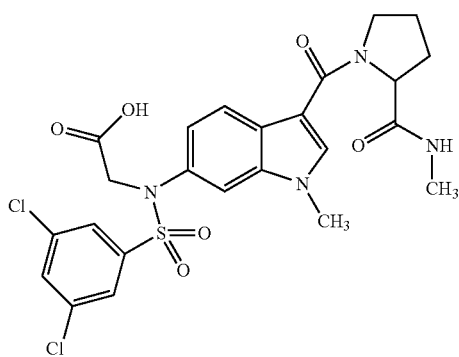

Mass spectrum (ESI⁺): m/z=567 [M+H]⁺

(69) {(3-chloro-5-methyl-phenylsulphonyl)-[1-methyl-3-(pyrrolidine-1-carbonyl)-1H-indol-6-yl]-amino}acetic acid

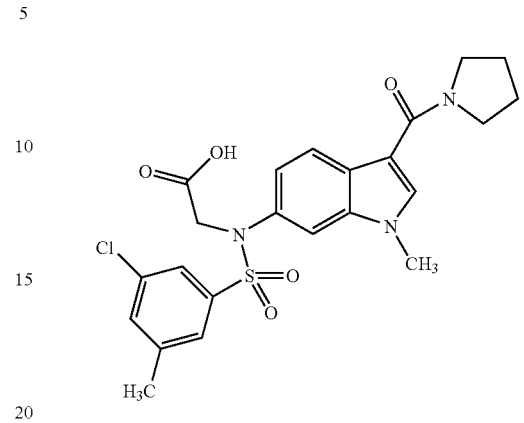

Mass spectrum (ESI⁺): m/z=490 [M+H]⁺

(70) {(3,5-dimethyl-phenylsulphonyl)-[1-methyl-3-(pyrrolidine-1-carbonyl)-1H-indol-6-yl]-amino}-acetic acid

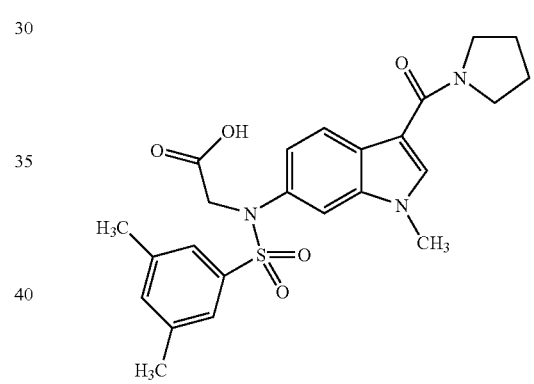

Mass spectrum (ESI⁺): m/z=470 [M+H]⁺

(71) {(3,5-dichloro-phenylsulphonyl)-[1-methyl-3-(pyrrolidine-1-carbonyl)-1H-indazol-6-yl]-amino}-acetic acid

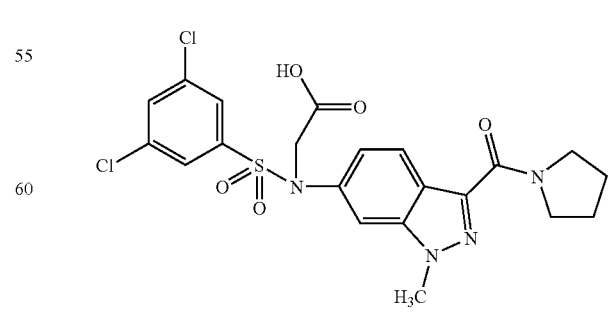

Mass spectrum (ESI⁺): m/z=511 [M+H]⁺

(72) [(3,5-dichloro-phenylsulphonyl)-(1-methyl-3-methylcarbamoyl-1H-indazol-6-yl)-amino]-acetic acid

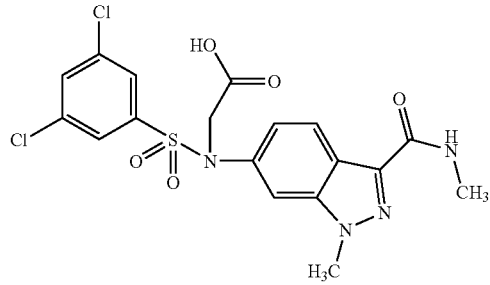

Mass spectrum (ESI⁺): m/z=471 [M+H]⁺

(73) [(3-carbamoyl-benzo[b]thiophene-6-yl)-(3,5-dichloro-phenylsulphonyl)-amino]-acetic acid

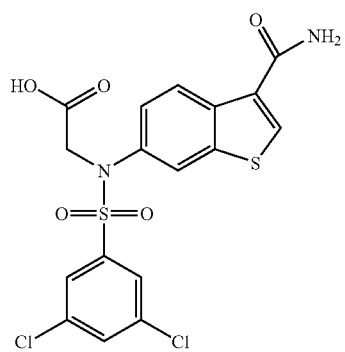

Mass spectrum (ESI⁺): m/z=476 [M+NH₄]⁺

(74) [(3-carbamoyl-benzo[b]thiophene-5-yl)-(3,5-dichloro-phenylsulphonyl)-amino]-acetic acid

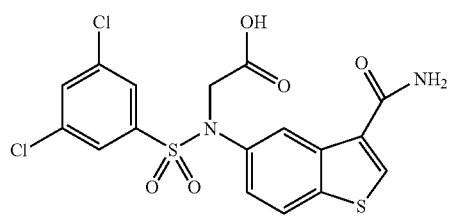

Mass spectrum (ESI⁻): m/z=457 [M–H]⁻

(75) [(3,5-dichloro-phenylsulphonyl)-(3-hydroxymethyl-1-methylcarbamoyl-2,3-dihydro-1H-indol-5-yl)-amino]-acetic acid

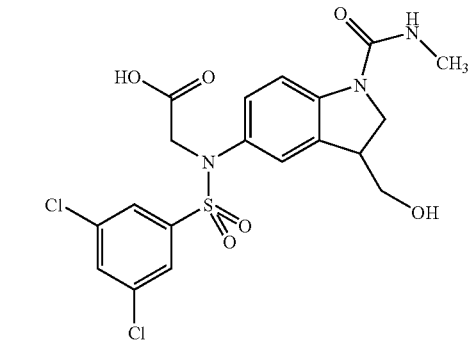

Mass spectrum (ESI⁺): m/z=488 [M+H]⁺

EXAMPLE 2

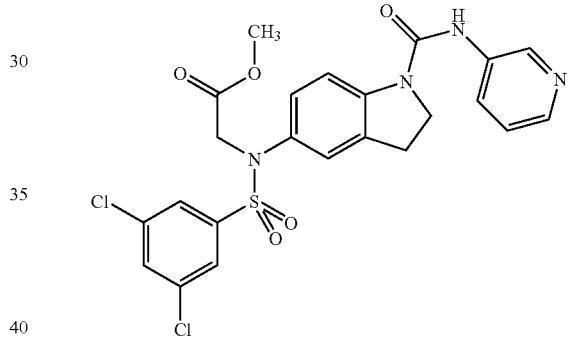

Methyl {(3,5-dichloro-phenylsulphonyl)-[1-(pyridin-3-ylcarbamoyl)-2,3-dihydro-1H-indol-5-yl]-amino}-acetate 610 mg tert-butyl 5-[(3,5-dichloro-phenylsulphonyl)-methoxycarbonylmethyl-amino]-2,3-dihydro-indole-1-carboxylate are dissolved in 8 ml dichloromethane. 4 ml of trifluoroacetic acid are added with stirring. The mixture is stirred for 2 hours at ambient temperature and then the solvents are eliminated in vacuo. The residue is divided between saturated sodium hydrogen carbonate solution and ethyl acetate. The aqueous phase is extracted twice with ethyl acetate. The combined organic phases are dried on sodium sulphate. The solvents are eliminated in vacuo and the residue is taken up in 10 ml dichloromethane. 245 mg potassium carbonate and 150 mg 3-pyridylisocyanate are added and the mixture is stirred overnight at ambient temperature. The solvent is eliminated in vacuo and the residue is divided between water and ethyl acetate. A solid is precipitated which is suction filtered and dried in vacuo.

Yield: 340 mg (54% of theory)

Mass spectrum (ESI⁺): m/z=535 [M+H]⁺

EXAMPLE 3

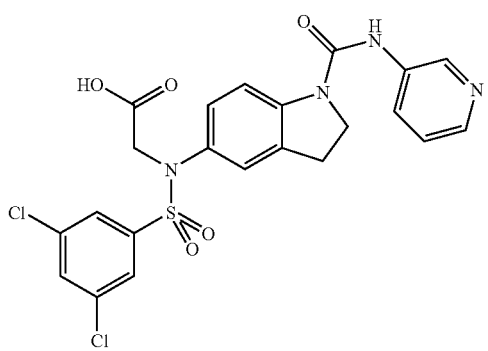

{(3,5-dichloro-phenylsulphonyl)-[1-(pyridin-3-ylcarbamoyl)-2,3-dihydro-1H-indol-5-yl]-amino}-acetic acid 220 mg tert.butyl [(3,5-dichloro-phenylsulphonyl)-(2,3-dihydro-1H-indol-5-yl)-amino]-acetate are dissolved in 10 ml dichloromethane. 166 mg potassium carbonate and 121 mg 3-pyridylisocyanate are added and the mixture is stirred overnight at ambient temperature. The reaction mixture is divided between water and dichloromethane. The aqueous phase is extracted twice with dichloromethane and the combined organic phases are dried on sodium sulphate. The solvent is eliminated in vacuo and the residue is taken up in 8 ml dichloromethane. 4 ml trifluoroacetic acid are added and the mixture is stirred for 2 hours at ambient temperature. The solvents are eliminated in vacuo and the residue is extracted from diisopropylether and petroleum ether. The solid is suction filtered and dried in vacuo.

Mass spectrum (ESI$^+$): m/z=521 [M+H]$^+$

EXAMPLE 4

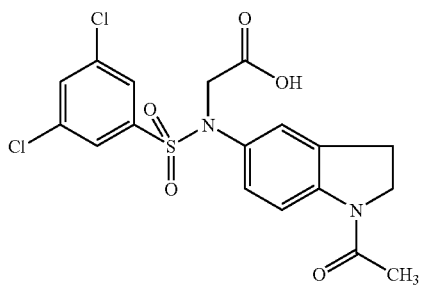

[(1-acetyl-2,3-dihydro-1H-indol-5-yl)-(3,5-dichloro-phenylsulphonyl)-amino]-acetic acid 40 mg [(3,5-dichloro-phenylsulphonyl)-(2,3-dihydro-1H-indol-5-yl)-amino]-acetic acid are dissolved in 2 ml dichloromethane. 100 µl acetic anhydride are added and the mixture is stirred overnight at ambient temperature. The volatile constituents are eliminated in vacuo and the residue is purified by chromatography on silica gel with dichloromethane/methanol (99:1 to 85:15). The product thus obtained is extracted from diethyl ether/diisopropylether. The solid is suction filtered and dried in vacuo.

Yield: 15 mg (34% of theory)
Mass spectrum (ESI$^+$): m/z=443 [M+H]$^+$

EXAMPLE 5

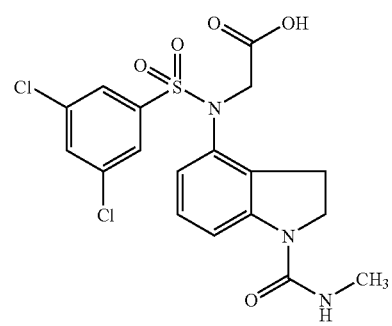

[(3,5-dichloro-phenylsulphonyl)-(1-methylcarbamoyl-2,3-dihydro-1H-indol-4-yl)-amino]-acetic acid 300 mg tert.butyl [(3,5-dichloro-phenylsulphonyl)-(1-methylcarbamoyl-2,3-dihydro-1H-indol-4-yl)-amino]-acetate are dissolved in 4 ml of a 4 N solution of HCl in dioxane. The mixture is stirred overnight at RT and the solvents are then eliminated in vacuo. The residue is extracted from dichloromethane.

Yield: 155 mg (58% of theory)
Mass spectrum (ESI$^+$): m/z=458 [M+H]$^+$

The following compounds are obtained analogously to Example 5:

(1) [(3,5-dichloro-phenylsulphonyl)-(1-phenylcarbamoyl-2,3-dihydro-1H-indol-4-yl)-amino]-acetic acid

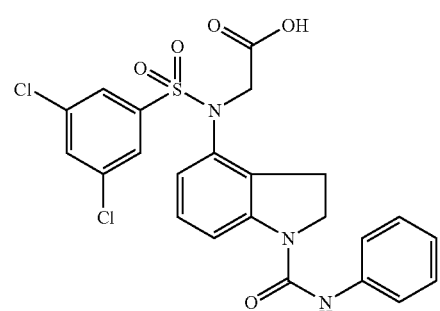

Mass spectrum (ESI$^+$): m/z=520 [M+H]$^+$ (2) {(3,5-dichloro-phenylsulphonyl)-[1-(pyridin-3-ylcarbamoyl)-2,3-dihydro-1H-indol-4-yl]-amino}-acetic acid*HCl

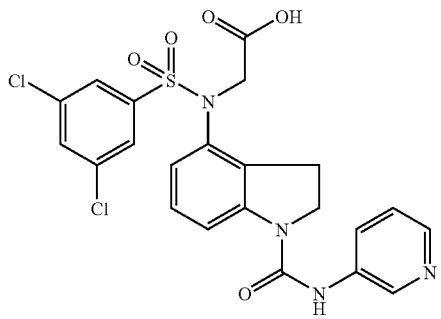

The crude product is extracted from diethyl ether.
Mass spectrum (ESI⁺): m/z=521 [M+H]⁺

(3) methyl 5-[carboxymethyl-(3,5-dichloro-phenyl-sulphonyl)-amino]-2,3-dihydro-indole-1-carboxylate

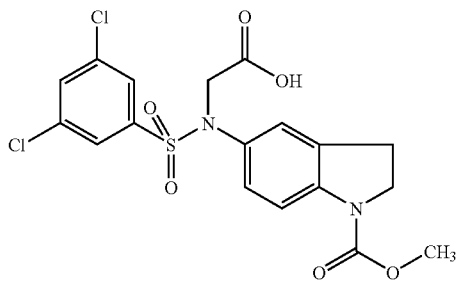

After the end of the reaction the dioxane is eliminated in vacuo. The residue is taken up in diethyl ether and the solid is filtered off. The solvent is eliminated in vacuo and the residue is purified by chromatography on silica gel. The product thus obtained is extracted from diisopropylether.

Mass spectrum (ESI⁺): m/z=476 [M+H]⁺

(4) [(3,5-dichloro-phenylsulphonyl)-(1-phenylcarbamoyl-2,3-dihydro-1H-indol-6-yl)-amino]-acetic acid

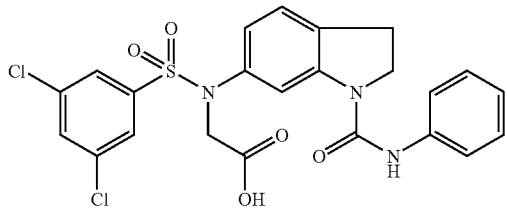

The crude product is extracted from diethyl ether.
Mass spectrum (ESI⁺): m/z=520 [M+H]⁺

(5) {(3,5-dichloro-phenylsulphonyl)-[1-(pyridin-4-ylcarbamoyl)-2,3-dihydro-1H-indol-5-yl]-amino}-acetic acid*HCl

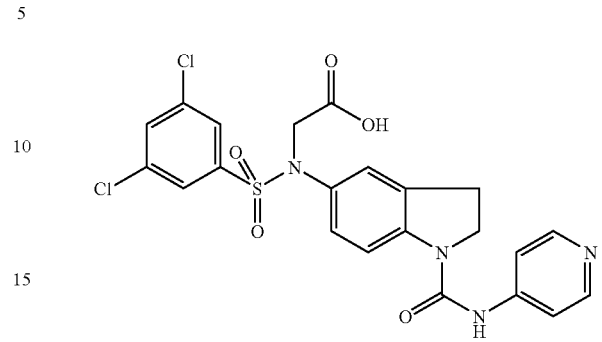

Mass spectrum (ESI⁺): m/z=521 [M+H]⁺

(6) [(3,5-dichloro-phenylsulphonyl)-(1H-indol-5-yl)-acetic acid

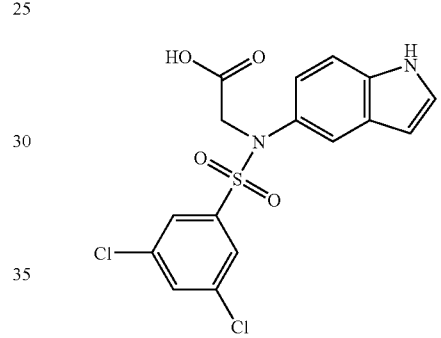

The crude product is extracted from diethyl ether.
Mass spectrum (EI): m/z=398 [M]⁺

EXAMPLE 6

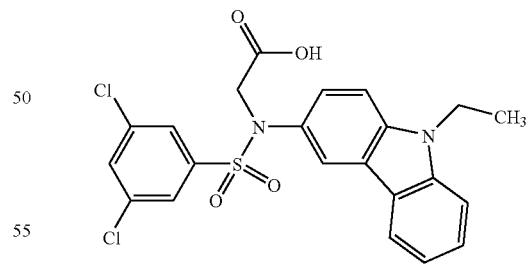

[(3,5-dichloro-phenylsulphonyl)-(9-ethyl-9H-carbazol-3-yl)-amino]-acetic acid 512 mg methyl [(3,5-dichloro-phenylsulphonyl)-(9-ethyl-9H-carbazol-3-yl)-amino]-acetate are dissolved in 5 ml of tetrahydrofuran. 3 ml 1 N sodium hydroxide solution are added and the mixture is stirred for 3 hours at ambient temperature. It is diluted with ice water and the precipitated solid is suction filtered. The solid is taken up in 15 ml dichloromethane and the organic phase is dried on magnesium sulphate. The solvent is eliminated in vacuo and the residue is chromatographed on silica gel with dichloromethane/methanol (10:0 to 9:1).

Yield: 24 mg (5% of theory)
Mass spectrum (ESI⁻): m/z=475 [M−H]⁻

EXAMPLE 7

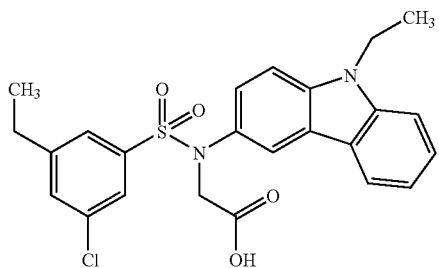

[(3-chloro-5-ethyl-phenylsulphonyl)-(9-ethyl-9H-carbazol-3-yl)-amino]-acetic acid 104 mg [(3-chloro-5-ethynyl-phenylsulphonyl)-(9-ethyl-9H-carbazol-3-yl)-amino]-acetic acid are dissolved in 5 ml of ethyl acetate. 30 mg of platinum dioxide are added and the mixture is hydrogenated for 5.5 hours at 3 bar hydrogen pressure. Then the catalyst is removed by suction filtering, the solvent is eliminated in vacuo and the residue is purified by preparative HPLC.

Yield: 38 mg (36% of theory)
Mass spectrum (ESI⁻): m/z=469 [M−H]⁻

EXAMPLE 8

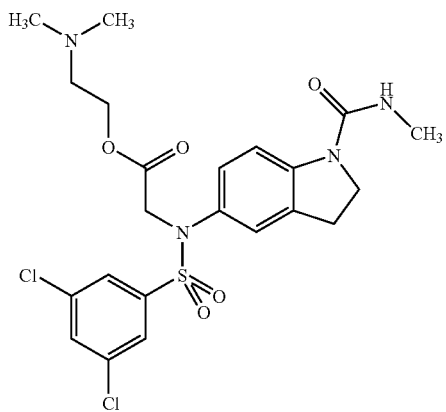

[(3,5-dichloro-phenylsulphonyl)-(1-methylcarbamoyl-2,3-dihydro-1H-indol-5-yl)-amino]-acetic acid-2-dimethylamino-ethylester*HCl 115 mg [(3,5-dichloro-phenylsulphonyl)-(1-methylcarbamoyl-2,3-dihydro-1H-indol-5-yl)-amino]-acetic acid are dissolved in 5 ml of tetrahydrofuran. 90 mg carbonyldiimidazole are added thereto and the mixture is refluxed for 1 hour. After another hour's stirring at ambient temperature 56 µl of 2-dimethylamine-ethanol are added. The mixture is refluxed for 2 hours and stirred for 1 hour at ambient temperature. Then the solvent is eliminated in vacuo and the residue is divided between ethyl acetate and 1 N sodium hydroxide solution. The organic phase is washed once with water and once with saturated sodium chloride solution. After drying with magnesium sulphate the solvent is eliminated in vacuo and the residue is taken up in 4 ml dichloromethane. 100 µl of a 4 N solution of hydrogen chloride in dioxane are added dropwise thereto. The solvent is then eliminated in vacuo and the residue is taken up twice in toluene and the latter is again eliminated in vacuo.

Yield: 105 mg (74% of theory)
Mass spectrum (ESI⁺): m/z=529 [M+H]⁺

(1) ethyl [(3,5-dichloro-phenylsulphonyl)-(1-methylcarbamoyl-2,3-dihydro-1H-indol-5-yl)-amino]-acetate

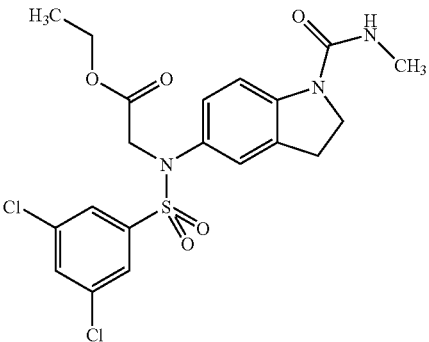

After the aqueous working up the crude product is extracted from ethyl acetate, diisopropylether and petroleum ether.

Mass spectrum (ESI⁺): m/z=486 [M+H]⁺

EXAMPLE 9

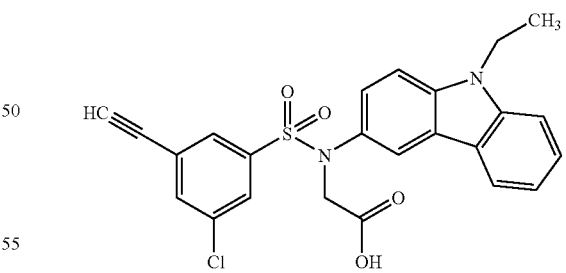

[(3-chloro-5-ethynyl-phenylsulphonyl)-(9-ethyl-9H-carbazol-3-yl)-amino]-acetic acid 134 mg [(3-chloro-5-trimethylsilylethynyl-phenylsulphonyl)-(9-ethyl-9H-carbazol-3-yl)-amino]-acetic acid are dissolved in 2 ml of methanol, combined with 50 mg potassium carbonate and stirred for 2 hours at ambient temperature. Then the mixture is diluted with dichloromethane and washed with 4 M hydrochloric acid. The organic phase is dried on magnesium sulphate and the solvent is then eliminated in vacuo. The residue is chromatographed on silica gel (dichloromethane/methanol 100:0 to 95:5).

Yield: 108 mg (93% of theory)
Mass spectrum (ESI⁻): m/z=465 [M−H]⁻

EXAMPLE 10

Coated Tablets Containing 75 Mg of Active Substance

1 Tablet Core Contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 11

Tablets Containing 100 mg of Active Substance

Composition:
1 Tablet Contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE 12

Tablets Containing 150 mg of Active Substance

Composition:
1 Tablet Contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 13

Hard Gelatine Capsules Containing 150 Mg of Active Substance

1 Capsule Contains:

| | | |
|---|---|---|
| active substance | | 50.0 mg |
| corn starch (dried) | approx. | 80.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 14

Suppositories Containing 150 Mg of Active Substance

1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

169

Preparation:

After the suppository mass has been melted the active substance is homogeneously distributed therein and the melt is poured into chilled moulds.

EXAMPLE 15

Suspension containing 50 mg of active substance

100 Ml of Suspension Contain:

| active substance | 1.00 g |
|---|---|
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 16

Ampoules Containing 10 Mg Active Substance

Composition:

| active substance | 10.0 mg |
|---|---|
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 17

Ampoules Containing 50 Mg of Active Substance

Composition:

| active substance | 50.0 mg |
|---|---|
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

170

The invention claimed is:

1. A compound of formula (I)

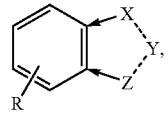

(I)

wherein
R denotes a group of formula

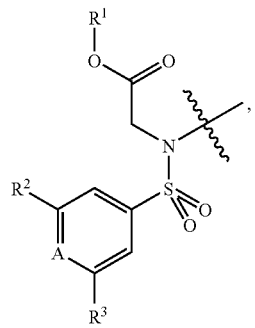

wherein
$R^1$ denotes H, $C_{1-6}$-alkyl or a group of formula

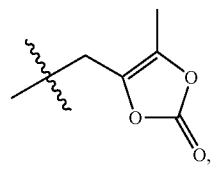

wherein the $C_{1-6}$-alkyl group mentioned for $R^1$ hereinbefore may be substituted by $C_{1-6}$-alkyl-carbonyloxy, $C_{1-6}$-alkoxy-carbonyloxy, $C_{1-6}$-alkoxy, hydroxy, amino, $C_{1-3}$-alkyl-amino, di-($C_{1-3}$-alkyl)-amino, pyrrolidin-1-yl, piperidin-1-yl, morpholin-4-yl, piperazin-1-yl, 4-($C_{1-3}$-alkyl)-piperazin-1-yl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, tetrahydrofuran-3-yl-oxy, $C_1$-3-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy or 4-($C_{1-3}$-alkyl)-piperazin-1-yl-$C_{1-3}$-alkyloxy, $R^2$ and $R^3$ independently of one another denote halogen, $C_{1-3}$-alkyl, $C_{2-4}$-alkynyl, $C_{1-3}$-perfluoroalkyl, $C_{1-3}$-perfluoroalkoxy, $C_{1-3}$-alkoxy, cyano, nitro or hydroxy, and A denotes CH or N,
and the heterocyclic group

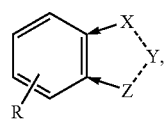

denotes a group of formula

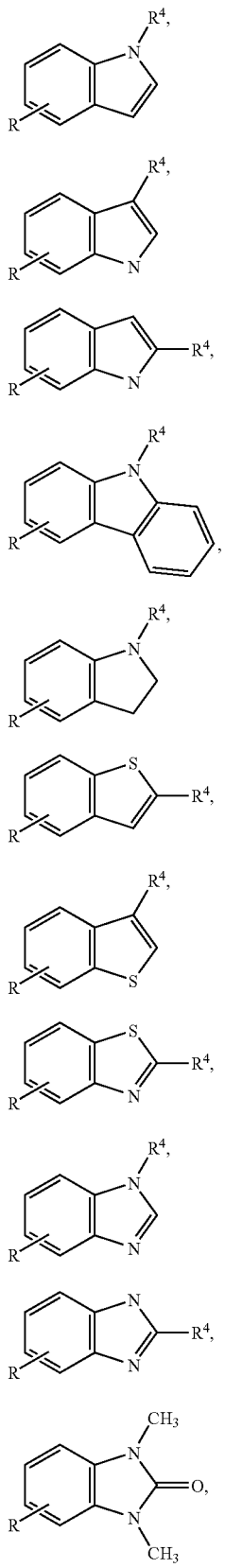

(Ia)
(Ib)
(Ic)
(Id)
(Ie)
(If)
(Ig)
(Ih)
(Ii)
(Ij)
(Ik)

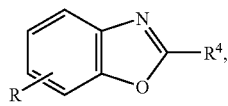 (Im)

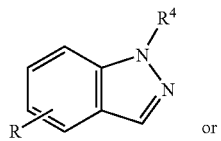 (In)

or

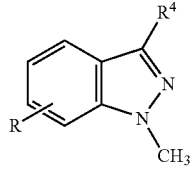 (Io)

wherein the above-mentioned heterocycles of formulae (Ia), (Ib), (Ic), (Ie), (If), (Ig), (Ii) and (In) may each optionally be substituted at the carbon atoms of the 5 ring by one or two groups selected from among $C_{1-3}$-alkyl, amino-$C_{1-3}$-alkyl, hydroxy-$C_{1-3}$-alkyl, cyano, $C_{1-3}$-perfluoroalkyl, $C_{3-6}$-cycloalkyl, $C_{2-4}$-alkynyl, $C_{2-4}$-alkenyl, $C_{1-3}$-alkyl-carbonyl, $C_{1-3}$-perfluoroalkyl-carbonyl, carboxyl, $C_{1-3}$-alkyloxy-carbonyl, carboxy-$C_{1-3}$-alkyl, aminocarbonyl, $C_{1-3}$-alkyl-aminocarbonyl or di-($C_{1-3}$-alkyl)- aminocarbonyl, wherein the groups may be identical or different and each carbon atom may carry only one group, and wherein the above-mentioned heterocyclic group of formula (Ib) may optionally be substituted at the nitrogen atom of the 5 ring by methyl or hydroxycarbonylmethyl, and wherein $R^4$ denotes H, cyano, $C_{1-6}$-alkyl, phenyl-$C_{1-6}$-alkyl, phenylsulphonyl-$C_{1-6}$-alkyl, $C_{1-6}$-alkyl-carbonyl, carboxyl, $C_{1-6}$-alkoxy-carbonyl, phenylcarbonyl, phenyl-$C_{1-6}$-alkyl-carbonyl, 5-chloro-1H-indol-2-yl-carbonyl, aminocarbonyl, $C_{1-6}$-alkyl-aminocarbonyl, di-($C_{1-6}$-alkyl)-aminocarbonyl, $C_{3-6}$-cycloalkyl-aminocarbonyl, N-($C_{3-6}$-cycloalkyl)-N-($C_{1-6}$-alkyl)-aminocarbonyl, aryl-amino-carbonyl, N-oxy-pyridylaminocarbonyl, 4- to 7-membered cycloalkyleneimino-carbonyl optionally substituted by hydroxy or $C_{1-3}$-alkyl-aminocarbonyl, morpholin-4-yl-carbonyl, piperazin-1-yl-carbonyl, 4-($C_{1-3}$-alkyl)-piperazin-1-yl-carbonyl, (piperazin-2-on-4-yl)-carbonyl, aminocarbonyl-carbonyl, $C_{1-3}$-alkylaminocarbonyl-carbonyl, di-($C_{1-3}$-alkyl)-amino-carbonyl-carbonyl, pyrrolidin-1-ylcarbonyl-carbonyl, piperidin-1-ylcarbonyl-carbonyl, morpholin-4-ylcarbonyl-carbonyl, piperazin-1-ylcarbonyl-carbonyl, 4-methyl-piperazin-1-ylcarbonyl-carbonyl, $C_{1-3}$-alkyl-sulphonyl, phenyl-$C_{1-3}$-alkylsulphonyl or phenylsulphonyl optionally substituted in the phenyl moiety by one or two chlorine atoms, wherein the $C_{1-6}$-alkyl-aminocarbonyl, di-($C_{1-6}$-alkyl)-aminocarbonyl and N-($C_{3-6}$-cycloalkyl)-N-($C_{1-6}$-alkyl)-aminocarbonyl group mentioned above in the definition of $R^4$ may each be substituted in the alkyl moiety by aryl, $C_{1-3}$-alkyl-amino, di-($C_{1-3}$-alkyl)-amino, $C_{3-6}$-cycloalkyl-amino, N-(C$_{3-6}$-cycloalkyl)N-(C$_{1-6}$-alkyl)-amino, pyrrolidin-1-yl, piperidin-1-yl, morpholin-4-yl, piperazin-1-yl, 4-methyl-piperazin-1-yl or C$_{1-3}$-alkylaminocarbonyl, and wherein the aryl group mentioned above in the definition of R$^4$ is a 6-membered aromatic system that may contain 0 to 3 nitrogen atoms and may be substituted by nitro.

or a tautomer, stereoisomer, mixture thereof or salt thereof.

2. The compound of formula (I) according to claim 1, wherein

R denotes a group of the formula given in claim 1, wherein R$^1$ denotes H, C$_{1-6}$-alkyl or a group of formula

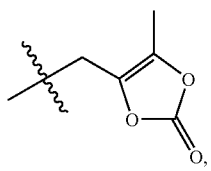

wherein the C$_{1-6}$-alkyl group mentioned for R$^1$ hereinbefore may be substituted by C$_{1-6}$-alkyl-carbonyloxy, C$_{1-6}$-alkoxy-carbonyloxy, C$_{1-6}$-alkoxy, hydroxy, amino, C$_{1-3}$-alkyl-amino, di-(C$_{1-3}$-alkyl)-amino, pyrrolidin-1-yl, piperidin-1-yl, morpholin-4-yl, piperazin-1-yl, 4-(C$_{1-3}$-alkyl)-piperazin-1-yl, aminocarbonyl, C$_{1-3}$-alkyl-aminocarbonyl, di-(C$_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-(C$_{1-3}$-alkyl)-piperazin-1-yl-carbonyl, R$^2$ and R$^3$ independently of one another denote halogen, C$_{1-3}$-alkyl, C$_{2-4}$-alkynyl, C$_{1-3}$-perfluoroalkyl, C$_{1-2}$-alkoxy or cyano and A denotes CH or N, and the heterocyclic group

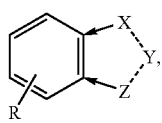

denotes a group of formula

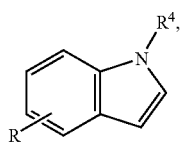 (Ia)

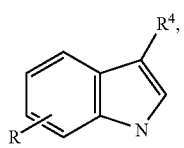 (Ib)

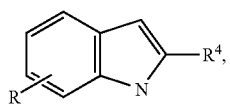 (Ic)

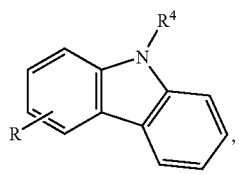 (Id)

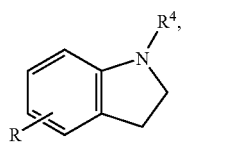 (Ie)

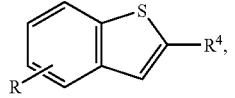 (If)

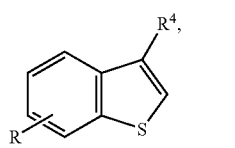 (Ig)

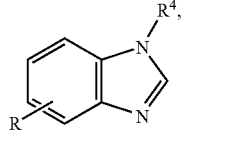 (Ii)

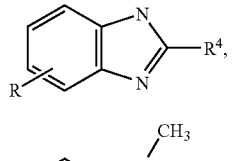 (Ij)

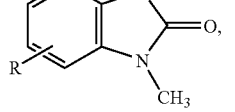 (Ik)

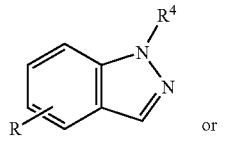 (In)

or

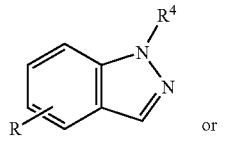 (Io)

wherein the above-mentioned heterocycles of formulae (Ia), (Ib), (Ic), (Ie), (If), (Ig), (Ii) and (In) may each optionally be substituted at the carbon atoms of the 5 ring by one or two groups selected from among C$_{1-3}$-alkyl, amino-C$_{1-3}$-alkyl, hydroxy-C$_{1-3}$-alkyl, cyano, C$_{3-6}$-cycloalkyl, C$_{1-3}$-alkyl-carbonyl, C$_{1-3}$-perfluoroalkyl-carbonyl, carboxyl, C$_{1-2}$-alkyloxy-carbonyl, carboxy-C$_{1-2}$-alkyl, aminocarbonyl, C$_{1-3}$-alkyl-aminocarbonyl or di-(C$_{1-3}$-alkyl)-aminocarbonyl, wherein the groups may be identical or different and each carbon atom may carry only one group, and wherein the above-mentioned heterocyclic group of formula (Ib) may optionally be substituted at the nitrogen atom of the 5 ring by methyl or hydroxycarbonylmethyl, and wherein $R^4$ denotes H, cyano, $C_{1-4}$-alkyl, phenyl-$C_{1-4}$-alkyl, phenylsulphonyl-$C_{1-4}$-alkyl, $C_{1-4}$-alkyl-carbonyl, carboxyl, $C_{1-4}$-alkoxy-carbonyl, phenylcarbonyl, phenyl-$C_{1-4}$-alkyl-carbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N-($C_{3-6}$-cycloalkyl)-N-($C_{1-4}$-alkyl)-aminocarbonyl, [N, N-di-($C_{1-4}$-alkyl)-amino]-$C_{1-3}$-alkyl-amino-carbonyl, 1-(methylaminocarbonyl)-ethyl-amino-carbonyl, aryl-amino-carbonyl, aryl-$C_{1-3}$-alkyl-amino-carbonyl, N-oxy-pyridylamino-carbonyl, 4- to 7-membered cycloalkyleneimino-carbonyl optionally substituted by hydroxy or methylaminocarbonyl, morpholin-4-yl-carbonyl, piperazin-1-yl-carbonyl, 4-(methyl)-piperazin-1-yl-carbonyl, (piperazin-2-on-4-yl)l-carbonyl, aminocarbonyl-carbonyl, $C_{1-2}$-alkylaminocarbonyl-carbonyl, di-($C_{1-2}$-alkyl)-amino-carbonyl-carbonyl, pyrrolidin-1-ylcarbonyl-carbonyl, piperidin-1-ylcarbonyl-carbonyl, morpholin-4-ylcarbonyl-carbonyl, $C_{1-2}$-alkyl-sulphonyl, phenyl-$C_{1-2}$-alkyl-sulphonyl or phenylsulphonyl optionally substituted in the phenyl moiety by one or two chlorine atoms, wherein the aryl group mentioned above in the definition of $R^4$ is a 6-membered aromatic system that may contain 0 to 2 nitrogen atoms and may be substituted by nitro, or a tautomer, stereoisomer, mixture thereof or salt thereof.

3. The compound of formula (I) according to claim 1, wherein

R denotes a group of the formula given in claim 1, wherein $R^1$ denotes H, $C_{1-4}$-alkyl or a group of formula

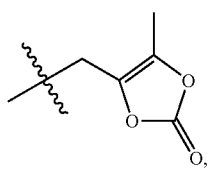

wherein the $C_{1-4}$-alkyl group mentioned for $R^1$ hereinbefore may be substituted by $C_{1-4}$-alkoxy, hydroxy, di-($C_{1-3}$-alkyl)-amino, pyrrolidin-1-yl, piperidin-1-yl, morpholin-4-yl, piperazin-1-yl or 4-(methyl)-piperazin-1-yl, $R^2$ and $R^3$ independently of one another denote chlorine, bromine, $C_{1-2}$-alkoxy, $C_{2-3}$-alkynyl or $C_{1-2}$-alkyl and A denotes CH or N, and the heterocyclic group

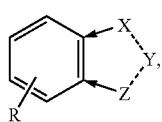

denotes a group of formula

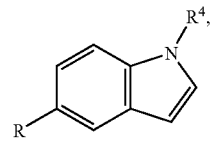
(Ia1)

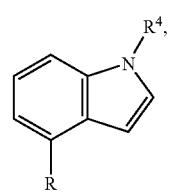
(Ia2)

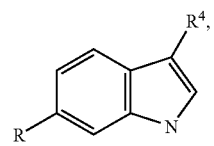
(Ib1)

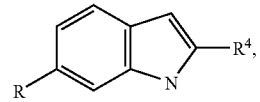
(Ic1)

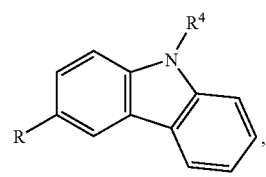
(Id1)

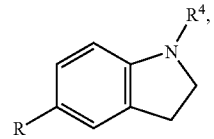
(Ie1)

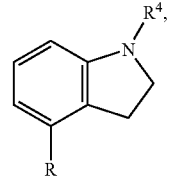
(Ie2)

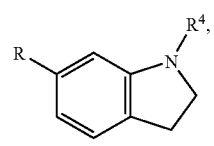
(Ie3)

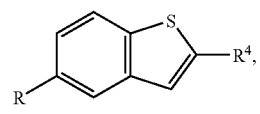
(If1)

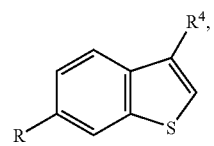
(Ig1)

-continued

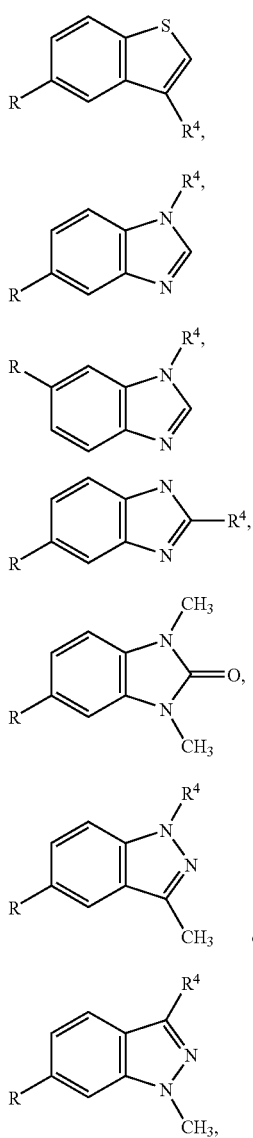

wherein the above-mentioned heterocycles of formulae (Ia1), (Ia2) and (Ie1) may each optionally be substituted at the carbon atoms of the 5 ring by a group selected from among $C_{1-2}$-alkyl, methylcarbonyl, trifluoromethylcarbonyl, carboxyl, methoxy-carbonyl, aminocarbonyl, methyl-aminocarbonyl, dimethyl-aminocarbonyl, aminomethyl or hydroxymethyl, and wherein the above-mentioned heterocyclic group of formula (Ib1) may optionally be substituted at the nitrogen atom of the 5 ring by methyl or hydroxycarbonylmethyl, and wherein $R^4$ denotes H, cyano, $C_{1-4}$-alkyl, phenyl-$C_{1-4}$-alkyl, phenylsulphonyl-$C_{1-4}$-alkyl, $C_{1-4}$-alkyl-carbonyl, carboxyl, $C_{1-4}$-alkoxy-carbonyl, phenylcarbonyl, phenyl-$C_{1-4}$-alkyl-carbonyl, 5-chloro-1H-indol-2-yl-carbonyl, aminocarbonyl, $C_{1-4}$-alkyl-aminocarbonyl, di-($C_{1-4}$-alkyl)-aminocarbonyl, $C_{3-6}$-cycloalkyl-aminocarbonyl, N-($C_{3-6}$-cycloalkyl)-N-($C_{1-4}$-alkyl)-aminocarbonyl, N,N-di-($C_{1-3}$-alkyl)-amino-$C_{1-3}$-alkyl-aminocarbonyl, 1-(methylaminocarbonyl)-ethyl-amino-carbonyl, phenylamino-carbonyl, (nitrophenyl)-amino-carbonyl, phenyl-$C_{1-2}$-alkyl-amino-carbonyl, pyridinylamino-carbonyl, pyrazinylamino-carbonyl, N-oxy-pyridylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, $C_{1-2}$-alkylaminocarbonyl-carbonyl, di-($C_{1-2}$-alkyl)-aminocarbonyl-carbonyl, pyrrolidin-1-ylcarbonyl-carbonyl, piperidin-1-ylcarbonyl-carbonyl, morpholin-4-ylcarbonyl-carbonyl, benzyl-sulphonyl, phenylsulphonyl or 3.5-dichloro-phenyl-sulphonyl, or a tautomer, stereoisomer, mixture thereof or salt thereof.

4. The compound of formula (I) according to claim 1, wherein

R denotes a group of the formula given in claim 1, wherein $R^1$ denotes H or a $C_{1-3}$-alkyl group optionally substituted by a di-($C_{1-3}$-alkyl)-amino group, $R^2$ and $R^3$ independently of one another represent chlorine, ethynyl, methoxy, methyl or ethyl and A denotes CH or N, and the heterocyclic group

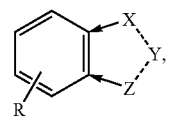

denotes a group of formula

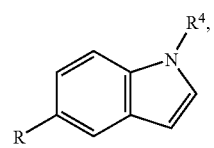   (Ia1)

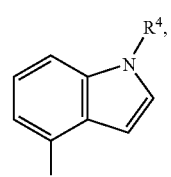   (Ia2)

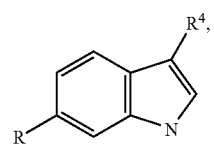   (Ib1)

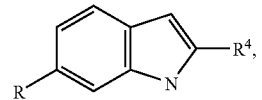   (Ic1)

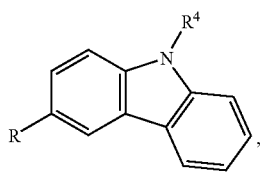
(Id1)

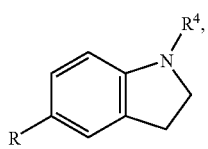
(Ie1)

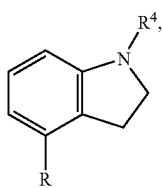
(Ie2)

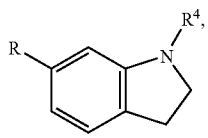
(Ie3)

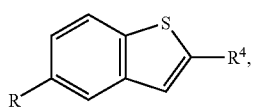
(If1)

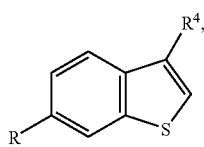
(Ig1)

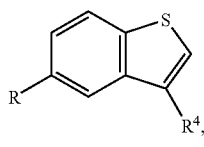
(Ig2)

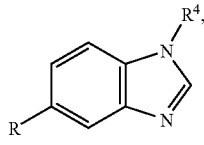
(Ii1)

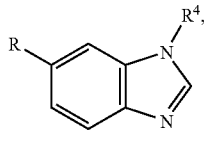
(Ii2)

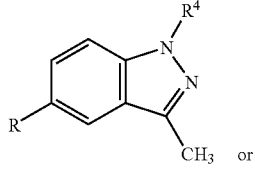
(In1)

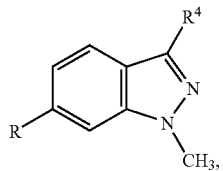
(Io1)

wherein the above-mentioned heterocycles of formulae (Ia1) and (Ie1) may each optionally be substituted at the carbon atoms of the 5 ring by a group selected from among $C_{1-2}$alkyl, trifluoromethylcarbonyl, carboxyl, hydroxycarbonylmethyl, aminocarbonyl or hydroxymethyl, and wherein the above-mentioned heterocyclic group of formula (Ib1) may optionally be substituted at the nitrogen atom of the 5 ring by methyl or hydroxycarbonylmethyl, and wherein $R^4$ denotes H, cyano, $C_{1-3}$-alkyl, phenyl-$C_{1-2}$-alkyl, phenylsulphonyl-$C_{1-2}$-alkyl, $C_{1-3}$-alkyl-carbonyl, $C_{1-2}$-alkoxy-carbonyl, phenylcarbonyl, phenyl-$C_{1-2}$-alkyl-carbonyl, 5-chloro-1H-indol-2-yl-carbonyl, aminocarbonyl, $C_{1-3}$-alkyl-aminocarbonyl, di-($C_{1-3}$-alkyl)-aminocarbonyl, cyclo-propyl-aminocarbonyl, N-(cyclopropyl)-N-($C_{1-2}$-alkyl)-aminocarbonyl, (N,N-dimethyl-amino)-ethyl-amino-carbonyl, 1-(methylaminocarbonyl)-ethyl-amino- carbonyl, phenylamino-carbonyl, (nitrophenyl)-amino-carbonyl, phenyl-$C_{1-3}$-alkyl-carbonyl, phenyl-$C_{1-2}$-alkyl-amino-carbonyl, pyridinylamino-carbonyl, pyrazinylamino-carbonyl, N-oxy-pyridin-3-ylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, $C_{1-2}$-alkylaminocarbonyl-carbonyl, di-($C_{1-2}$-alkyl)-amino-carbonyl-carbonyl, pyrrolidin-1-ylcarbonyl-carbonyl, benzyl-sulphonyl or phenyl-sulphonyl, or a tautomer, stereoisomer, mixture thereof or salt thereof.

5. The compound of formula (I) according to claim 1, wherein

R denotes a group of the formula given in claim 1, wherein $R^1$ denotes H, methyl, ethyl or 2-dimethylamino-ethyl, $R^2$ and $R^3$ independently of one another denote chlorine, ethynyl, methoxy, methyl or ethyl and A denotes CH or N, and the heterocyclic group

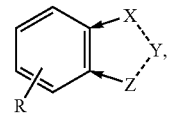

which may be substituted by $R^4$ as hereinbefore described, denotes a group of formula

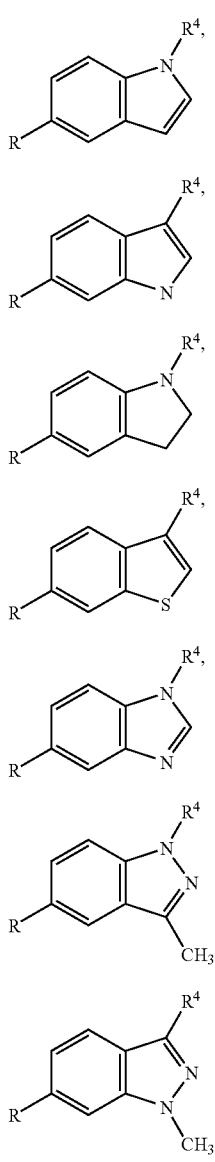

wherein the above-mentioned heterocyclic group of formula (Ia1) may optionally be substituted by trifluoromethylcarbonyl at the carbon atom of the 5 ring adjacent to the phenyl ring, and wherein the above-mentioned heterocyclic group of formula (Ie1) may optionally be substituted by carboxyl, amino-carbonyl or hydroxymethyl at the carbon atom of the 5 ring adjacent to the phenyl ring, and wherein the above-mentioned heterocyclic group of formula (Ib1) may optionally be substituted by methyl or hydroxycarbonylmethyl at the nitrogen atom of the 5 ring, and wherein $R^4$ denotes H, cyano, ethyl, phenyl-ethyl, phenylsulphonyl-ethyl, methyl-carbonyl, methoxy-carbonyl, phenylcarbonyl, benzylcarbonyl, 5-chloro-1H-indol-2-yl-carbonyl, aminocarbonyl, methyl-aminocarbonyl, dimethyl-aminocarbonyl, cyclopropyl-amino-carbonyl, N-(cyclopropyl)-N-(methyl)-aminocarbonyl, (N,N-dimethyl-amino)-ethyl-amino-carbonyl, 1-(methylaminocarbonyl)-ethyl-amino-carbonyl, phenylamino-carbonyl, benzylamino-carbonyl, 3-nitro-phenylamino-carbonyl, 2-nitro-phenylamino-carbonyl, pyridin-3-ylamino-carbonyl, pyridin-4-ylamino-carbonyl, pyrazinylamino-carbonyl, N-oxy-pyridin-3-ylamino-carbonyl, azetidin-1-yl-carbonyl, pyrrolidin-1-yl-carbonyl, 3-hydroxy-pyrrolidin-1-yl-carbonyl, 2-(methylaminocarbonyl)-pyrrolidin-1-yl-carbonyl, piperidin-1-yl-carbonyl, morpholin-4-yl-carbonyl, piperazin-1-yl-carbonyl, (piperazin-2-on-4-yl)-carbonyl, aminocarbonyl-carbonyl, methylaminocarbonyl-carbonyl, dimethyl-aminocarbonyl-carbonyl, pyrrolidin-1-ylcarbonyl-carbonyl, benzyl-sulphonyl or phenyl-sulphonyl, or a tautomer, stereoisomer, mixture thereof or salt thereof.

6. A compound according to claim 1 selected from:

(1) [(3,5-dichloro-phenylsulphonyl)-(1-phenylcarbamoyl-1H-indol-5-yl)-amino]-acetic acid, (2) [(3,5-dichloro-phenylsulphonyl)-(1-phenylcarbamoyl-2,3-dihydro-1H-indol-5-yl)-amino]-acetic acid, (3) {(3,5-dichloro-phenylsulphonyl)-[1-(3-nitro-phenylcarbamoyl)-2,3-dihydro-1H-indol-5-yl]-amino}-acetic acid, (4) {(3,5-dichloro-phenylsulphonyl)-[1-(pyridin-3-ylcarbamoyl)-2,3-dihydro-1H-indol-5-yl]-amino}-acetic acid, (5) {(3,5-dichloro-phenylsulphonyl)-[1-(2-nitro-phenylcarbamoyl)-2,3-dihydro-1H-indol-5-yl]-amino}-acetic acid, (6) [(1-acetyl-2,3-dihydro-1H-indol-5-yl)-(3,5-dichloro-phenylsulphonyl)-amino]-acetic acid, (7) [(3,5-dichloro-phenylsulphonyl)-(1-methylcarbamoyl-2,3-dihydro-1H-indol-5-yl)-amino]-acetic acid, (8) {(3,5-dichloro-phenylsulphonyl)-[1-(pyridin-4-ylcarbamoyl)-2,3-dihydro-1H-indol-5-yl]-amino}-acetic acid, (9) [(2,6-dichloro-pyridine-4-sulphonyl)-(9-ethyl-9H-carbazol-3-yl)-amino]-acetic acid,

(10) {(3,5-dichloro-phenylsulphonyl)-(3-(morpholine-4-carbonyl)-1H-indol-6-yl)-amino}-acetic acid,

(11) [(3,5-dichloro-phenylsulphonyl)-(3-dimethylcarbamoyl-1-methyl-1H-indol-6-yl)-amino]-acetic acid,

(12) [(3,5-dichloro-phenylsulphonyl)-(3-methylcarbamoyl-benzo[b]thiophen-6-yl)-amino]-acetic acid,

(13) {(3,5-dichloro-phenylsulphonyl)-[1-methyl-3-(pyrrolidine-1-carbonyl)-1H-indol-6-yl]-amino}-acetic acid,

(14) [(3,5-dimethyl-phenylsulphonyl)-(1-methylcarbamoyl-2,3-dihydro-1H-indol-5-yl)-amino]-acetic acid,

(15) [[3-(azetidine-1-carbonyl)-1-methyl-1H-indol-6-yl]-(3,5-dichloro-phenylsulphonyl)-amino]-acetic acid,

(16) {(3,5-dichloro-phenylsulphonyl)-[3-(3-hydroxy-pyrrolidine-1-carbonyl)-1-methyl-1H-indol-6-yl]-amino}-acetic acid,

(17) [[3-(cyclopropyl-methyl-carbamoyl)-1-methyl-1H-indol-6-yl]-(3,5-dichloro-phenylsulphonyl)-amino]-acetic acid,

(18) {(3-chloro-5-methyl-phenylsulphonyl)-[1-methyl-3-(pyrrolidine-1-carbonyl)-1H-indol-6-yl]-amino}-acetic acid,

(19) {(3,5-dimethyl-phenylsulphonyl)-[1-methyl-3-(pyrrolidine-1-carbonyl)-1H-indol-6-yl]-amino}-acetic acid and

(20) [(3,5-dichloro-phenylsulphonyl)-(3-hydroxymethyl-1-methylcarb amoyl-2,3-dihydro-1H-indol-5-yl)-aminol]-acetic acid, or an enantiomer, mixture, or salt thereof.

7. A physiologically acceptable salt of the compound according to claim 1 with an inorganic or organic acid or base.

8. A pharmaceutical compositions comprising a compound according to claim 1, or a physiologically acceptable salt thereof, optionally together with one or more inert carriers and/or diluents.

9. A method of using the pharmaceutical composition according to claim 8 for the treatment of type II diabetes mellitus comprising administering the composition to a patient in need thereof.

10. A process for preparing a pharmaceutical composition, characterised in that a compound according to claim 1, or a physiologically acceptable salt thereof, is incorporated in one or more inert carriers and/or diluents by a non-chemical method.

11. A process for preparing a compound of formula I according to claim 1, characterised in that a) a compound of formula (IV)

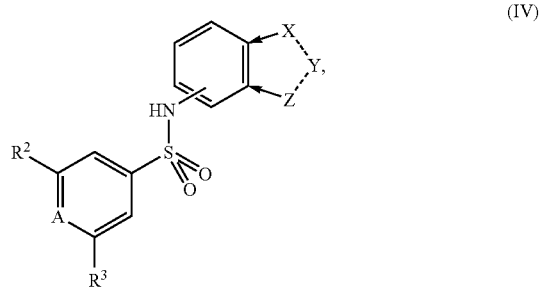

(IV)

wherein $R^2$, $R^3$, X, Y, Z and A are defined as in claim 1, is alkylated and b) if desired, any protective group used to protect reactive groups during the reactions is cleaved afterwards or simultaneously and/or c) a compound of formula I thus obtained is resolved into its stereoisomers and/or d) a compound of formula I thus obtained is converted into the salts thereof, particularly for pharmaceutical use into the physiologically acceptable salts thereof with an inorganic or organic acid or base.

* * * * *